United States Patent
Lillehoj et al.

(10) Patent No.: US 11,230,590 B2
(45) Date of Patent: *Jan. 25, 2022

(54) HYPERIMMUNIZED EGG PRODUCT FOR TREATMENT OF NECROTIC ENTERITIS IN POULTRY

(71) Applicants: The United States of America, as Represented by the Secretary of Agriculture, Washington, DC (US); Arkion Life Sciences, LLC, New Castle, DE (US)

(72) Inventors: Hyun S. Lillehoj, West Friendship, MD (US); Earnest W. Porta, Landenberg, PA (US); Samuel V. Walker, Elkton, MD (US); Leslie A. Confer, West Chester, PA (US); Ujvala Deepthi Gadde, Ashburn, VA (US); Cyril Gay, Bethesda, MD (US)

(73) Assignees: Arkion Life Sciences, LLC, New Castle, DE (US); United States of America, as Represented by the Secretary of Agriculture, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/574,954

(22) Filed: Sep. 18, 2019

(65) Prior Publication Data

US 2020/0002404 A1 Jan. 2, 2020

Related U.S. Application Data

(63) Continuation of application No. 15/895,636, filed on Feb. 13, 2018, now Pat. No. 10,450,364.

(60) Provisional application No. 62/458,180, filed on Feb. 13, 2017, provisional application No. 62/568,932, filed on Oct. 6, 2017.

(51) Int. Cl.

| | |
|---|---|
| *A61K 39/40* | (2006.01) |
| *C07K 16/02* | (2006.01) |
| *C07K 16/12* | (2006.01) |
| *C07K 16/20* | (2006.01) |
| *A61K 9/00* | (2006.01) |
| *A61K 47/46* | (2006.01) |
| *A23K 10/20* | (2016.01) |
| *A23K 10/18* | (2016.01) |
| *A61P 31/04* | (2006.01) |
| *A61P 29/00* | (2006.01) |
| *A23K 50/75* | (2016.01) |
| *A61K 39/00* | (2006.01) |

(52) U.S. Cl.
CPC ............. *C07K 16/02* (2013.01); *A23K 10/18* (2016.05); *A23K 10/20* (2016.05); *A23K 50/75* (2016.05); *A61K 9/0056* (2013.01); *A61K 47/46* (2013.01); *A61P 29/00* (2018.01); *A61P 31/04* (2018.01); *C07K 16/1282* (2013.01); *C07K 16/20* (2013.01); *A61K 2039/505* (2013.01); *A61K 2039/507* (2013.01); *C07K 2317/11* (2013.01); *C07K 2319/23* (2013.01)

(58) Field of Classification Search
None
See application file for complete search history.

(56) References Cited

U.S. PATENT DOCUMENTS

| | | | |
|---|---|---|---|
| 5,772,999 A | 6/1998 | Greenblatt et al. | |
| 6,420,337 B1 | 7/2002 | Iyer et al. | |
| 6,706,267 B1 | 3/2004 | Adalsteinsson et al. | |
| 6,803,035 B2 | 10/2004 | Greenblatt et al. | |
| 7,083,809 B2 | 8/2006 | Iyer et al. | |
| 10,450,364 B2 | 10/2019 | Lillehoj et al. | |
| 2003/0054493 A1* | 3/2003 | Williams | C07K 14/245 435/69.3 |
| 2011/0020356 A1 | 1/2011 | Fang et al. | |

FOREIGN PATENT DOCUMENTS

| | | | | |
|---|---|---|---|---|
| EP | 1552848 A1 * | 7/2005 | ............. | A61P 33/02 |
| WO | 97/35595 | 10/1997 | | |
| WO | 00/43020 | 7/2000 | | |

OTHER PUBLICATIONS

Lee et al. Veterinary Parasitology vol. 163, pp. 123-126, 2009 (Year: 2009).*
Jang et al. Vaccine vol. 30, pp. 5401-5406, 2012 (Year: 2012).*
Lillehoj et al. Avian Disease vol. 49, pp. 112-117, 2005. (Year: 2005).*
International Search Report based on co-pending PCT International Application No. PCT/US2018/018015, dated Jul. 20, 2018—6 Pages.

(Continued)

*Primary Examiner* — Jana A Hines
*Assistant Examiner* — Khatol S Shahnan Shah
(74) *Attorney, Agent, or Firm* — McCarter & English, LLP

(57) ABSTRACT

In one aspect, the present invention is directed to a method for preventing or treating necrotic enteritis by administering a hyperimmunized egg product obtained from an egg-producing animal to an avian. The hyperimmunized egg product may contain an antibody specific to an antigen selected from the group consisting of *Clostridium perfringens* α-toxin, *Clostridium perfringens* elongation factor Tu (EF-Tu), *Clostridium perfringens* necrotic enteritis B-like (NetB) toxin, *Clostridium perfringens* Pyruvate: Ferredoxin oxidoreductase (PFO), and *Eimeria tenella* elongation factor 1-alpha.

9 Claims, 27 Drawing Sheets

Specification includes a Sequence Listing.

(56) References Cited

OTHER PUBLICATIONS

Written Opinion based on co-pending PCT International Application No. PCT/US2018/018015, dated Jul. 20, 2018—7 Pages.
Invitation to Pay Additional Fees based on PCT International Application No. PCT/US2018/018015, dated May 31, 2018—3 Pages.
Wilkie, D.C., et al., "The effect of hen-egg antibodies on Clostridium perfringens colonization in the gastrointestinal tract of broiler chickens", Preventive Veterinary Medicine, Jun. 16, 2006, vol. 74, No. 4, pp. 279-292.
Thompson, D.R., et al., "Live attenuated vaccine-based control of necrotic enteritis of broiler chickens", Veterinary Microbiology, Nov. 11, 2005, vol. 113, No. 1-2, pp. 25-34.
Xu, JJ., et al. "Protection Efficacy of Multivalent Egg Yolk Immunoglobulin against Eimeria tenella Infection in Chickens", Iranian Journal of Parasitology, 2013, vol. 8, No. 3, pp. 449-458.
Arous, J. Ben, et al., "Development of drug-alternative strategy against coccidiosis: Enhancement of Eimeria profilin-induced vaccinal immunity by Montanide adjuvants in broiler chickens", Seppic, p. 1.
Gadde, U., et al., "Passive immunization with hyperimmune egg-yolk IgY as prophylaxis and therapy for poultry diseases—A review", Animal Health Research Reviews, 2015, pp. 1-14.
Lee, S.H., et al., "Induction of passive immunity in broiler chickens against Eimeria acervulina by hyperimmune egg yolk immunoglobulin Y1", Research Notes, 2009 Poultry Science, vol. 88, pp. 562-566.
Jang, Seung I., et al., "Vaccination with Clostridium perfringens recombinant proteins in combination with Montanide ISA 71 VG adjuvant increases protection against experimental necrotic enteritis in commercial broiler chickens", Vaccine, 2012, vol. 30, pp. 5401-5406.
Kulkarni, R.R., et al., "Immunization of Broiler Chickens against Clostridium perfringens-Induced Necrotic Enteritis", Clinical and Vaccine Immunology, Sep. 2007, vol. 14, No. 9, pp. 1070-1077.
Song, Min S., et al., Growth Inhibitors of Clostridium Perfringens Vegetative Cells and Spores Using Chicken Immunoglobulin Y, Journal of Food Safety, 2009, vol. 29, pp. 511-520.
Lee, S.H., et al., "Protective effect of hyperimmune egg yolk IgY antibodies against Eimeria tenella and Eimeria maxima infections", Veterinary Parasitology, 2009, vol. 163, pp. 123-126.
Jang, Seung I., et al, "Montanide ISA 71 VG adjuvant enhances antibody and cell-mediated immune responses to profilin subunit antigen vaccination and promotes protection against Eimeria acervulina and Eimeria tenella", Experimental Parasitology, 2011, vol. 127, pp. 178-183.
Tamilzarasan, K.B., et al., "Eficacy of Egg Yolk Immunoglobulins (IGY) Against Enteric Pathogens in Poultry", Veterinary & Animal Sciences 5, Nov.-Dec. 2009, vol. 6, pp. 264-268.
Matsubayashi, Makoto, et al., "Elongation factor-$1\alpha$ is a novel protein associated with host cell invasion and a potential protective antigen of Cryptosporidium parvum", The Journal of Biological Chemistry, Sep. 30, 2013, pp. 1-29.
Lee, Kyungwoo, et al., "Identification and cloning of two immunogenic Clostridium perfringens proteins, elongation factor Tu (EF-Tu) and pyruvate: ferredoxin oxidoreductase (PFO) of C. perfringens", Research in Veterinary Science, 2011, vol. 91, pp. e80-e86.
Lillehoj, eta al., Avian Disease vol. 49, pp. 112-117, 2005 (year 2005).

* cited by examiner

HYPERIMMUNIZED EGG PRODUCT FOR TREATMENT OF NECROTIC ENTERITIS IN POULTRY

RELATED APPLICATIONS

This application is a Continuation of U.S. Non-Provisional application Ser. No. 15/895,636, filed Feb. 13, 2018, which claims the benefit of U.S. Provisional Patent Application No. 62/458,180 filed on Feb. 13, 2017, and U.S. Provisional Patent Application No. 62/568,932 filed on Oct. 6, 2017, the contents of each of which are incorporated herein in their entirety.

RELATED FEDERALLY SPONSORED RESEARCH

The work described in this application was sponsored by USDA, Agricultural Research Service.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 099726_20501_US_Sequence_Listing. The size of the text file is 37 KB, and the text file was created on Sep. 18, 2019.

BACKGROUND

Necrotic enteritis (NE), caused by the bacterial pathogen *Clostridium perfringens*, is one of the most important infectious diseases in the current poultry production system. This disease globally causes severe economic losses due to mortality and decreased growth performance. Along with the increasing regulations for the removal of antibiotic growth promoters from poultry feed, the incidence of necrotic enteritis is also steadily increasing. The loss due to necrotic enteritis was estimated to be $2 billion dollars globally in the year 2000. But, a recent report published in World Poultry (Vol 31, No. 7, 2015) states that the true costs of necrotic enteritis are now closer to $6 billion dollars globally.

The modern poultry industry is largely dependent upon the use of antibiotics for treatment of bacterial diseases such as necrotic enteritis, and for growth promotion. However, in recent years, there have been several reports of the development of resistance to commonly used antibiotics in various pathogens. There is also increasing concern about the potential risks to human health from drug residues and the possible transfer of antibiotic-resistance genes from animal to human microbiota. In fact, the use of antibiotics for growth promotion has been banned in the European Union since 2006. In the US, many large producers are adopting non-antibiotic approaches for the prevention and treatment of various diseases and aiming at switching to completely antibiotic free production in couple of years. Thus a need exists for the development of efficient non-antibiotic strategies for the control and prevention of necrotic enteritis.

SUMMARY OF THE INVENTION

In certain aspects, the invention relates to a method for preventing or treating necrotic enteritis in an avian in need thereof, comprising administering to the avian a therapeutically effective amount of a hyperimmunized egg product obtained from an egg-producing animal, thereby preventing or treating the necrotic enteritis in the subject, wherein the hyperimmunized egg product comprises a therapeutically effective amount of an antibody to an antigen selected from the group consisting of *Clostridium perfringens* α-toxin, *Clostridium perfringens* elongation factor Tu (EF-Tu), *Clostridium perfringens* necrotic enteritis B-like (NetB) toxin, *Clostridium perfringens* Pyruvate: Ferredoxin oxidoreductase (PFO), and *Eimeria tenella* elongation factor 1-alpha.

In certain embodiments, the method further comprises hyperimmunizing the egg-producing animal with the antigen, collecting a hyperimmunized egg from the egg-producing animal that has been hyperimmunized, and preparing a hyperimmunized egg product from the hyperimmunized egg. In certain embodiments, the egg-producing animal is hyperimmunized with a composition comprising one or more of an antigenic protein, an antigenic bacterium, and a genetic vaccine. In certain embodiments, the egg-producing animal is an avian. In certain embodiments, the egg-producing animal is selected from the group consisting of fowl, turkey, duck, and goose. In certain embodiments, the avian is selected from the group consisting of chicken, turkey, goose, duck, pheasant, quail, pigeon and ostrich.

In certain embodiments, the composition comprises an antigenic protein selected from the group consisting of *Clostridium perfringens* α-toxin, *Clostridium perfringens* elongation factor Tu (EF-Tu), *Clostridium perfringens* necrotic enteritis B-like (NetB) toxin, *Clostridium perfringens* Pyruvate: Ferredoxin oxidoreductase (PFO), and *Eimeria tenella* elongation factor 1-alpha. In certain embodiments, the composition comprises at least two of the antigenic proteins. In certain embodiments, the at least two antigenic proteins are *Clostridium perfringens* elongation factor Tu (EF-Tu) and *Clostridium perfringens* necrotic enteritis B-like (NetB) toxin.

In certain embodiments, the antigenic bacterium is selected from the group consisting of *Escherichia coli; Escherichia coli* (Aerobacter); *Klebsiella pneumoniae; Pseudomonas aeruginosa; Salmonella typhimurium; Salmonella dysenteriae; Salmonella enteriditis; Salmonella epidermis; Salmonella simulans; Streptococcus pyogenes*, type 1; *Streptococcus pyogenes*, type 3; *Streptococcus pyogenes*, type 5; *Streptococcus pyogenes*, type 8; *Streptococcus pyogenes*, type 12; *Streptococcus pyogenes*, type 14; *Streptococcus pyogenes*, type 18; *Streptococcus pyogenes*, type 22; *Pseudomonas vulgaris; Streptococcus agalactiae; Streptococcus mitis; Streptococcus mutans; Streptococcus salavarius; Streptococcus sanguis; Streptococcus pneumoniae; Propionibacterium acnes*; and *Haemophilis influenzae*.

In certain embodiments, the genetic vaccine comprises DNA encoding a protein selected from the group consisting of *Clostridium perfringens* α-toxin, *Clostridium perfringens* elongation factor Tu (EF-Tu), *Clostridium perfringens* necrotic enteritis B-like (NetB) toxin, *Clostridium perfringens* Pyruvate: Ferredoxin oxidoreductase (PFO), and *Eimeria tenella* elongation factor 1-alpha. In certain embodiments, the genetic vaccine comprises DNA encoding at least two proteins selected from the group consisting of *Clostridium perfringens* α-toxin, *Clostridium perfringens* elongation factor Tu (EF-Tu), *Clostridium perfringens* necrotic enteritis B-like (NetB) toxin, *Clostridium perfringens* Pyruvate: Ferredoxin oxidoreductase (PFO), *Eimeria tenella* elongation factor 1-alpha, and *Eimeria tenella* 3-1E profilin. In certain embodiments, the at least two proteins are

*Clostridium perfringens* elongation factor Tu (EF-Tu) and *Clostridium perfringens* necrotic enteritis B-like (NetB) toxin.

In certain embodiments, the hyperimmunized egg product comprises at least 20% more by weight of an IgY antibody specific to an antigen selected from the group consisting of *Clostridium perfringens* α-toxin, *Clostridium perfringens* elongation factor Tu (EF-Tu), *Clostridium perfringens* necrotic enteritis B-like (NetB) toxin, *Clostridium perfringens* Pyruvate: Ferredoxin oxidoreductase (PFO), and *Eimeria tenella* elongation factor 1-alpha relative to a control egg product obtained from an egg-producing animal that is not hyperimmunized.

In certain embodiments, the hyperimmunized egg product comprises therapeutically effective amounts of at least two antibodies, each of which is specific to a different antigen selected from the group consisting of *Clostridium perfringens* α-toxin, *Clostridium perfringens* elongation factor Tu (EF-Tu), *Clostridium perfringens* necrotic enteritis B-like (NetB) toxin, *Clostridium perfringens* Pyruvate: Ferredoxin oxidoreductase (PFO), *Eimeria tenella* elongation factor 1-alpha, and *Eimeria tenella* 3-1E profilin. In certain embodiments, the hyperimmunized egg product comprises a therapeutically effective amount of an antibody to *Clostridium perfringens* elongation factor Tu (EF-Tu), and a therapeutically effective amount of an antibody to *Clostridium perfringens* necrotic enteritis B-like (NetB) toxin. In certain embodiments, the hyperimmunized egg product comprises a therapeutically effective amount of an antibody to a bacterium selected from the group consisting of *Escherichia coli*; *Escherichia coli* (Aerobacter); *Klebsiella pneumoniae*; *Pseudomonas aeruginosa*; *Salmonella typhimurium*; *Salmonella dysenteriae*; *Salmonella enteriditis*; *Salmonella epidermis*; *Salmonella simulans*; *Streptococcus pyogenes*, type 1; *Streptococcus pyogenes*, type 3; *Streptococcus pyogenes*, type 5; *Streptococcus pyogenes*, type 8; *Streptococcus pyogenes*, type 12; *Streptococcus pyogenes*, type 14; *Streptococcus pyogenes*, type 18; *Streptococcus pyogenes*, type 22; *Pseudomonas vulgaris*; *Streptococcus agalactiae*; *Streptococcus mitis*; *Streptococcus mutans*; *Streptococcus salavarius*; *Streptococcus sanguis*; *Streptococcus pneumoniae*; *Propionibacterium acnes*; and *Haemophilis influenzae*.

In certain embodiments, the hyperimmunized egg product comprises a therapeutically effective amount of a composition comprising antibodies to each of the following bacteria: *Escherichia coli*; *Escherichia coli* (Aerobacter); *Klebsiella pneumoniae*; *Pseudomonas aeruginosa*; *Salmonella typhimurium*; *Salmonella dysenteriae*; *Salmonella enteriditis*; *Salmonella epidermis*; *Salmonella simulans*; *Streptococcus pyogenes*, type 1; *Streptococcus pyogenes*, type 3; *Streptococcus pyogenes*, type 5; *Streptococcus pyogenes*, type 8; *Streptococcus pyogenes*, type 12; *Streptococcus pyogenes*, type 14; *Streptococcus pyogenes*, type 18; *Streptococcus pyogenes*, type 22; *Pseudomonas vulgaris*; *Streptococcus agalactiae*; *Streptococcus mitis*; *Streptococcus mutans*; *Streptococcus salavarius*; *Streptococcus sanguis*; *Streptococcus pneumoniae*; *Propionibacterium acnes*; and *Haemophilis influenzae*.

In certain embodiments, the hyperimmunized egg product is formulated as a microparticle or nanoparticle. In certain embodiments, the hyperimmunized egg product is encapsulated. In certain embodiments, the hyperimmunized egg product further comprises a therapeutically effective amount of an IgY antibody to *Eimeria tenella* 3-1E profilin. In certain embodiments, the composition further comprises *Eimeria tenella* 3-1E profilin. In certain embodiments, the genetic vaccine further comprises DNA encoding *Eimeria tenella* 3-1E profilin. In certain embodiments, the hyperimmunized egg product comprises at least 20% more by weight of an IgY antibody specific to *Eimeria tenella* 3-1E profilin relative to a control egg product obtained from an egg-producing animal that is not hyperimmunized. In certain embodiments, the antibody is an IgY antibody. In certain embodiments, the hyperimmunized egg product comprises: (a) a therapeutically effective amount of an antibody to an antigen selected from the group consisting of *Clostridium perfringens* α-toxin, *Clostridium perfringens* elongation factor Tu (EF-Tu), *Clostridium perfringens* necrotic enteritis B-like (NetB) toxin, and *Clostridium perfringens* Pyruvate: Ferredoxin oxidoreductase (PFO); and (b) a therapeutically effective amount of an antibody to an antigen selected from the group consisting of *Eimeria tenella* elongation factor 1-alpha and *Eimeria tenella* 3-1E profilin.

In certain embodiments, the composition comprises: (a) an antigenic protein selected from the group consisting of *Clostridium perfringens* α-toxin, *Clostridium perfringens* elongation factor Tu (EF-Tu), *Clostridium perfringens* necrotic enteritis B-like (NetB) toxin, and *Clostridium perfringens* Pyruvate: Ferredoxin oxidoreductase (PFO); and (b) an antigenic protein selected from the group consisting of *Eimeria tenella* elongation factor 1-alpha and *Eimeria tenella* 3-1E profilin. In certain embodiments, the hyperimmunized egg product is an aqueous concentrate. In certain embodiments, the hyperimmunized egg product is administered to the avian by addition to drinking water. In certain embodiments, the hyperimmunized egg product is an egg powder. In certain embodiments, the hyperimmunized egg product is administered to the avian by addition to feed.

In certain aspects the invention relates to a hyperimmunized egg produced by an animal that has been hyperimmunized with at least one antigen selected from the group consisting of *Clostridium perfringens* α-toxin, *Clostridium perfringens* elongation factor Tu (EF-Tu), *Clostridium perfringens* necrotic enteritis B-like (NetB) toxin, *Clostridium perfringens* Pyruvate: Ferredoxin oxidoreductase (PFO), and *Eimeria tenella* elongation factor 1-alpha, wherein the hyperimmunized egg comprises an increased level of an antibody to said at least one antigen relative to an egg from an animal that has not been hyperimmunized. In certain embodiments, the level of the antibody in the hyperimmunized egg is increased by at least 20% relative to the egg from the animal that has not been hyperimmunized. In certain embodiments, the level of antibodies to at least two of the antigens is increased relative to the egg from the animal that has not been hyperimmunized. In certain embodiments, the level of antibodies to *Clostridium perfringens* elongation factor Tu (EF-Tu) and *Clostridium perfringens* necrotic enteritis B-like (NetB) toxin in the hyperimmunized egg product is increased relative to the egg from the animal that has not been hyperimmunized. In certain embodiments, the hyperimmunized animal has also been hyperimmunized with *Eimeria tenella* 3-1E profilin. In certain embodiments, the level of antibodies to *Eimeria tenella* 3-1E profilin in the hyperimmunized egg is increased relative to the egg from the animal that has not been hyperimmunized.

In certain embodiments, the hyperimmunized animal has also been hyperimmunized with at least one antigenic bacterium selected from the group consisting of *Escherichia coli*; *Escherichia coli* (Aerobacter); *Klebsiella pneumoniae*; *Pseudomonas aeruginosa*; *Salmonella typhimurium*; *Salmonella dysenteriae*; *Salmonella enteriditis*; *Salmonella epidermis*; *Salmonella simulans*; *Streptococcus pyogenes*, type 1; *Streptococcus pyogenes*, type 3; *Streptococcus pyogenes*, type 5; *Streptococcus pyogenes*, type 8; *Streptococcus pyogenes*, type 12; *Streptococcus pyogenes*, type 14; *Streptococcus pyogenes*, type 18; *Streptococcus pyogenes*, type 22; *Pseudomonas vulgaris; Streptococcus agalactiae; Streptococcus mitis; Streptococcus mutans; Streptococcus salavarius; Streptococcus sanguis; Streptococcus pneumoniae; Propionibacterium acnes*; and *Haemophilis influenzae*. In certain embodiments, the hyperimmunized animal has been hyperimmunized with each of the following antigenic bacteria: *Escherichia coli; Escherichia coli* (Aerobacter); *Klebsiella pneumoniae; Pseudomonas aeruginosa; Salmonella typhimurium; Salmonella dysenteriae; Salmonella enteriditis; Salmonella epidermis; Salmonella simulans; Streptococcus pyogenes*, type 1; *Streptococcus pyogenes*, type 3; *Streptococcus pyogenes*, type 5; *Streptococcus pyogenes*, type 8; *Streptococcus pyogenes*, type 12; *Streptococcus pyogenes*, type 14; *Streptococcus pyogenes*, type 18; *Streptococcus pyogenes*, type 22; *Pseudomonas vulgaris; Streptococcus agalactiae; Streptococcus mitis; Streptococcus mutans; Streptococcus salavarius; Streptococcus sanguis; Streptococcus pneumoniae; Propionibacterium acnes*; and *Haemophilis influenzae*.

In certain embodiments, the hyperimmunized egg comprises an increased level of an antibody to at least one antigenic bacterium selected from the group consisting of *Escherichia coli; Escherichia coli* (Aerobacter); *Klebsiella pneumoniae; Pseudomonas aeruginosa; Salmonella typhimurium; Salmonella dysenteriae; Salmonella enteriditis; Salmonella epidermis; Salmonella simulans; Streptococcus pyogenes*, type 1; *Streptococcus pyogenes*, type 3; *Streptococcus pyogenes*, type 5; *Streptococcus pyogenes*, type 8; *Streptococcus pyogenes*, type 12; *Streptococcus pyogenes*, type 14; *Streptococcus pyogenes*, type 18; *Streptococcus pyogenes*, type 22; *Pseudomonas vulgaris; Streptococcus agalactiae; Streptococcus mitis; Streptococcus mutans; Streptococcus salavarius; Streptococcus sanguis; Streptococcus pneumoniae; Propionibacterium acnes*; and *Haemophilis influenzae*, relative to the egg product from the egg-producing animal that has not been hyperimmunized.

In certain aspects the invention relates to a hyperimmunized egg product obtained from a hyperimmunized egg described herein. In certain embodiments, the hyperimmunized egg product is formulated as a microparticle or nanoparticle. In certain embodiments, the hyperimmunized egg product is encapsulated. In certain embodiments, the hyperimmunized egg product is an aqueous concentrate. In certain embodiments, the hyperimmunized egg product is an egg powder. In certain embodiments, the egg powder is produced by spray-drying.

In certain aspects the invention relates to an animal feed comprising a hyperimmunized egg product described herein. In certain embodiments of the hyperimmunized eggs and hyperimmunized egg products described herein, the antibody is an IgY antibody. In certain embodiments, the egg-producing animal is an avian. In certain embodiments, the egg-producing animal is selected from the group consisting of fowl, turkey, duck, goose, chicken, pheasant, quail, pigeon and ostrich. In certain embodiments, the hyperimmunized egg product is an aqueous solution.

In some aspects, the present disclosure is directed to a method for preventing or treating necrotic enteritis in an avian in need thereof, comprising administering to the avian a therapeutically effective amount of a hyperimmunized egg product obtained from an egg-producing animal, thereby preventing or treating the necrotic enteritis in the subject, wherein the hyperimmunized egg product comprises a therapeutically effective amount of an antibody to an antigen selected from the group consisting of *Clostridium perfringens* α-toxin, *Clostridium perfringens* elongation factor Tu (EF-Tu), *Clostridium perfringens* necrotic enteritis B-like (NetB) toxin, *Clostridium perfringens* Pyruvate: Ferredoxin oxidoreductase (PFO), and *Eimeria tenella* elongation factor 1-alpha.

The present disclosure is further directed to the above method, wherein the hyperimmunized egg product comprises at least 20% more by weight of an IgY antibody specific to an antigen selected from the group consisting of *Clostridium perfringens* α-toxin, *Clostridium perfringens* elongation factor Tu (EF-Tu), *Clostridium perfringens* necrotic enteritis B-like (NetB) toxin, *Clostridium perfringens* Pyruvate: Ferredoxin oxidoreductase (PFO), and *Eimeria tenella* elongation factor 1-alpha relative to a control egg product obtained from an egg-producing animal that is not hyperimmunized.

The present disclosure is also directed to the above method, wherein the hyperimmunized egg product comprises therapeutically effective amounts of at least two antibodies, each of which is specific to a different antigen selected from the group consisting of *Clostridium perfringens* α-toxin, *Clostridium perfringens* elongation factor Tu (EF-Tu), *Clostridium perfringens* necrotic enteritis B-like (NetB) toxin, *Clostridium perfringens* Pyruvate: Ferredoxin oxidoreductase (PFO), *Eimeria tenella* elongation factor 1-alpha, and *Eimeria tenella* 3-1E profilin.

The present disclosure is further directed to the above method, wherein the hyperimmunized egg product comprises a therapeutically effective amount of an antibody to *Clostridium perfringens* elongation factor Tu (EF-Tu), and a therapeutically effective amount of an antibody to *Clostridium perfringens* necrotic enteritis B-like (NetB) toxin.

The present disclosure is further directed to the above method, wherein the hyperimmunized egg product further comprises a therapeutically effective amount of an IgY antibody to *Eimeria tenella* 3-1E profilin.

Finally, the present disclosure is directed to the above method, wherein the hyperimmunized egg product comprises (a) a therapeutically effective amount of an antibody to an antigen selected from the group consisting of *Clostridium perfringens* α-toxin, *Clostridium perfringens* elongation factor Tu (EF-Tu), *Clostridium perfringens* necrotic enteritis B-like (NetB) toxin, and *Clostridium perfringens* Pyruvate: Ferredoxin oxidoreductase (PFO); and (b) a therapeutically effective amount of an antibody to an antigen selected from the group consisting of *Eimeria tenella* elongation factor 1-alpha and *Eimeria tenella* 3-1E profilin.

Figure 15:
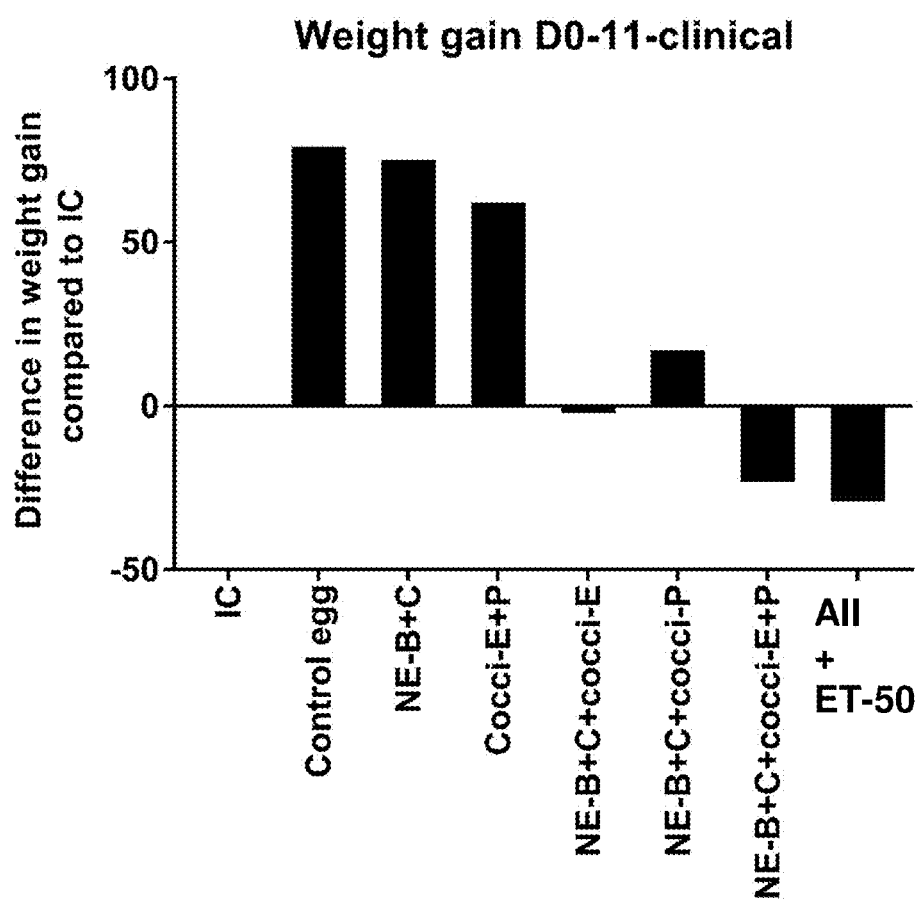

FIG. 15 shows the difference in body weight gain (mean±SEM) from infected control from Day 0 (day of *E. maxima* infection) to Day 11 (7 days post-*Clostridium perfringens* infection) in a subclinical model of necrotic enteritis infection. *E. maxima* infection was performed at 15 days of age and *Clostridium perfringens* infection at 19 days of age. Birds were fed feed supplemented with different egg powders at 0.1% level from 7 days before *Eimeria* infection. Birds that received standard diet with no egg powder supplementation served as non-supplemented and uninfected controls. Birds that received standard diet with no egg powder supplementation and given necrotic enteritis infection served as non-supplemented and infected controls. All the birds were given a low protein diet to 19 days of age and switched to a high protein diet to facilitate development of necrotic enteritis. Values with no common letter differ significantly (P≤0.05). IC=infected control; NE-B=*Clostridium perfringens* elongation factor Tu; NE-C=*Clostridium perfringens* necrotic enteritis B-like (NetB) toxin; Cocci-E=*Eimeria tenella* elongation factor 1-alpha; Cocci-P=*Eimeria tenella* 3-1E profilin.

Figure 16:
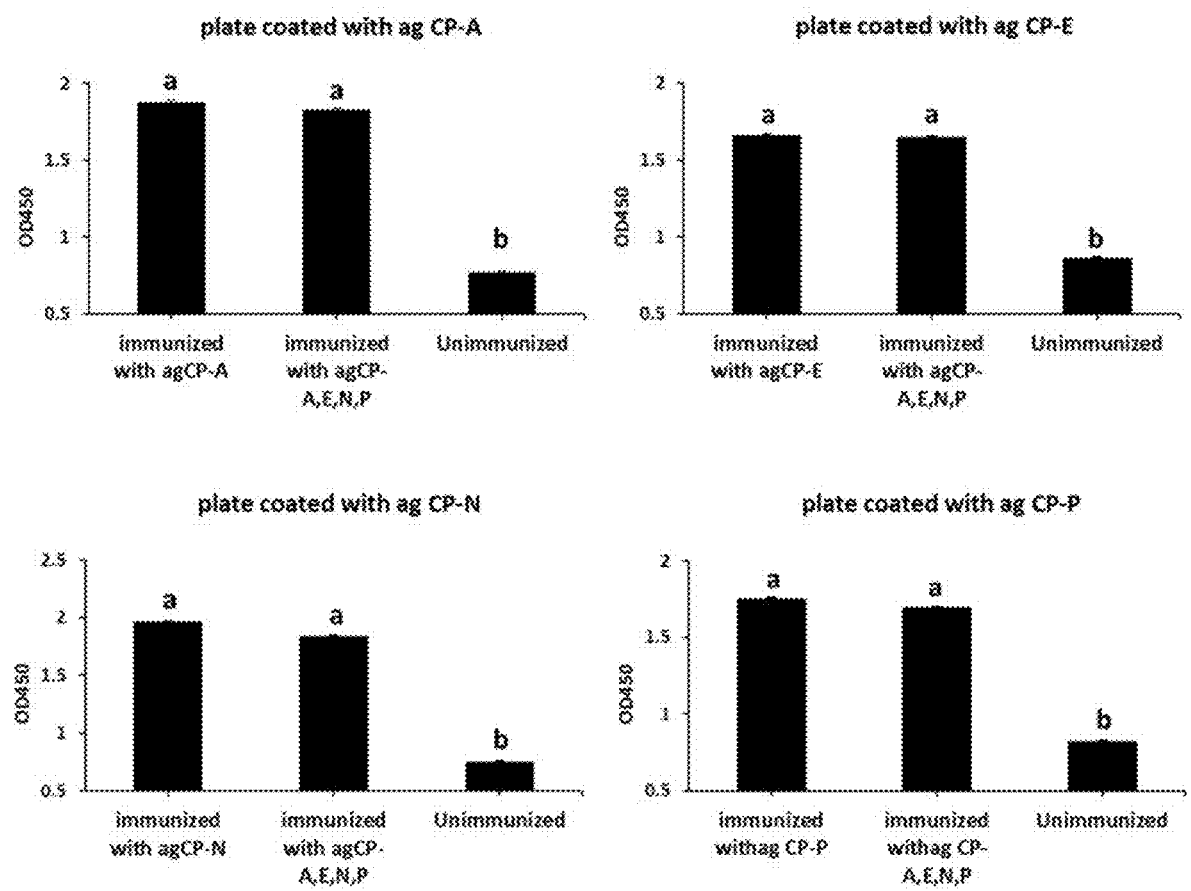

FIG. 16 shows specific IgY titers (mean $OD_{450}$) in eggs collected from hens hyperimmunized with various antigens of *Clostridium perfringens* (CP). Statistical values were considered with P<0.05. ag CP-A=*Clostridium perfringens* α-toxin; ag CP-E=*Clostridium perfringens* elongation factor Tu; ag CP-N=*Clostridium perfringens* necrotic enteritis B-like (NetB) toxin; ag CP-P=*Clostridium perfringens* Pyruvate: Ferredoxin oxidoreductase (PFO).

Figure 17:
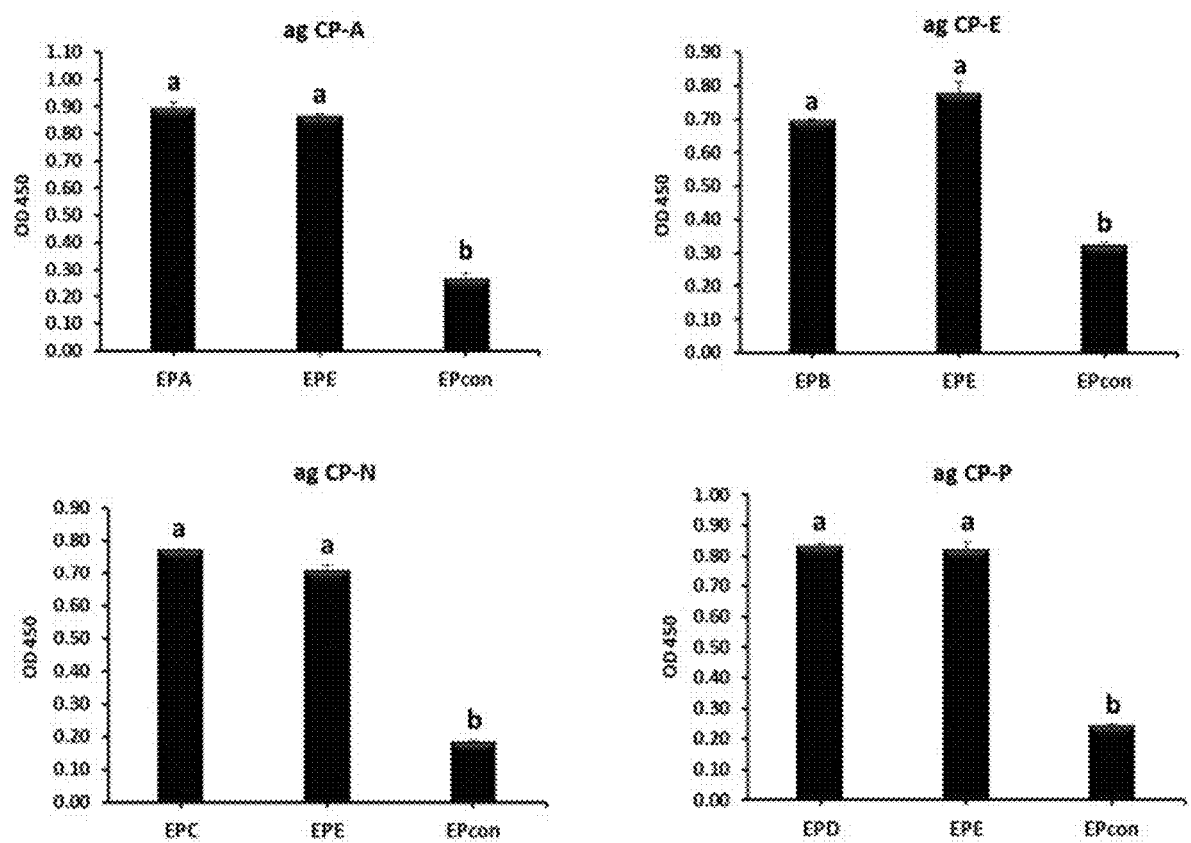

FIG. 17 shows antibody (IgY) titers (mean $OD_{450}$) in egg powders tested against the antigens with which they were raised and compared to that of control egg powder from unimmunized hens by ELISA. Egg powders were reconstituted in sterile PBS at 1 mg/mL and filtered through a 0.22 µm membrane filter. Serially diluted samples were used in ELISA. ag CP-A=*Clostridium perfringens* α-toxin; ag CP-E=*Clostridium perfringens* elongation factor Tu; ag CP-N=*Clostridium perfringens* necrotic enteritis B-like (NetB) toxin; ag CP-P=*Clostridium perfringens* Pyruvate: Ferredoxin oxidoreductase (PFO).

Figure 18:
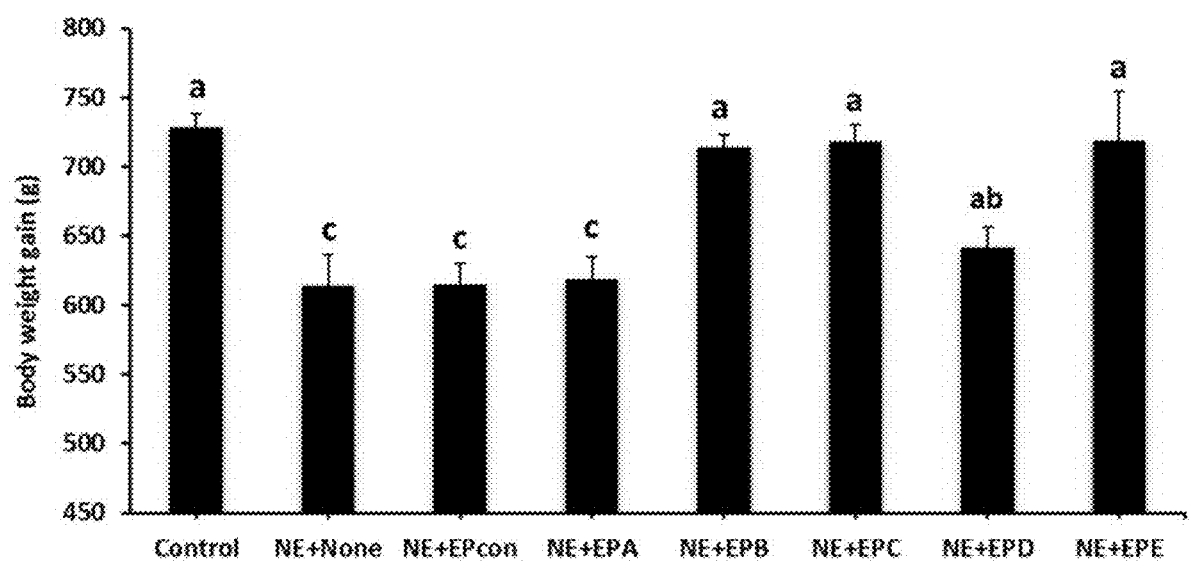

FIG. 18 shows the effect of dietary egg powder IgY supplementation on body weight gain following necrotic enteritis challenge in broilers. Chickens were fed with a non-supplemented diet (control, NE+None) or a diet supplemented with egg powder (EP) at 1% level from 17 days of age to the end of the experimental period. At 17 d post-hatch, birds were uninfected (control) or orally infected with $1\times10^4$ sporulated oocysts of *E. maxima* followed by oral inoculation with $1\times10^9$ CFU of *Clostridium perfringens* at 21 days post-hatch (all NE groups). Body weights were measured at d 17 and d 30 (11 d interval) and weight gains were calculated. Values are means with their standard errors represented by vertical bars (n=12). Treatment means with no common letter differ significantly (P≤0.05). EPA=*Clostridium perfringens* α-toxin; EPB=*Clostridium perfringens* elongation factor Tu; EPC=*Clostridium perfringens* necrotic enteritis B-like (NetB) toxin; EPD=*Clostridium perfringens* Pyruvate: Ferredoxin oxidoreductase (PFO); EPE=EPA+EPB+EPC+EPD; EPcon=egg powder from uninfected birds.

Figure 19:
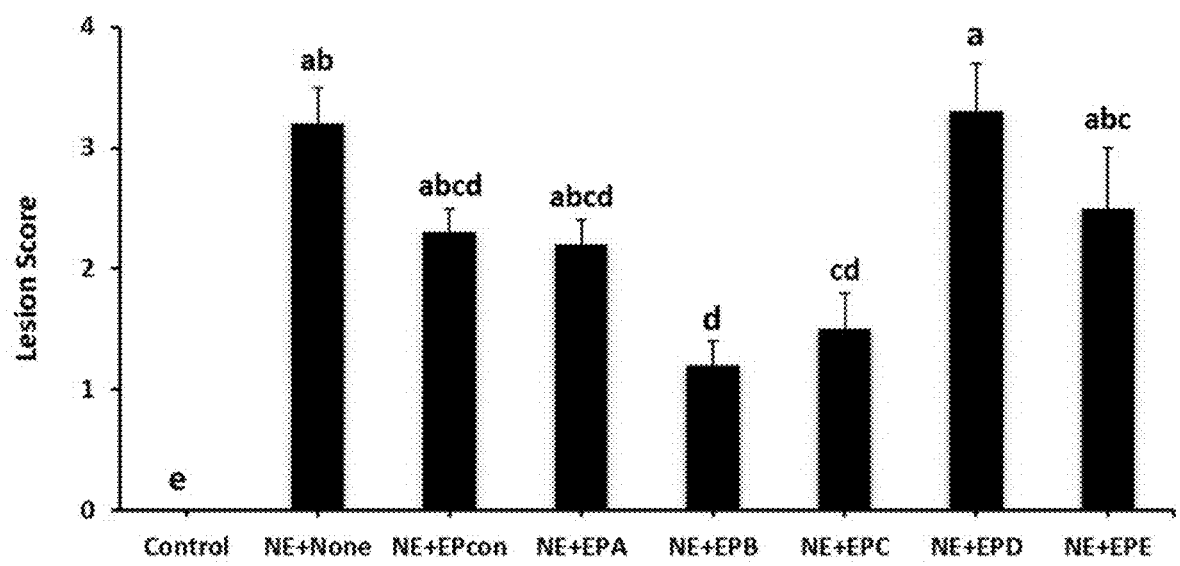

FIG. 19 shows the effect of dietary egg powder IgY supplementation on lesion scores following necrotic enteritis challenge in broilers. Chickens were fed with a non-supplemented diet (control, NE+None) or a diet supplemented with egg powder (EP) at 1% level from 17 days of age to the end of the experimental period. At 17 d post-hatch, birds were uninfected (control) or orally infected with $1\times10^4$ sporulated oocysts of *E. maxima* followed by oral inoculation with $1\times10^9$ CFU of *Clostridium perfringens* at 21 days post-hatch (all necrotic enteritis groups). Intestinal sections were collected on d 23 (2 d post-*Clostridium perfringens* infection) and scored for necrotic enteritis lesions on a scale of 0 (none) to 4 (high) in a blind fashioned way by three independent observers. Values are means with their standard errors represented by vertical bars (n=3). Treatment means with no common letter differ significantly (P≤0.05). EPA=*Clostridium perfringens* α-toxin; EPB=*Clostridium perfringens* elongation factor Tu; EPC=*Clostridium perfringens* necrotic enteritis B-like (NetB) toxin; EPD=*Clostridium perfringens* Pyruvate: Ferredoxin oxidoreductase (PFO); EPE=EPA+EPB+EPC+EPD; EPcon=egg powder from uninfected birds.

Figure 20:
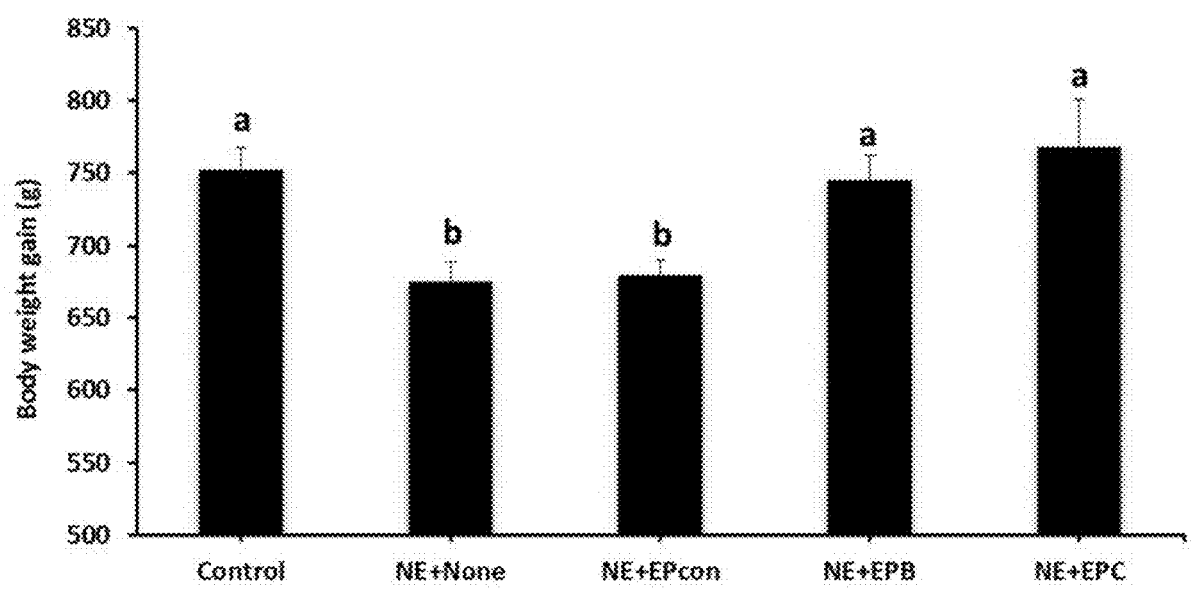

FIG. 20 shows the effect of dietary egg powder IgY supplementation on body weight gain following NE challenge in broilers. Chickens were fed with a non-supplemented diet (control, NE+None) or a diet supplemented with egg powder from uninfected birds (EPcon), from birds infected with *Clostridium perfringens* elongation factor Tu (EPB), or from birds infected with *Clostridium perfringens* necrotic enteritis B-like (NetB) toxin (EPC) at 1% level from 17 days of age to the end of the experimental period. At 17 d post-hatch, birds were uninfected (control) or orally infected with $1\times10^4$ sporulated oocysts of *E. maxima* followed by oral inoculation with $1\times10^9$ CFU of *Clostridium perfringens* at 21 days post-hatch (all NE groups). Body weights were measured at d 17 and d 30 (11 d interval) and weight gains were calculated. Values are means with their standard errors represented by vertical bars (n=10). Treatment means with no common letter differ significantly (P≤0.05).

Figure 21:
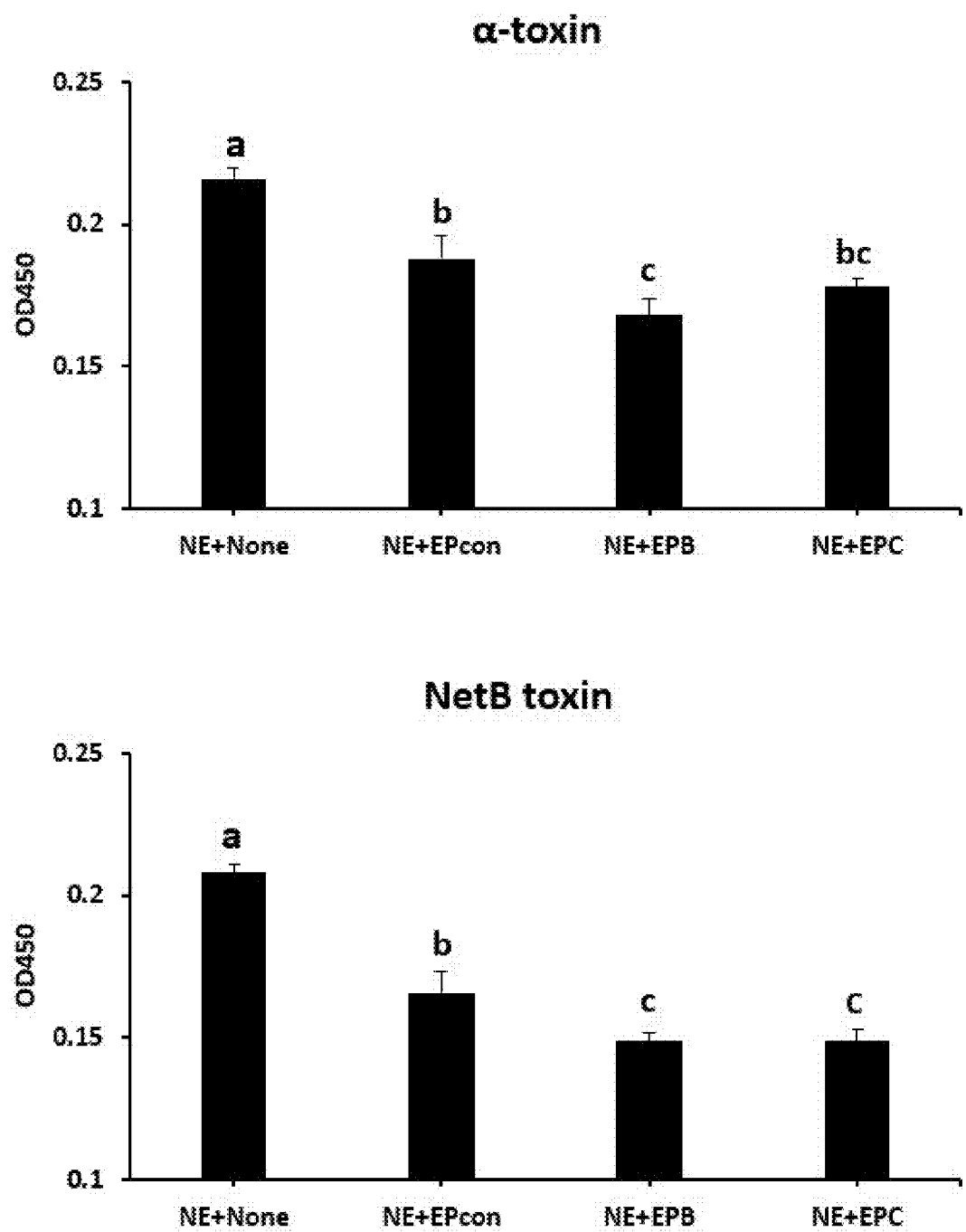

FIG. 21 shows the effect of dietary egg powder IgY supplementation on the levels of serum ca-toxin and NetB toxin. Chickens were fed with a non-supplemented diet (control, NE+None) or a diet supplemented with egg powder from uninfected birds (EPcon), from birds infected with *Clostridium perfringens* elongation factor Tu (EPB), or from birds infected with *Clostridium perfringens* necrotic enteritis B-like (NetB) toxin (EPC) at 1% level from 17 days of age to the end of the experimental period. At 17 d post-hatch, birds were uninfected (control) or orally infected with $1\times10^4$ sporulated oocysts of *E. maxima* followed by oral inoculation with $1\times10^9$ CFU of *Clostridium perfringens* at 21 days post-hatch (all NE groups). Sera samples were collected 6 hr after *Clostridium perfringens* infection and used to measure toxin levels by ELISA. Values are means with their standard errors represented by vertical bars (n=3). Treatment means with no common letter differ significantly (P≤0.05).

Figure 22:
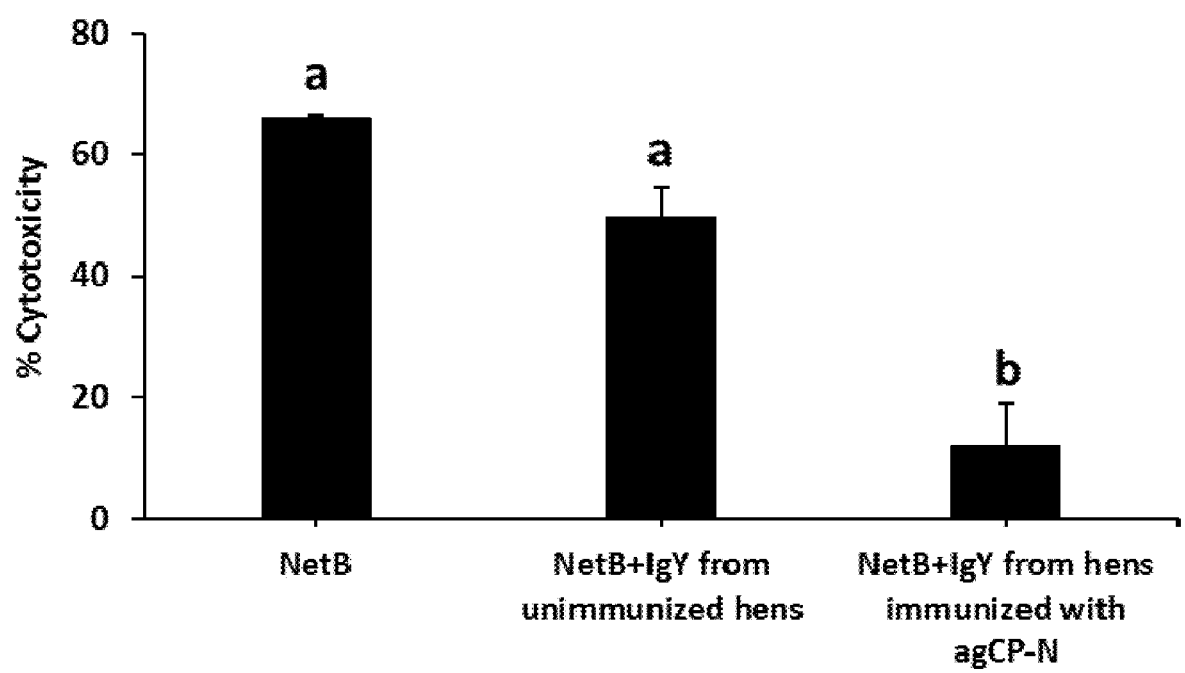

FIG. 22 shows toxin neutralization activity of hyperimmune IgY raised against *Clostridium perfringens* necrotic enteritis B-like (NetB) toxin (agCP-N) in laying hens. IgY from control hens and hyperimmunized hens were incubated with recombinant NetB toxin for 1 hr at RT. IgY-toxin mixtures and toxin alone were added to LMH cells (grown in 96 well microtiter plates) in triplicate wells and incubated for 4 hrs at 37° C. and 5% CO2. % cytotoxicity was measured using a CCK-8 kit (Dojindo).

Figure 23:
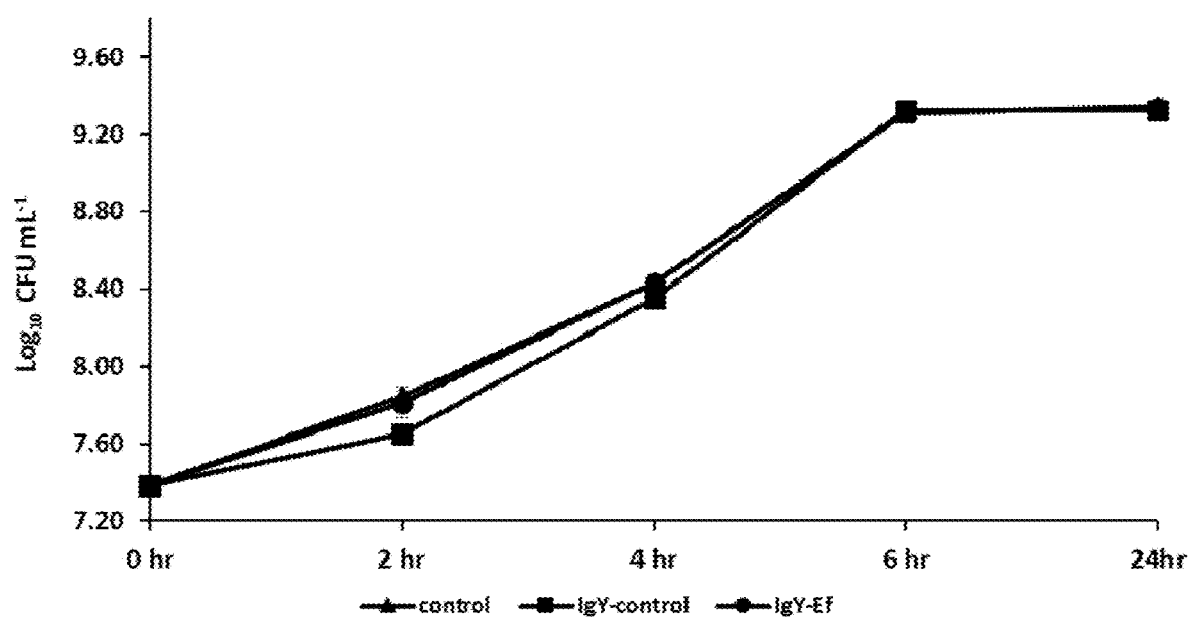

FIG. 23 shows growth curves of *Clostridium perfringens* Del-1 strain in the presence of 1 mg/mL conc. of IgY antibodies from unimmunized hens or hens hyperimmunized with *Clostridium perfringens* elongation factor Tu (agCP-E).

Figure 24:
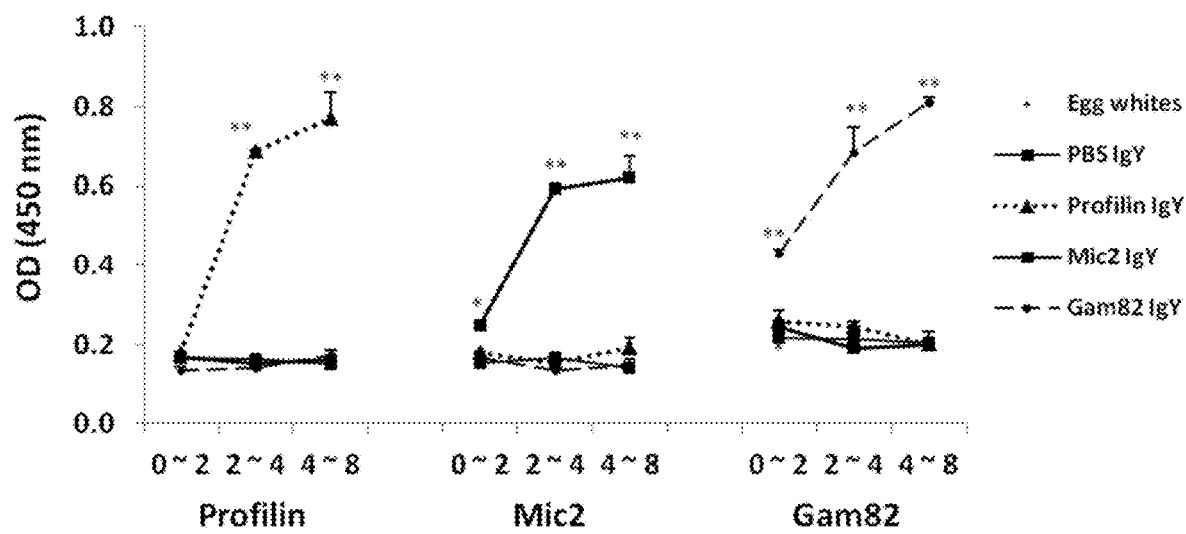

FIG. 24 shows antigen-specific IgY Ab titers against 3 different recombinant *Eimeria* proteins, profilin, MIC2, and Gam82. An ELISA plate was coated with one of recombinant profilin, MIC2, or Gam82 protein (0.2 ug/well) and incubated overnight. Each egg powder collected from the eggs of hens immunized with PBS which is used for protein solvent, profilin, MIC2, or Gam82 protein and harvested at 0-2, 2-4, and 4-8 weeks post immunization was solubilized in PBS buffer (1 mg/10 ml) and used at 25 ug/well on the 96 well ELISA plate coated with profilin, MIC2, or Gam82 protein. Antigen-specific IgY Ab titers were measured against 3 different recombinant *Eimeria* proteins, profilin, MIC2, and Gam82 at 450 nm using ELISA plate reader.

Figure 25:
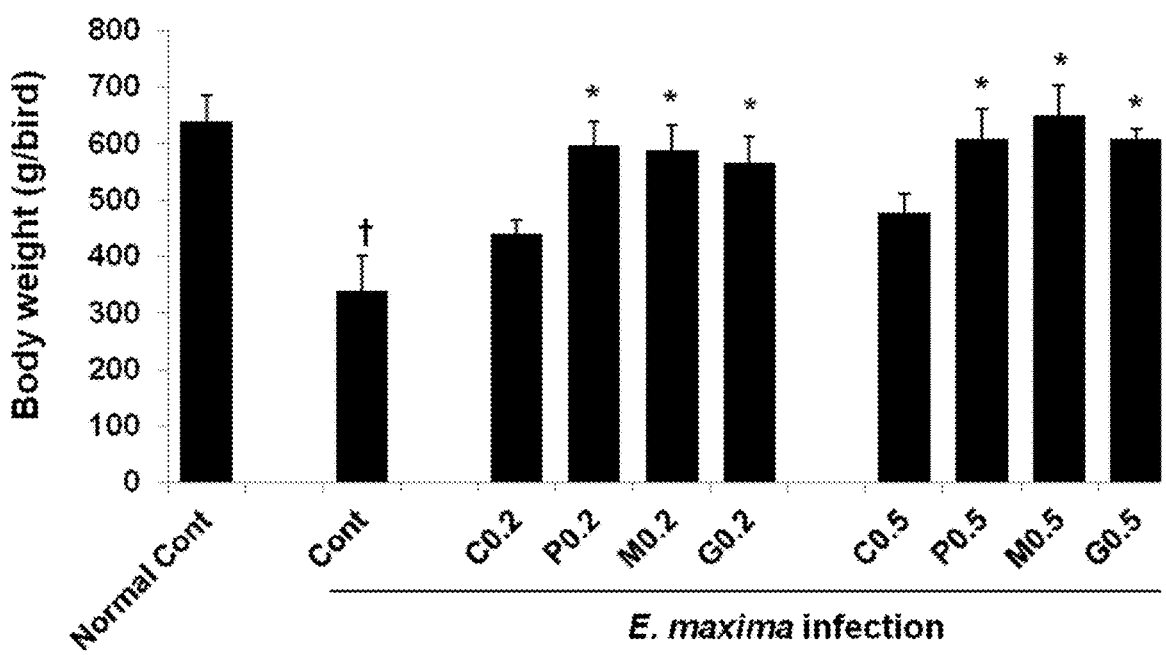

FIG. 25 shows the effect of oral hyperimmune IgY antibodies against profilin, MIC2, and Gam82 on body weight of birds infected with *E. maxima*. One-day-old broiler chickens were fed a standard diet supplemented with the Control without any egg powder, 0.2% and 0.5% egg powders (C0.2, C0.5) from PBS-treated hens, 0.2% and 0.5% egg powders (P0.2, P0.5) from profilin-treated hens, 0.2% and 0.5% egg powders (M0.2, M0.5) from MIC2-treated hens, or 0.2% and 0.5% egg powders (G0.2, G0.5) (v/v) from Gam82-treated hens. The chickens were uninfected (Control) or were orally infected with $5 \times 10^3$ sporulated oocysts of *E. maxima* at 7 days post-hatch, and body weight at 10 days post infection were measured. Each bar represents the mean±SEM values (N=10). †, $p<0.05$ compared with the uninfected normal control; *, $p<0.05$ compared with the infected control according to the T-test.

Figure 26:
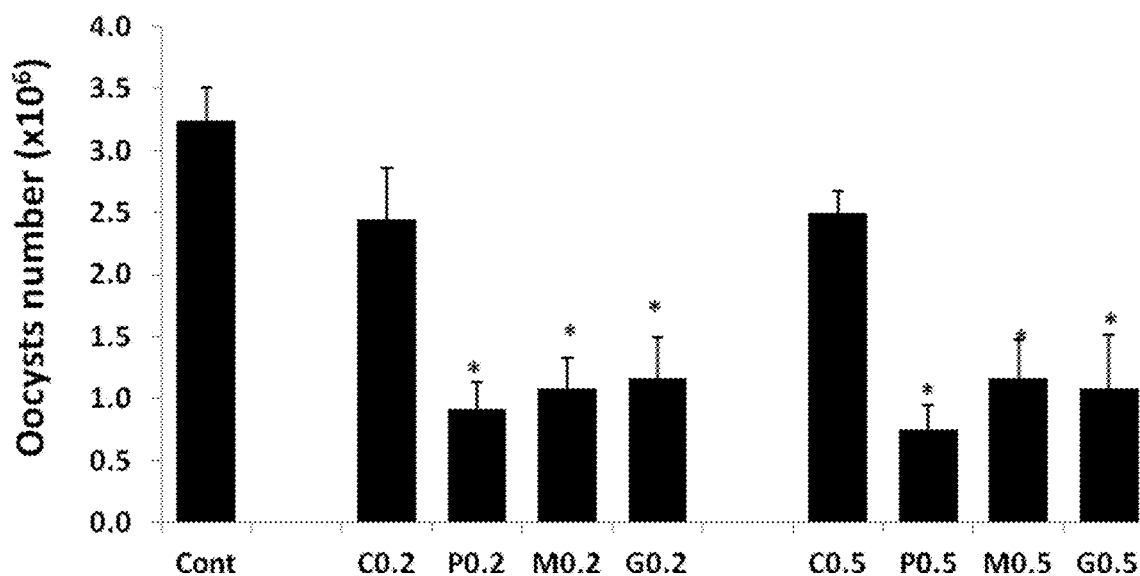

FIG. 26 shows the effect of oral hyperimmune IgY antibodies on oocysts shedding in birds infected with *E. maxima*. One-day-old broiler chickens were fed a standard diet supplemented with the Control without any egg powder, 0.2% and 0.5% egg powders (C0.2, C0.5) from PBS-treated hens, 0.2% and 0.5% egg powders (P0.2, P0.5) from profilin-treated hens, 0.2% and 0.5% egg powders (M0.2, M0.5) from MIC2-treated hens, or 0.2% and 0.5% egg powders (G0.2, G0.5) (v/v) from Gam82-treated hens. The chickens were uninfected (Control) or were orally infected with $5 \times 10^3$ sporulated oocysts of *E. maxima* at 7 days post-hatch, and fecal oocyst shedding between 5 and 10 dpi were measured. Each bar represents the mean±SEM values (N=10). *, $p<0.05$ compared with the infected control according to the T-test.

Figure 27:
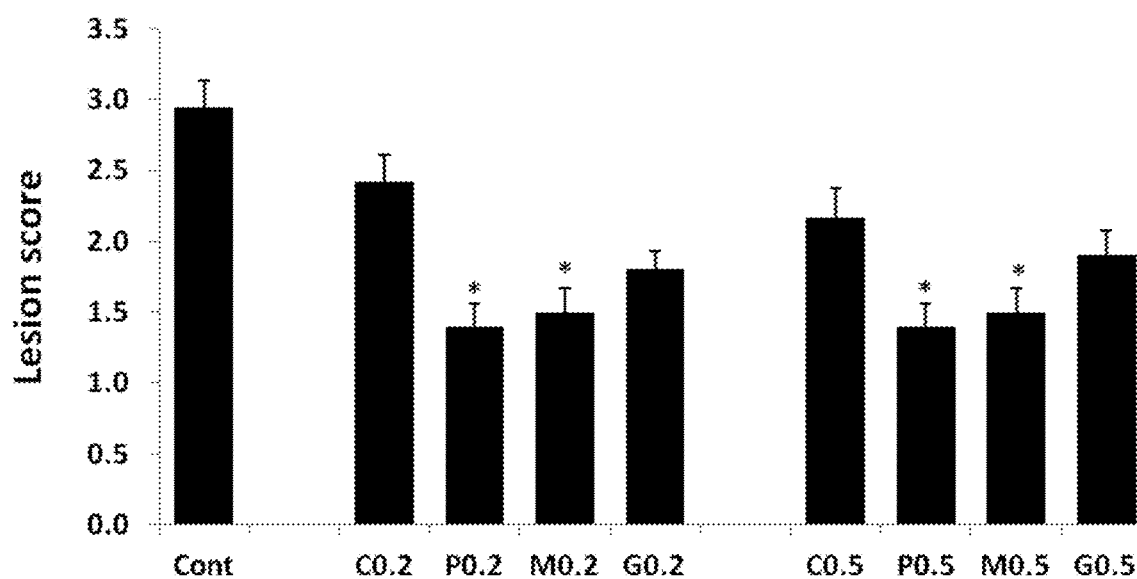

FIG. 27 shows the effect of oral hyperimmune IgY antibodies on lesion score in birds infected with *E. maxima*. One-day-old broiler chickens were fed a standard diet supplemented with the Control without any egg powder, 0.2% and 0.5% egg powders (C0.2, C0.5) from PBS-treated hens, 0.2% and 0.5% egg powders (P0.2, P0.5) from profilin-treated hens, 0.2% and 0.5% egg powders (M0.2, M0.5) from MIC2-treated hens, or 0.2% and 0.5% egg powders (G0.2, G0.5) (v/v) from Gam82-treated hens. The chickens were uninfected (Control) or were orally infected with $5 \times 10^3$ sporulated oocysts of *E. maxima* at 7 days post-hatch, and gut lesion scores were determined at 7 days post infection. Each bar represents the mean±SEM values (N=5). *, $p<0.05$ compared with the infected control according to the T-test.

Figure 28:
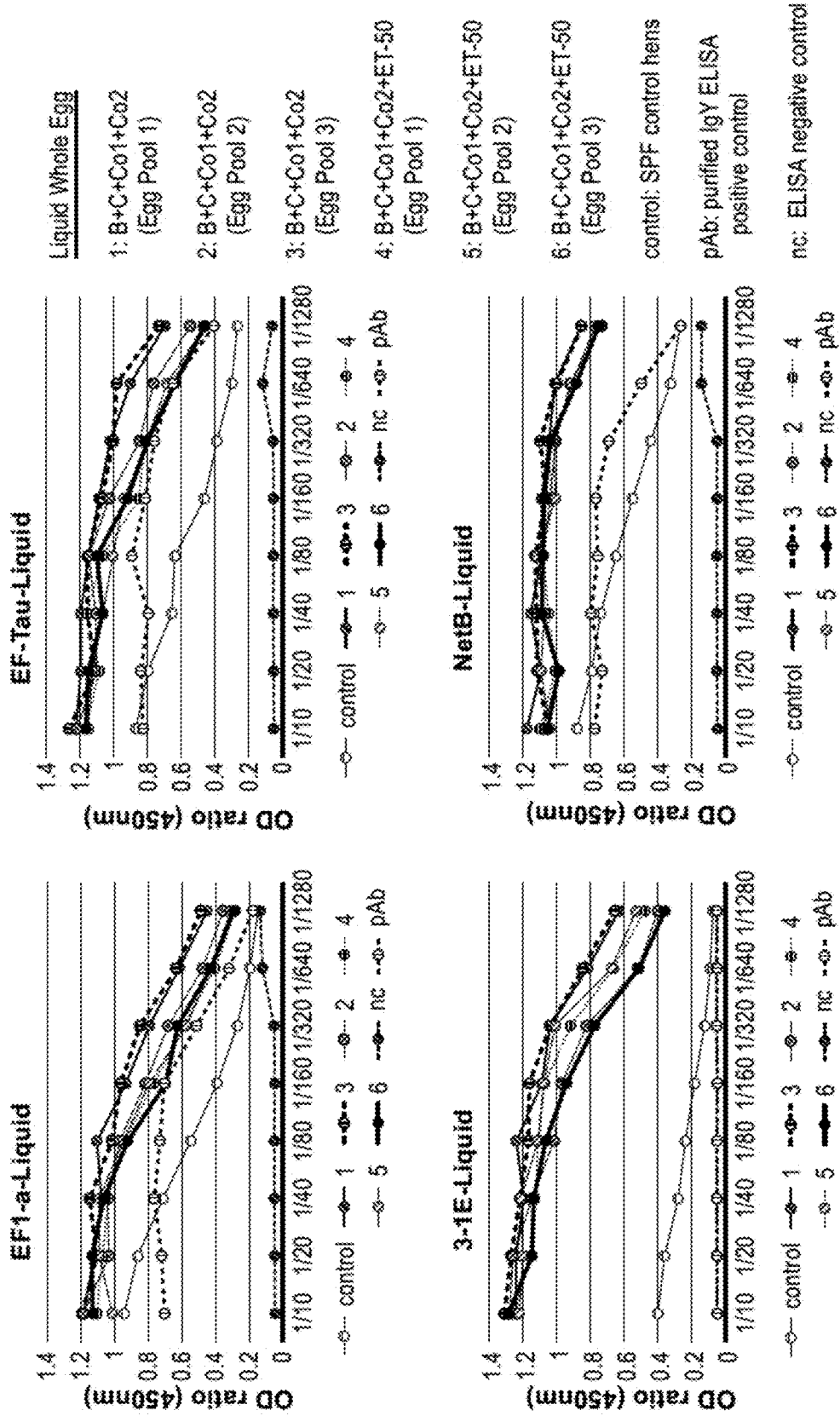

FIG. 28 shows titers of IgY antibodies to antigen B (EF-Tau), C (NetB), Co1 (EF1-a) or Co2 (3-1E) in liquid egg samples from hyperimmunized (treatment Groups 1-6) and non-hyperimmunized (control, specific pathogen free (SPF) hens. Hens in treatment groups 1-3 were hyperimmunized with antigens B, C, Co1 and Co2, and hens in treatment groups 4-6 were hyperimmunized with antigens B, C, Co1, Co2 and ET-50 as described in Example 9. IgY antibody titers were determined in serial dilutions of the samples by ELISA. pAb samples were purified IgY samples containing IgY antibodies to the antigen of interest; nc samples were a negative control for the ELISA assay containing only buffer. Eggs for each hyperimmunized treatment group were collected over a ten day period and pooled on three different days, designated as Egg Pool 1, Egg Pool 2, and Egg Pool 3.

Figure 29:
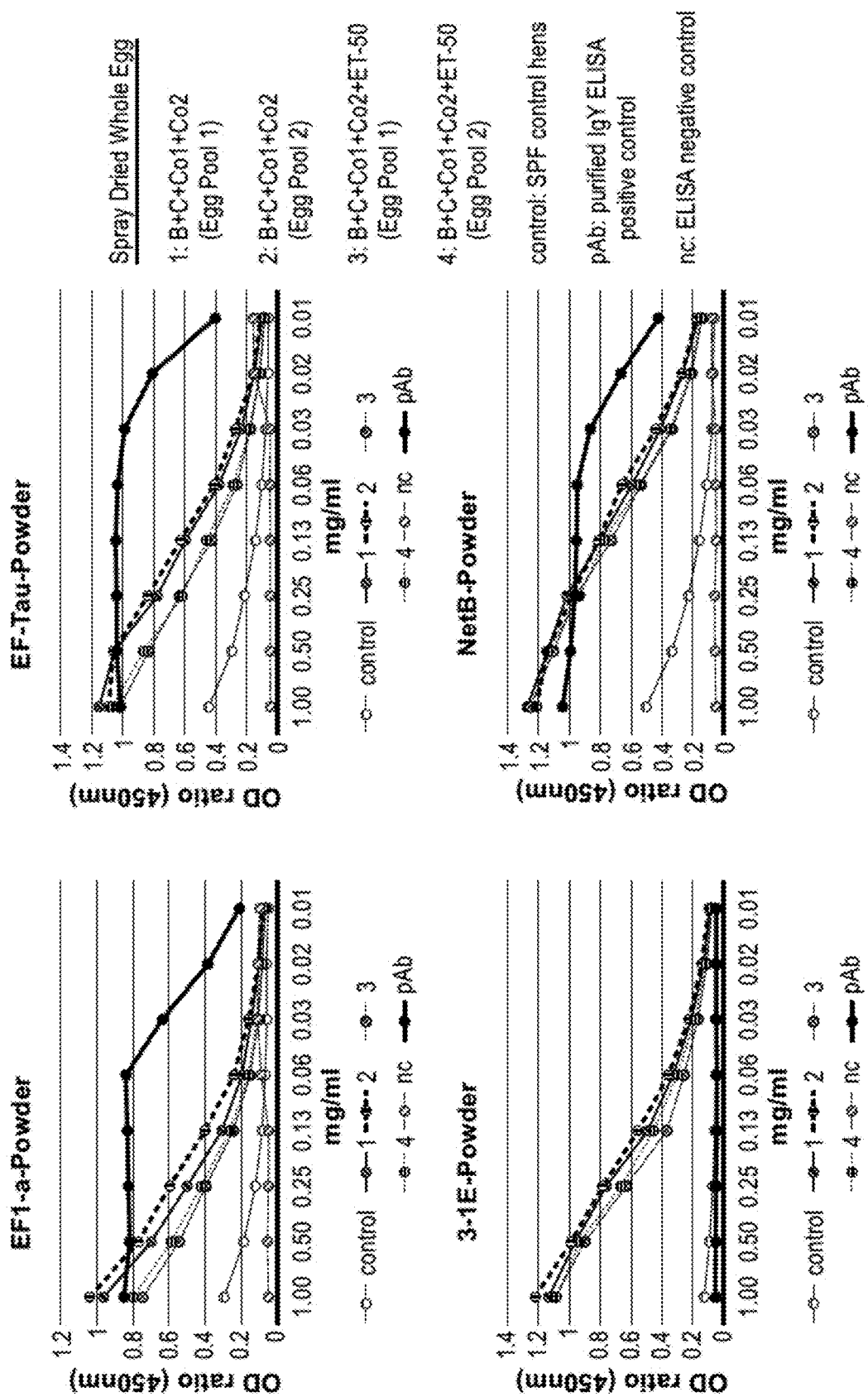

FIG. 29 shows titers of IgY antibodies to antigen B (EF-Tau), C (NetB), Co1 (EF1-a) or Co2 (3-1E) in spray dried egg samples from hyperimmunized (treatment Groups 1-6) and non-hyperimmunized (control, specific pathogen free (SPF) hens. Hens in treatment groups 1-2 were hyperimmunized with antigens B, C, Co1 and Co2, and hens in treatment groups 3-4 were hyperimmunized with antigens B, C, Co1, Co2 and ET-50 as described in Example 9. IgY antibody titers were determined in serial dilutions of the samples by ELISA. pAb samples were purified IgY samples containing IgY antibodies to the antigen of interest; nc samples were a negative control for the ELISA assay containing only buffer. Eggs for each hyperimmunized treatment group were collected over a ten day period and pooled on two different days, designated as Egg Pool 1 and Egg Pool 2.

DETAILED DESCRIPTION AND PREFERRED EMBODIMENTS

The term "hyperimmunization" means exposure to one or more antigens such that an immune response is elevated and maintained above the natural unexposed state.

A "hyperimmune state" refers to an elevated immune response in an egg producing animal that has been hyperimmunized.

The term "egg" as used herein refers to a whole egg (table, hyperimmunized or otherwise). The term "egg product" as used herein refers to a whole egg or any product or fraction obtained from a whole egg. In a particular embodiment, the egg product is an egg yolk, for example, an egg yolk powder. In another embodiment, the egg product is an egg white, for example, an egg white powder. In another embodiment, the egg product is obtained from a whole egg, for example, a whole egg powder (e.g. a spray-dried whole egg powder).

The term "control egg" refers to an egg obtained from an egg-producing that is not maintained in a hyperimmunized state, i.e. an animal that has not been hyperimmunized. The term "control egg product" refers to a control egg or an egg product obtained from a control egg.

The term "hyperimmunized egg" refers to a whole egg obtained from an egg-producing animal maintained in a hyperimmune state, i.e. an egg-producing animal that has been hyperimmunized. The term "hyperimmunized egg product" refers to a hyperimmunized egg or any product obtained from a hyperimmunized egg.

In certain embodiments, the hyperimmunized egg product is a concentrate. As used herein the term "concentrate" refers to a hyperimmunized egg product that is at least partially purified, such that the concentration of antibodies in the concentrate is greater than the concentration of antibodies in a hyperimmunized egg.

In some embodiments, the hyperimmunized egg product is an aqueous IgY concentrate. The term "aqueous IgY concentrate" as used herein refers to an aqueous solution comprising IgY antibodies isolated from a hyperimmunized egg, wherein the concentration of IgY antibodies in the aqueous solution is higher than the concentration of antibodies in the hyperimmunized egg.

The term "egg powder" refers to a whole egg that has been dried. In some embodiments, the egg powder is spray-dried.

The term "egg-producing animal" means any oviparous animal, and includes any animal that lays an egg, such as avians, fish and reptiles.

The term "avian" refers to an animal that is a member of the class Aves. Avians include, but are not limited to, chickens, turkeys, geese, ducks, pheasants, quail, pigeons and ostriches.

The term "supranormal levels" means levels in excess of those found in eggs of egg-producing animals that are not hyperimmunized. For example, supranormal levels of an antibody to a particular antigen are levels of the antibody in excess of those found in eggs of egg-producing animals that are not hyperimmunized with the particular antigen.

The term "bioengineered antigen" refers to an antigen which is obtained through the process of gene cloning technologies and genetic manipulation which allow the preparation of proteins that have antigenic properties.

The term "genetic vaccine" refers to a nucleic acid vaccine which is generally produced by recombinant technologies and which may elicit an immune response.

The term "administer" means any method of providing a subject with a substance, including orally, intranasally, parenterally (intravenously, intramuscularly, or subcutaneously), rectally, topically or intraocularly.

The term "antigen" refers to a substance that is able to induce a humoral antibody and/or cell-mediated immune response rather than immunological tolerance. The term signifies the ability to stimulate an immune response as well as react with the products of it, e.g., an antibody.

In certain embodiments the antigen is an isolated antigen, i.e. an antigen that is at least partially purified from the cell in which it was produced.

As used herein, "nanoparticle" refers to a particle or a structure in the nanometer (nm) range, typically from about 1 to about 1000 nm in diameter.

As used herein, a "microparticle" is a particle of a relatively small size, but not necessarily in the micron size range; the term is used in reference to particles of sizes that can be, for example 1 to about 1000 microns. The term "microparticle" encompasses microspheres, microcapsules and microparticles, unless specified otherwise. A microparticle may be of composite construction and is not necessarily a pure substance; it may be spherical or any other shape.

As used herein, an "antibody" is a protein that includes at least one complementary determining region that binds to a specific target antigen, e.g. antigen A, B, C, D, Co1, Co2, H, or ET-50 disclosed herein. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. In a particular embodiment, the antibody is a polyclonal antibody. The term "polyclonal antibody", as used herein, refers to a population of antibody molecules that that are capable of immunoreacting with different epitopes on a particular antigen. In a particular embodiment, the antibody is an IgY antibody.

Necrotic Enteritis

Necrotic enteritis (NE), caused by *Clostridium perfringens*, is a widespread infectious disease causing great economic impairment to the poultry industry worldwide. *Clostridium perfringens* is a Gram-positive anaerobic bacterium found in soil, chicken litter, and at low levels in the intestine of healthy birds. The species, *Clostridium perfringens*, can be subdivided into subspecies. Five subspecies have been described. All subspecies produce several toxins, both major and minor toxins. A range of minor toxins is produced by all *C. perfringens* types. One or more of these various toxins can play a role in *C. perfringens* related pathogenesis.

*C. perfringens*-associated necrotic enteritis usually occurs in broiler chickens at 2-6 weeks of age and may present as acute clinical disease or subclinical infection. Acute infections are characterized by sudden onset of mortality with very few clinical signs. Subclinical necrotic enteritis causes reduced growth, increased feed conversion ratio, which were estimated to be 12% and 10.9% respectively compared to healthy birds, and contributes to the major portion of economic losses caused by necrotic enteritis (Skinner et al., 2010, Avian Dis. 54:1237-1240). A variety of predisposing factors, such as diets containing wheat and barley, poorly digestible protein, and coccidial co-infection, are required for *Clostridium perfringens* to multiply and infect poultry (Van Immerseel et al., 2004, Avian Pathol 33: 537-549; and Timbermont et al., 2009, Comp Immunol Microbiol 32: 503-512).

Hyperimmunized Egg Product

Egg-producing animals produce antibodies in blood and eggs that are specific to particular immunogens. For example, various genera of the class Aves, such as chickens (*Gallus domesticus*), turkeys, and ducks produce antibodies against antigens associated with avian diseases. LeBacq-Verheyden et al. (Immunology 27:683 (1974)) and Leslie, G. A., et al. (J. Med. 130:1337 (1969)), have quantitatively analyzed immunoglobulins of the chicken. Polson, A., et al. (Immunological Communications 9:495-514 (1980)) immunized hens against several proteins and natural mixtures of proteins, and detected IgY antibodies in the yolks of the eggs. Fertel, R., et al. (Biochemical and Biophysical Research Communications 102:1028-1033 (1981)) immunized hens against prostaglandins and detected antibodies in the egg yolk. Jensenius et al. (Journal of Immunological Methods 46:63-68 (1981)) provide a method of isolating egg yolk IgG for use in immunodiagnostics. Polson et al. (Immunological Communications 9:475-493 (1980)) describe antibodies isolated from the yolk of hens that were immunized with a variety of plant viruses.

U.S. Pat. No. 4,748,018 discloses a method of passive immunization of a mammal that comprises parenterally administering purified antibody obtained from the eggs of an avian that has been immunized against the corresponding antigen, and wherein the mammal has acquired immunity to the eggs.

U.S. Pat. No. 5,772,999, assigned to DCV-Biologics, discloses a method of preventing, countering or reducing chronic gastrointestinal disorders or Non-Steroidal Anti-Inflammatory Drug-induced (NSAID-induced) gastrointestinal damage in a subject by administering hyperimmunized egg and/or milk or fractions thereof to the subject.

An immunized egg is an egg which comes from an avian which has been immunized with, for example, a specific antigen or mixture of antigens. A hyperimmunized egg is an egg which comes from an avian which has been brought to a specific state of immunization by means of, for example, periodic booster administrations of antigens. Hyperimmunized eggs, no matter the type of antigen their avian maker has been administered, have been found to have various beneficial factors, including, as mentioned above, the treatment of chronic gastrointestinal disorders, NSAID-induced gastrointestinal damage (see U.S. Pat. No. 5,772,999) and anti-inflammatory effects due to the presence of an anti-inflammatory composition (see U.S. Application Publication No. US 2004/0156857).

Control eggs, i.e. from egg producing animals that are not maintained in a hyperimmune state, may also contain antibodies against *C. perfringens* or *E. tenella* antigens, since many egg-producing animals are naturally exposed to these pathogens. However, one of the advantages of the hyperimmunized egg product is that it would have a higher and more consistent level of antibodies (e.g. IgY antibodies) to particular *C. perfringens* and/or *E. tenella* antigens compared to a control egg product.

The hyperimmunized egg product can be produced by any egg-producing animal. It is preferred that the animal be a member of the class Aves or, in other words, an avian. Within the class Aves, domesticated fowl are preferred, but other members of this class, such as turkeys, ducks, and geese, are a suitable source of hyperimmune egg product. In a particular embodiment, the egg-producing animal is a chicken.

This special state of hyperimmunization is preferably achieved by administering an initial immunization, followed by periodic boosters with sufficiently high doses of specific antigens or mixtures of antigens. The dosage of the booster may be 10%, 20%, 30%, 40%, 50%, 60%, 70%, 80%, 90% or 100% of the dosage necessary to produce primary immunization of the egg-producing animal. Any of these percentages may be used to define a range for the dosage of the booster immunization. For example, in some embodiments, the dosage of the booster is 20%-80%, 30%-70%, or 50%-100% of the dosage necessary to produce primary immunization of the egg-producing animal. In a particular embodiment, the dosage of the booster immunization is 50% of the dosage of the primary immunization.

Having knowledge of the requirement for developing and maintaining a hyperimmune state, it is within the skill of the art to vary the amount of antigen administered, depending on the egg-producing animal genera and strain employed, in order to maintain the animal in the hyperimmune state.

The hyperimmune state may be produced by a single antigen or a combination of antigens. Hyperimmunization may be achieved by multiple exposures to multiple antigens, or multiple exposures to a single antigen.

In certain embodiments, the antigen is a protein, for example a purified recombinant protein. Alternative modes of hyperimmunizing egg producing animals can be used in place of antigenic proteins, and include the use of genetic vaccines. In particular, any DNA construct (generally consisting of a promoter region and an antigen encoding sequence) will trigger an immune response. Genetic vaccines include immunogenic-coding vectors, fragments of naked DNA, plasmid DNA, DNA-RNA immunogens, DNA-protein conjugates, DNA-liposome conjugates, DNA expression libraries, and viral and bacterial DNA delivered to produce an immune response. Methods of DNA delivery include particle bombardment, direct injection, viral vectors, liposomes and jet injection, among others. When applying these delivery methods, much smaller quantities may be necessary and generally result in more persistent antigen production. When using such genetic processes, the preferred method for introducing DNA into avians is through intramuscular injection of the DNA into the breast muscle.

Methods of DNA delivery include but are not limited to, particle bombardment, direct injection, liposomes, and jet injection (Fynan, E. F. et al., Proc. Natl. Acad. Sci. USA 90:11478-11482 (1993)). The nucleic acids that code for an antigen, promoter regions (notably CMV cauliflower mosaic virus) and SV40 bacterial origin can be replicated in bacteria to produce plasmid DNA for use in DNA injections. Although several routes of parenteral administration of the DNA are effective in chickens, the preferred method is intramuscular injection to the breast muscle. Vaccine trials are carried out in egg laying avians, preferably chickens. Repeated immunizations are given at one to two week intervals for up to six months.

It is preferred that the amounts of DNA used are generally in the order of 50-300 ag of DNA in saline for direct injection. For particle bombardment, 4-100 ag of DNA co-precipitated onto gold beads by the addition of 2.5 M $CaCl_2$ are preferred. Repeated immunizations can be given intradermally by this method of accelerating DNA coated particles into the live animal.

Antigens for Hyperimmunization

In certain embodiments, the antigen for hyperimmunization comprises a protein, e.g. one or more of the proteins listed in Table 1A below. For example, in certain embodiments, the antigen used for preparation of the hyperimmunized egg product is selected from the group consisting of the antigens listed in Table 1A below, i.e. antigens A, B, C, D, Co1 and Co2. In some embodiments, the egg producing animal is hyperimmunized with a single antigen, e.g. A, B, C, D, Co1 or Co2. In some embodiments, the egg producing animal is hyperimmunized with two or more antigens selected from the antigens A, B, C, D, Co1 or Co2. In a particular embodiment, the egg producing animal is hyperimmunized with at least one *Clostridium* antigen (i.e. antigens A, B, C and D), and at least one *Eimeria* antigen (i.e. antigens Co1 and Co2).

TABLE 1A

*Clostridium* and *Eimeria* Antigens

| Antigen | Description |
|---|---|
| A | *Clostridium perfringens* α-toxin, a zinc metalloenzyme phospholipase C sphingomyelinase (Genbank Accession No. KY584046; SEQ ID NO: 1) |
| B | *Clostridium perfringens* elongation factor Tu (EF-Tu), a component of prokaryotic mRNA translation apparatus (Genbank Accession No. KY584047; SEQ ID NO: 3) |
| C | *Clostridium perfringens* necrotic enteritis B-like (NetB) toxin, a pore-forming toxin (Genbank Accession No. KY559052; SEQ ID NO: 5) |
| D | *Clostridium perfringens* Pyruvate: Ferredoxin oxidoreductase (PFO), a metabolic enzyme that catalyzes pyruvate to acetyl-CoA (Genbank Accession No. KY584048; SEQ ID NO: 7) |
| Co1 | *Eimeria tenella* elongation factor 1-alpha, transfers amino-acylated tRNAs to the ribosome A site in a GTP-dependent reaction (Genbank Accession No. KX900609; SEQ ID NO: 9) |
| Co2 | *Eimeria tenella* 3-1E profilin, a highly conserved apicomplexan ligand for toll-like receptors (Genbank Accession No. AF113613.2; SEQ ID NO: 11) |

*Clostridium perfringens* α-toxin (Antigen A), a zinc metalloenzyme phospholipase C sphingomyelinase, has been considered as the major virulence factor in the pathogenesis of necrotic enteritis in chickens for more than 20 years (Van Immerseel et al., 2009, Trends Microbiol. 17:32-36). However, Keyburn et al. (2006, Infect. Immun. 74:6496-6500) demonstrated that α-toxin is not essential for producing necrotic enteritis and later identified and described a new pore-forming toxin NetB (necrotic enteritis B-like) (Antigen C) associated with necrotic enteritis in broilers (Keyburn et al., 2008, PLOS Pathog. 4(2):e26). Recently, Lee et al. (2011, Res. Vet. Sci. 91:e80-86) identified two more non-toxin *Clostridium perfringens* proteins, elongation factor Tu (EF-Tu, Antigen B) and Pyruvate: Ferredoxin oxidoreductase (PFO, Antigen D) that were shown to be immunogenic in chickens. EF-Tu is a component of prokaryotic mRNA translation apparatus and has a role in elongation cycle of protein synthesis (Schirmer et al., 2002, Appl. Environ. Microbiol. 68:4894-4899). PFO is a metabolic enzyme that catalyzes pyruvate to acetyl-CoA (Charon et al., 1999, Curr. Opin. Struc. Biol. 9:663-669).

Elongation factor 1-alpha (EF-1α, Antigen Co1) transfers amino-acylated tRNAs to the ribosome A site in a GTP-dependent reaction. (Riis, B., et al., 1990, Trends Biochem. Sci. 15, 420-424). In addition, EF-1α appears to have a number of other functions associated with cell growth, motility, protein turnover, and signal transduction, DNA replication/repair protein networks, and apoptosis. Previous studies have demonstrated that EF-1α can be bound by actin filaments or microtubules as one function. In particular, EF-1α was reported to be a cytoskeleton-binding protein and to play a role in regulating the assembly and crosslinking of actin filaments and microtubules. Studies of EF-1α from *Cryptosporidium parvum* suggest that EF-1α associates with the cytoskeleton at the apical region, forming an essential component of the parasite's invasion apparatus. Sasai, K., et al., 1996, J. Parasitol. 82, 82-87; and Matsubayashi et al., 2013, J Biol. Chem. 288(47): 34111-20.

Profilin is an actin-binding protein involved in the dynamic turnover and restructuring of the actin cytoskeleton. It is found in all eukaryotic organisms in most cells. In apicomplexan protozoa, such as *Eimeria, Plasmodium*, and *Toxoplasma*, profilin is a key contributor to actin-dependent gliding motility that is essential for migration across biological barriers and host cell invasion. *Eimeria tenella* 3-1E profilin is a highly conserved apicomplexan ligand for toll-like receptors. Jang et al., 2011, Experimental Parasitology 127 (2011) 178-183.

In certain embodiments, the *Clostridium perfringens* α-toxin antigen (Antigen A) comprises the amino acid sequence of SEQ ID NO: 1. In a particular embodiment, the *Clostridium perfringens* α-toxin antigen consists of the amino acid sequence of SEQ ID NO: 1. In some embodiments, the *Clostridium perfringens* α-toxin antigen comprises an amino acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 1.

In certain embodiments, the *Clostridium perfringens* elongation factor Tu (EF-Tu) antigen (Antigen B) comprises the amino acid sequence of SEQ ID NO: 3. In a particular embodiment, the *Clostridium perfringens* elongation factor Tu (EF-Tu) antigen consists of the amino acid sequence of SEQ ID NO: 3. In some embodiments, the *Clostridium perfringens* elongation factor Tu (EF-Tu) antigen comprises an amino acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 3.

In certain embodiments, the *Clostridium perfringens* necrotic enteritis B-like (NetB) toxin antigen (Antigen C) comprises the amino acid sequence of SEQ ID NO: 5. In a particular embodiment, the *Clostridium perfringens* necrotic enteritis B-like (NetB) toxin antigen consists of the amino acid sequence of SEQ ID NO: 5. In some embodiments, the *Clostridium perfringens* necrotic enteritis B-like (NetB) toxin antigen comprises an amino acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 5.

In certain embodiments, the *Clostridium perfringens* Pyruvate: Ferredoxin oxidoreductase (PFO) antigen (Antigen D) comprises the amino acid sequence of SEQ ID NO: 7. In a particular embodiment, the *Clostridium perfringens* Pyruvate: Ferredoxin oxidoreductase (PFO) antigen consists of the amino acid sequence of SEQ ID NO: 7. In some embodiments, the *Clostridium perfringens* Pyruvate: Ferredoxin oxidoreductase (PFO) antigen comprises an amino acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 7.

In certain embodiments, the *Eimeria tenella* elongation factor 1-alpha antigen (Antigen Co1) comprises the amino acid sequence of SEQ ID NO: 9. In a particular embodiment, the *Eimeria tenella* elongation factor 1-alpha antigen consists of the amino acid sequence of SEQ ID NO: 9. In some embodiments, the *Eimeria tenella* elongation factor 1-alpha antigen comprises an amino acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 9.

In certain embodiments, the *Eimeria tenella* 3-1E profilin antigen (Antigen Co2) comprises the amino acid sequence of SEQ ID NO: 11. In a particular embodiment, the *Eimeria*

*tenella* 3-1E profilin antigen consists of the amino acid sequence of SEQ ID NO: 11. In some embodiments, the *Eimeria tenella* 3-1E profilin antigen comprises an amino acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 11.

As discussed above, an egg-producing animal may be hyperimmunized by administering a genetic vaccine comprising DNA encoding an antigenic protein. In certain embodiments, the genetic vaccine comprises a nucleic acid sequence selected from the group consisting of SEQ ID NO: 2, SEQ ID NO: 4, SEQ ID NO: 6, SEQ ID NO: 8, SEQ ID NO: 10, and SEQ ID NO: 12.

In certain embodiments, the genetic vaccine comprises a nucleic acid sequence encoding *Clostridium perfringens* α-toxin antigen (Antigen A) and having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 2.

In certain embodiments, the genetic vaccine comprises a nucleic acid sequence encoding *Clostridium perfringens* elongation factor Tu (EF-Tu) antigen and having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 4.

In certain embodiments, the genetic vaccine comprises a nucleic acid sequence encoding *Clostridium perfringens* necrotic enteritis B-like (NetB) toxin antigen and having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 6.

In certain embodiments, the genetic vaccine comprises a nucleic acid sequence encoding *Clostridium perfringens* Pyruvate: Ferredoxin oxidoreductase (PFO) antigen and having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 8.

In certain embodiments, the genetic vaccine comprises a nucleic acid sequence encoding *Eimeria tenella* elongation factor 1-alpha antigen and having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 10.

In certain embodiments, the genetic vaccine comprises a nucleic acid sequence encoding the *Eimeria tenella* 3-1E profilin antigen and having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 12.

Various methods and software programs can be used to determine the homology between two or more peptides or nucleic acids, such as NCBI BLAST, Clustal W, MAFFT, Clustal Omega, AlignMe, Praline, or another suitable method or algorithm. In some embodiments, percent identity is calculated by FastDB based upon the following parameters: mismatch penalty of 1; gap penalty of 1; gap size penalty of 0.33; and joining penalty of 30.

An example of a useful algorithm is PILEUP. PILEUP creates a multiple sequence alignment from a group of related sequences using progressive, pairwise alignments. The algorithm can also plot a tree showing the clustering relationships used to create the alignment. A non-limiting example of PILEUP parameters includes a default gap weight of 3.00, a default gap length weight of 0.10, and weighted end gaps.

Another example of a useful algorithm is the BLAST algorithm. A non-limiting example of a BLAST program is the WU-BLAST-2 program. WU-BLAST-2 uses several search parameters, most of which are set, for example, to the default values. The adjustable parameters are set, for example, with the following values: overlap span=1, overlap fraction=0.125, word threshold (T)=ll. The HSP S and HSP S2 parameters are dynamic values and are established by the program itself depending upon the composition of the particular sequence and composition of the particular database against which the sequence of interest is being searched. The values can be adjusted to increase sensitivity.

An additional useful algorithm is gapped BLAST. Gapped BLAST uses BLOSUM-62 substitution scores; threshold T parameter set to 9; the two-hit method to trigger ungapped extensions, charges gap lengths of k a cost of 10+k; Xu set to 16, and Xg set to 40 for database search stage and to 67 for the output stage of the algorithms. Gapped alignments are triggered by a score corresponding to, for example, about 22 bits.

An additional useful tool is Clustal, a series of commonly used computer programs for multiple sequence alignment. Recent versions of Clustal include ClustalW, ClustalX and Clustal Omega. Default parameters for pairwise alignments and calculation of percent identity of protein 5 sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4.

In certain embodiments, the antigen comprises one or more bacteria, for example, one or more of the bacteria listed in Table 1B below. For example, in some embodiments, the antigen is prepared from a bacterial culture containing one or more of the bacteria shown in Table 1B below. In a particular embodiment, the antigen comprises all of the bacteria shown in Table 1B below.

TABLE 1B

| | |
|---|---|
| *Escherichia coli* | *Escherichia coli* (Aerobacter) |
| *Klebsiella pneumoniae* | *Pseudomonas aeruginosa* |
| *Salmonella typhimurium* | *Salmonella dysenteriae* |
| *Salmonella enteriditis* | *Salmonella epidermis* |
| *Salmonella simulans* | *Streptococcus pyogenes*, type 1 |
| *Streptococcus pyogenes*, type 3 | *Streptococcus pyogenes*, type 5 |
| *Streptococcus pyogenes*, type 8 | *Streptococcus pyogenes*, type 12 |
| *Streptococcus pyogenes*, type 14 | *Streptococcus pyogenes*, type 18 |
| *Streptococcus pyogenes*, type 22 | *Pseudomonas vulgaris* |
| *Streptococcus agalactiae* | *Streptococcus mitis* |
| *Streptococcus mutans* | *Streptococcus salavarius* |
| *Streptococcus sanguis* | *Streptococcus pneumoniae* |
| *Propionibacterium acnes* | *Haemophilis influenzae* |

In certain embodiments, the antigen comprises one or more viruses, for example, one or more of the viruses listed in Table 1C below. In a particular embodiment, the antigen comprises the Infectious Bursal Disease Virus, Standard; Infectious Bursal Disease Virus, variant A; Infectious Bursal Disease Virus, variant E; Reovirus strain S1133; Reovirus strain 2408; and Reovirus strain SS412. In a further particular embodiment, the antigen comprises all of the viruses listed in Table 1C. The combination of all of the viruses listed in Table 1C is referred to herein as "Antigen H".

TABLE 1C

Viral Antigens

| Virus | Description | Viral Vaccine |
|---|---|---|
| Infectious Bursal Disease Virus, Standard | | MAXIMUNE ® 6 (Ceva Animal Health, Lenexa, KS) |
| Infectious Bursal Disease Virus, variant A | | MAXIMUNE ® 6 |
| Infectious Bursal Disease Virus, variant E | | MAXIMUNE ® 6 |
| Reovirus strain S1133 | Tenosynovitis pathotype | MAXIMUNE ® 6 |
| Reovirus strain 2408 | Malabsorption pathotype | MAXIMUNE ® 6 |
| Reovirus strain SS412 | Distinct serotype from the S1133 type reovirus and a causative agent of proventriculitis and malabsorption syndrome in broilers | MAXIMUNE ® 6 |

TABLE 1C-continued

Viral Antigens

| Virus | Description | Viral Vaccine |
|---|---|---|
| Infectious Bronchitis Virus | Arkansas type, live virus | AviPro ® IB Ark (Lohman Animal Health Int., Winslow, ME) |
| Hemorrhagic Enteritis (HE) Virus, Avian Adenovirus Type 2 | Pheasant strain, live avirulent strain | Adenomune ® II (Ceva Animal Health, Lenexa, KS) |

Hyperimmunization Procedure

The following list of steps is an example of a preferred procedure used to bring an egg-producing animal to a heightened state of immunity from which the resultant hyperimmune egg or egg product can be administered to an avian:

1. Selecting one or more antigens.
2. Eliciting an immune response in the egg-producing animal by primary immunization.
3. Administering booster vaccines of one or more antigens of appropriate dosage to induce and maintain the hyperimmune state.

Step 1:

The critical point in this step is that the antigen(s) must be capable of inducing immune and hyperimmune states in the egg-producing animal. In some embodiments, the egg-producing animal is immunized with one or more of the antigens listed in Table 1A, Table 1B, or Table 1C.

Step 2:

In some embodiments, the vaccine for immunization of the egg-producing animal comprises a protein antigen, for example, a purified recombinant protein. In some embodiments, the vaccine is a genetic vaccine as described above. For bacterial antigens, the vaccine may be either a killed or live-attenuated vaccine. The vaccine may be administered by any method that elicits an immune response. It is preferred that immunization be accomplished by administering the vaccine through intramuscular injection. The preferred muscle for injection in an avian is the breast muscle. Dosage is preferably 0.05-5 milligrams of the immunogenic vaccine. Other methods of administration that can be used include intravenous injection, intraperitoneal injection, intradermal, rectal suppository, aerosal or oral administration. When DNA techniques are used for the hyperimmunization process, much smaller quantities are required, generally 300 micrograms.

It can be determined whether the vaccine has elicited an immune response in the egg-producing animal through a number of methods known to those having skill in the art of immunology. Examples of these include enzyme-linked immunosorbent assays (ELISA), tests for the presence of antibodies to the stimulating antigens, and tests designed to evaluate the ability of immune cells from the host to respond to the antigen. The minimum dosage of antigen necessary to induce an immune response depends on the vaccination procedure used, including the type of adjuvants and formulation of antigen(s) used as well as the type of egg-producing animal used as the host.

Step 3:

The hyperimmune state is preferably induced and maintained in the target animal by repeated booster administrations of an appropriate dosage at fixed time intervals. The time intervals are preferably 2-8 week intervals over a period of 6-12 months. However, it is essential that the booster administrations do not lead to immune tolerance. Such processes are well known in the art. Methods of preparing the hyperimmunized egg product are described, for example, in U.S. Pat. No. 6,803,035, which is incorporated by reference herein in its entirety.

In a particular embodiment, an antigen (e.g. an antigen listed in Table 1A or Table 1B) is formulated into a Freund's vaccine at a final concentration of 100 µg/ml. In the first vaccination, the egg-producing animal receives two 0.5 ml doses of each antigen, such that the egg-producing animal receives 100 µg of each antigen. For example, if an egg-producing animal is injected with antigens B and C, the animal would receive 100 µg of antigen B and 100 µg of antigen C for the first vaccination. Two weeks later, one 0.5 ml dose (i.e. 50 µg of the antigen) of each antigen is administered to the egg-producing animal as a booster vaccination. An additional booster vaccination is performed 4 weeks after the first vaccination. The vaccines may be administered to breast tissue. In a further embodiment, the egg-producing animal is injected with one or more of the antigens listed in Table 1A or Table 1B and one or more of the viral vaccines listed in Table 1C (i.e. MAXIMUNE® 6, AviPro® IB Ark, and Adenomune® II).

It is possible to use other hyperimmunization maintenance procedures or combination of procedures, such as, for example, intramuscular injection for primary immunization and intravenous injection for booster injections. Further procedures include simultaneously administering microencapsulated and liquid antigen, or intramuscular injection for primary immunization, and booster dosages by oral administration or parenteral administration by microencapsulation means. Several combinations of primary and hyperimmunization are known to those skilled in the art.

In certain embodiments, the hyperimmunized egg product comprises one or more antibodies, each of which is specific to a protein antigen shown in Table 1A, a bacterium shown in Table 1B, or a virus shown in Table 1C. In one embodiment, the hyperimmunized egg product comprises antibodies to at least one of a protein antigen shown in Table 1A, a bacterium shown in Table 1B, or a virus shown in Table 1. In one embodiment, the hyperimmunized egg product comprises all of the bacteria shown in Table 1B. In one embodiment, the hyperimmunized egg product comprises antibodies to all of the viruses shown in Table 1C. In one embodiment, the hyperimmunized egg product comprises antibodies to antigens B and C in Table 1A. In one embodiment, the hyperimmunized egg product comprises antibodies to antigens B, C, Co1 and Co2 in Table 1A. In one embodiment, the hyperimmunized egg product comprises antibodies to antigens B, C, Co1 and Co2 in Table 1A and antibodies to all of the bacteria in Table 1B. In one embodiment, the hyperimmunized egg product comprises antibodies to antigens B, C, Co1 and Co2 in Table 1A, antibodies to all of the bacteria in Table 1B, and antibodies to all of the viruses listed in Table 1C. In one embodiment, the hyperimmunized egg product comprises antibodies to at least one of the *Clostridium* antigens (i.e. Antigens A, B, C and D), and at least one of the Coccidium antigens (i.e. Antigens Co1 and Co2). The antibody may be an IgA, IgM or IgY antibody. In a particular embodiment, the antibody is an IgY antibody.

The hyperimmunized egg or hyperimmunized egg product may contain an increased level of an antibody (e.g. an IgY antibody) specific to a particular antigen disclosed herein relative to a control egg or control egg product obtained from an egg-producing animal that is not hyperimmunized with the particular antigen. For example, in some embodiments the hyperimmunized egg or hyperimmunized egg product contains an increased level of an antibody that is specific to one of the antigens shown in Table 1A, one of the bacteria shown in Table 1B, or one of the viruses shown in Table 1C, relative to a control egg or egg product obtained from an egg-producing animal that is not hyperimmunized. In some embodiments, the hyperimmunized egg or egg product comprises at least 10%, 20%, 30%, 40%, 50%, 100%, 200%, 300%, 400% or 500% more antibody (e.g. IgY antibody) specific to a particular antigen disclosed herein (for example one of the antigens shown in Table 1A, one of the bacteria shown in Table 1B, or one of the viruses show in Table 1C) by weight relative to a control egg or control egg product obtained from an egg-producing animal that is not hyperimmunized with the particular antigen. For example, in some embodiments, the hyperimmunized egg or hyperimmunized egg product comprises at least 10%, 20%, 30%, 40%, 50%, 100%, 200%, 300%, 400% or 500% more antibody (e.g. IgY antibody) specific to Antigen A relative to a control egg or control egg product obtained from an egg-producing animal that is not hyperimmunized with Antigen A. In some embodiments, the hyperimmunized egg or hyperimmunized egg product comprises at least 10%, 20%, 30%, 40%, 50%, 100%, 200%, 300%, 400% or 500% more antibody (e.g. IgY antibody) specific to Antigen B relative to a control egg or control egg product obtained from an egg-producing animal that is not hyperimmunized with Antigen B. In some embodiments, the hyperimmunized egg or hyperimmunized egg product comprises at least 10%, 20%, 30%, 40%, 50%, 100%, 200%, 300%, 400% or 500% more antibody (e.g. IgY antibody) specific to Antigen C relative to a control egg or control egg product obtained from an egg-producing animal that is not hyperimmunized with Antigen C. In some embodiments, the hyperimmunized egg or hyperimmunized egg product comprises at least 10%, 20%, 30%, 40%, 50%, 100%, 200%, 300%, 400% or 500% more antibody (e.g. IgY antibody) specific to Antigen D relative to a control egg or control egg product obtained from an egg-producing animal that is not hyperimmunized with Antigen D. In some embodiments, the hyperimmunized egg or hyperimmunized egg product comprises at least 10%, 20%, 30%, 40%, 50%, 100%, 200%, 300%, 400% or 500% more antibody (e.g. IgY antibody) specific to Antigen Co1 relative to a control egg or control egg product obtained from an egg-producing animal that is not hyperimmunized with Antigen Co1. In some embodiments, the hyperimmunized egg or hyperimmunized egg product comprises at least 10%, 20%, 30%, 40%, 50%, 100%, 200%, 300%, 400% or 500% more antibody (e.g. IgY antibody) specific to Antigen Co2 relative to a control egg or control egg product obtained from an egg-producing animal that is not hyperimmunized with Antigen Co2.

The hyperimmunized egg or hyperimmunized egg product may contain increased levels of antibodies to two or more of: the antigens shown in Table 1A, the bacteria shown in Table 1B, or the viruses shown in Table 1C, relative to a control egg or control egg product obtained from an egg-producing animal that is not hyperimmunized. For example, in a particular embodiment, the hyperimmunized egg or hyperimmunized egg product comprises at least 10%, 20%, 30%, 40%, 50%, 100%, 200%, 300%, 400% or 500% more antibody to Antigen B and at least 10%, 20%, 30%, 40%, 50%, 100%, 200%, 300%, 400% or 500% more antibody to Antigen C relative to a control egg or control egg product obtained from an egg-producing animal that is not hyperimmunized with Antigen B or Antigen C.

Comparisons of antibody titers in hyperimmunized egg products and control egg products may be determined by methods known in the art. For example, in one embodiment, eggs are collected and the antibody titers are monitored by ELISA at regular intervals. To determine antibody titers, total IgY is extracted from eggs using Pierce™ Chicken IgY Purification Kit (Thermo Fisher Scientific, Waltham, Mass.). Briefly, 2 mL of egg is mixed with five volumes of delipidation reagent and IgY is purified following the manufacturer's instructions. Spray dried egg powder samples are reconstituted in sterile PBS at 1 mg/mL, and filtered through a 0.22 μm membrane filter. Specific antibody titers in the isolated IgY or egg powder samples are measured by ELISA. Flat bottom, 96-well microtiter plates (Corning® Costar®, Corning, N.Y.) are coated with purified recombinant proteins (e.g. Antigens B, C, Co1, or Co2) at 10 μg/mL (100 μL/well) and incubated overnight at 4° C. The plates are washed twice with PBS containing 0.05% Tween 20 (Sigma-Aldrich, St. Louis, Mo.) and blocked with 100 μL/well of PBS containing 1% Bovine Serum Albumin (BSA) and incubated for 1 h at RT. Serially diluted (in PBS with 0.1% BSA) IgY samples from egg powder samples are added to the plates in triplicate wells (100 μL/well) and incubated for 2 h at RT with constant shaking. The plates are then washed with PBS-T and treated with peroxidase-conjugated rabbit anti-chicken IgY (IgG) antibody (1:500; Sigma), incubated for 30 min, followed by color development for 10 minutes with 0.01% tetramethylbenzidine substrate (Sigma) in 0.05 M Phosphate-Citrate buffer, pH 5.0. Bound antibodies are detected by measuring optical density at 450 nm ($OD_{450}$) using a microplate reader (Bio-Rad, Hercules, Calif.).

In some embodiments, the hyperimmunized egg or egg product comprises at least 0.0001%, 0.0005%, 0.001%, 0.005%, 0.01%, 0.05%, or 0.1% by weight of an IgY antibody to a specific antigen (for example, one of the antigens shown in Table 1A, one of the bacteria shown in Table IB, or one of the viruses shown in Table IC).

Hyperimmunized eggs or egg products may contain an increased level of two or more antibodies (e.g. IgY antibodies), each of which is specific to a different antigen disclosed herein, relative to a control egg or egg product obtained from an egg-producing animal that is not hyperimmunized. For example, in some embodiments, the hyperimmunized egg or egg product contains an increased level of an antibody (e.g. an IgY antibody) that is specific to Antigen B, and an increased level of an antibody (e.g. an IgY antibody) that is specific to Antigen C, relative to a control egg or egg product. In a particular embodiment, the hyperimmunized egg or egg product contains increased levels of an antibody specific to Antigen B, an antibody specific to Antigen C, an antibody specific to Antigen Co1, and an antibody specific to Antigen Co2, relative to a control egg or egg product. In a further particular embodiment, the hyperimmunized egg or egg product contains increased levels of an antibody specific to Antigen B, an antibody specific to Antigen C, an antibody specific to Antigen Co1, an antibody specific to Antigen Co2, antibodies specific to the bacteria shown in Table IB, and antibodies specific to the viruses shown in Table IC, relative to a control egg or egg product. The level of increase of each antibody (e.g. IgY antibody) in the hyperimmunized egg or egg product may be at least 10%, 20%, 30%, 40%, 50%, 100%, 200%, 300%, 400%, 500% or more by weight, relative to a control egg or egg product.

Hyperimmunized eggs or egg products comprising two or more antibodies (e.g. IgY antibodies), each of which is specific to a different antigen listed in Table 1A, Table IB, or Table IC may be prepared by immunizing an egg-producing animal with two or more different antigens. In other embodiments, a hyperimmunized egg or egg product comprising two or more antibodies, each of which is specific to a different antigen, may be prepared by combining hyperimmunized egg products from different egg-producing animals immunized with different antigens. For example, in one embodiment a hyperimmunized egg or egg product comprising antibodies to antigens B and C listed in Table 1A may be prepared by immunizing an egg-producing animal with antigens B and C. In another embodiment, a hyperimmunized egg or egg product comprising antibodies to antigens B and C listed in Table 1A is prepared by combining a hyperimmunized egg product from an egg-producing animal immunized with antigen B with a hyperimmunized egg product from an egg-producing animal immunized with antigen C. In certain embodiments, a whole egg comprises 50-100 mg of IgY.

Compositions and Administration

Once the egg-producing animals have been sufficiently hyperimmunized, it is preferred that the eggs from these animals are collected and processed to produce a hyperimmunized egg product in administrable form. Subsequently, the hyperimmunized egg product can be administered to an avian (e.g. a chicken or turkey).

In some embodiments the hyperimmunized egg product is encapsulated. Methods of encapsulating antibodies and other proteins are known in the art and are described, for example, in U.S. Pat. No. 7,105,158. Materials that are biodegradable and nonantigenic can be used as the encapsulating material. Encapsulating materials include, but are not limited to albumin, PLGA, globulin, natural and synthetic polymers, and thermoplastic polymers. Any polymer that is biocompatible and bioerodible may be used for encapsulation. A number of available crosslinking agents such as glutaraldehyde can be used to crosslink the encapsulating material. Additionally, the pharmaceutically delivered material may contain microspheres of encapsulated drug whereby the microspheres have different concentrations of crosslinking agent used, thereby creating a prolonged continuous release of the drug.

In some embodiments, the hyperimmunized egg product is in the form of a microparticle or nanoparticle, for example, an encapsulated microparticle or encapsulated nanoparticle. The microparticles and nanoparticles can have any shape. Typically the microparticles and nanoparticles are spherical. Other suitable shapes include, but are not limited to, flakes, triangles, ovals, rods, polygons, needles, tubes, cubes and cuboid structures. In certain embodiments, the microparticles have a diameter of less than 10, 9, 8, 7, 6, 5, 4, 3, 2, 1, 0.9, 0.8, 0.7, 0.6, 0.5, 0.4, 0.3, 0.2 or 0.1 micron(s). Any of these values may be used to define a range for the diameter of the microparticle. For example the diameter of the microparticle may be from about 0.1 to about 10 microns, from about 0.1 to about 1 micron, or from about 0.1 to about 2 microns. In other embodiments, larger microparticles or particles may be used. For example the microparticles may have a diameter ranging from 10 microns to 1000 microns. In certain embodiments, the nanoparticles have a diameter of less than 1000, 900, 800, 700, 600, 500, 400, 300, 200, 100, or 10 nm. Any of these values may be used to define a range for the diameter of the nanoparticle. For example the diameter of the nanoparticle may be from about 10 to about 1000 nm, from about 100 to about 1000 nm, or from about 10 to about 100 nm.

There are several processes whereby microparticles or nanoparticles can be encapsulated, including, for example, multi-walled microencapsulation, hot melt encapsulation, phase separation encapsulation, spontaneous emulsion, solvent evaporation microencapsulation, solvent removal microencapsulation, and coacervation. These methods are known in the art. Detailed descriptions of the methods are discussed in Mathiowitz et al., "Microencapsulation", in Encyclopedia of Controlled Drug Delivery, vol. 2, pp. 495-546, 1999, John Wiley & Sons, Inc. New York, N.Y., which is incorporated by reference herein in its entirety.

In some embodiments, the IgY antibody specific for an antigen disclosed herein (e.g. an antigen listed in Table 1A, Table 1B or Table IC) is administered to the avian in a concentrated form. For example, in some embodiments, the IgY antibody is purified and concentrated before administration to the subject. Methods of purifying and concentrating IgY antibodies from egg products are known in the art and are described, for example, in U.S. Pat. No. 5,367,054, which is incorporated by reference herein in its entirety.

The hyperimmunized egg product of the present invention is administered to an avian (e.g. a chicken or turkey) by any means that treats or prevents necrotic enteritis in the avian. In certain embodiments, administration occurs by directly feeding an egg or any derivative of the egg. Egg and egg yolk are natural food ingredients and are non-toxic and safe. In other embodiments, the hyperimmunized egg product may be administered by injection, for example, subcutaneous injection or intramuscular injection. Any of several known pharmaceutical carriers can be used in the preparation of an injectable or otherwise administrable preparation, including phosphate buffered saline, saline, ethanol, propylene glycol and the like. In some embodiments, the hyperimmunized egg product is administered through drinking water. In a particular embodiment, the IgY antibody is purified and then added to the drinking water for administration to the avian.

In certain embodiments, the hyperimmunized egg product is administered as a composition comprising one or more additional compounds. These additional compounds include, but are not limited to an animal feed, an animal dietary supplement, and a probiotic. For example, in one embodiment, the hyperimmunized egg product of the invention is integrated into an animal feed or an animal dietary supplement. One preferred method for preparing the egg of the invention to be incorporated into animal feed or a dietary supplement involves drying the egg into an egg powder. Although various methods are known for drying eggs, spray drying is a preferred method. The process of spray drying eggs is well known in the art. In some embodiments, the composition is an aqueous solution comprising the hyperimmunized egg product.

In certain embodiments, whole eggs are divided into separate fractions such as egg yolks and egg whites. For example, it is generally known in the art that IgY antibody is found in egg yolks. Accordingly, those having ordinary skill in the art would clearly recognize that separation of egg yolks could provide more potent fractions or elimination of undesirable components, and would allow for other modes of administration such as administering egg product parenterally, subcutaneously, intravenously, intramuscularly, intraperitoneally, intranasally, orally or topically. Such further separation will provide for the ability to make encapsulated products and compositions comprising said egg or fraction thereof.

It has been the inventors finding that the administration of an effective amount of the hyperimmune egg product of the present disclosure is effective in the treatment and prevention of necrotic enteritis. The hyperimmune egg product is preferably administered to the avian in an amount that is immunologically effective in treating and preventing this disorder, as well as treating symptoms of this disorder such as lesion formation and weight loss. Dosage and duration of the administration will depend upon the particular condition of the avian, whether the disease is present, and, if so, the advancement of the condition in the avian. It is preferred that the hyperimmune egg product is provided in whatever amount is necessary and effective in treating and/or preventing necrotic enteritis, lesion formation, weight loss, and other symptoms of necrotic enteritis. For example, in some cases, daily amounts ranging from less than one to several whole, hyperimmune eggs (or hyperimmune egg products containing the equivalent of less than one to several whole, hyperimmune eggs) can be administered to the avian depending on the particular circumstance of the condition. More potent fractions can be separated and concentrated by methods well-known in the art, from several hundred eggs.

In certain embodiments, the effective amount of the hyperimmunized egg product administered to an avian (e.g. a chicken or turkey) is 0.1, 0.2, 0.3, 0.4, 0.5, 0.6, 0.7, 0.8, 0.9, 1, 2, 3, 4, 5, 6, 7, 8, 9 or 10 grams per kilogram of subject weight per day. Any of these values may be used to define a range for the effective amount of the hyperimmunized egg product administered to the avian. For example, in some embodiments the effect amount of the hyperimmunized egg product is between 0.1 and 10 grams, between 0.5 to 6 grams, or between 1 and 5 grams per kilogram of subject weight per day.

In certain embodiments, the composition comprises at least 0.01%, 0.05%, 0.1%, 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98% or 99% w/w of the hyperimmunized egg product. Any of these values may be used to define a range for the concentration of the hyperimmunized egg product in the composition. For example, in some embodiments, the composition comprises between 0.01% and 50%, between 0.1% and 50%, or between 1% and 50% w/w of the hyperimmunized egg product.

This invention is further illustrated by the following examples which should not be construed as limiting. The contents of all references, accession numbers, published patents and patent applications cited throughout the application are hereby incorporated by reference.

Sequences in Sequence Listing

| SEQ ID NO: | Description |
|---|---|
| 1 | Antigen A, amino acid sequence |
| 2 | Antigen A, nucleic acid sequence |
| 3 | Antigen B, amino acid sequence |
| 4 | Antigen B, nucleic acid sequence |
| 5 | Antigen C, amino acid sequence |
| 6 | Antigen C, nucleic acid sequence |
| 7 | Antigen D, amino acid sequence |
| 8 | Antigen D, nucleic acid sequence |
| 9 | Antigen Co1, amino acid sequence |
| 10 | Antigen Co1, nucleic acid sequence |
| 11 | Antigen Co2, amino acid sequence |
| 12 | Antigen Co2, nucleic acid sequence |

EXAMPLES

Example 1—Preparation of Hyperimmunized Egg Products

Preparation of ET-50 Vaccine

A bacterial culture containing all of the bacteria shown in Table 1B above, as obtained from the American Type Culture Collection, was reconstituted with 15 mL of media and incubated overnight at 37° C. Once good growth was obtained, approximately one-half of the bacterial suspension was employed to inoculate one liter of broth with the inoculate being incubated at 37° C.

After good growth was visible in the culture, the bacterial cells were harvested by centrifugation of the suspension for 20 minutes to remove the media. The bacterial pellet obtained was resuspended in sterile saline solution and the bacterial sample was centrifuged three times to wash the media from the cells. After the third sterile saline wash, the bacterial pellet was resuspended in a small amount of double distilled water.

The media-free bacterial suspension was killed by placing the suspension in a glass flask in an 80 C water bath overnight. The viability if the broth culture was tested with a small amount of killed bacteria, incubated at 37° C. for five days and checked daily for growth to certify that the bacteria had been killed.

The killed bacteria were lyophilized until dry. The dry bacteria were then mixed with sterile saline solution to a concentration of $2.2 \times 10^8$ bacterial cells/mL saline (1.0 optical density reading at 660 nm). Bacteria contained in the ET-50 vaccine are listed in Table 1B above.

Preparation of *Clostridium* and *Eimeria* Antigen Vaccines

The antigens from *Clostridium perfringens* and *Eimeria tenella* listed in Table 2 below were expressed in *E. coli* and purified as described in Lee et al., 2011, Research in Veterinary Science 91: e80-e86, which is incorporated by reference herein in its entirety. Briefly, full-length coding sequences of the B, C, Co1 and Co2 antigens were cloned into the pET32a(+) vector with an $NH_2$-terminal polyhistidine tag and transformed into *Escherichia coli*. Transformed *E. coli* DH5α bacteria were grown to mid-log phase (16 h at 37° C.), and induced with 1.0 mM of isopropyl-β-d-thiogalactopyranoside (Amresco, Cleveland, Ohio) for 5 h at 37° C. The bacteria were then harvested by centrifugation and disrupted by sonication on ice (Misonix, Farmingdale, N.Y.). The supernatant was incubated with Ni-NTA agarose (Qiagen, Valencia, Calif.) for 1 h at room temperature (RT) and the resin washed with PBS. Purified proteins were eluted and the purity confirmed on Coomassie blue-stained SDS-acrylamide gels.

TABLE 2

Clostridia and *Eimeria* antigens for production of hyperimmunized egg product

| Egg Powder | Description |
|---|---|
| B | *Clostridium perfringens* elongation factor Tu (EF-Tu) (Genbank Accession No. KY584047) |
| C | *Clostridium perfringens* necrotic enteritis B-like (NetB) toxin (Genbank Accession No. KY559052) |
| Co1 | *Eimeria tenella* elongation factor 1-alpha (Genbank Accession No. KX900609) |
| Co2 | *Eimeria tenella* 3-1E profilin (Genbank Accession No. AF113613.2) |

Viral Vaccines

The viral vaccines MAXIMUNE® 6 (Ceva Animal Health, Lenexa, Kans.), AviPro® IB Ark (Lohman Animal Health Int., Winslow, Me.), and Adenomune® II (Ceva Animal Health, Lenexa, Kans.) were obtained from commercial sources. The viral vaccines are described in Table 1C above. The combination of the viruses in MAXIMUNE® 6, AviPro® IB Ark, and Adenomune® II is referred to herein as Antigen "H".

Immunization Procedure for Hyperimmune Egg Product

Vaccinations were performed with the killed preparation of pathogens described above for ET-50, or the purified proteins described above for the *Clostridium* and *Eimeria* antigens. For the first vaccination for ET-50, the bacteria were mixed with complete Freund's adjuvant, and 5.6 mg of bacterial material were injected into the breast muscle of a chicken. For the remaining vaccinations for ET-50, the bacterial preparation was mixed with incomplete Freund's adjuvant and injected into the chickens at two week intervals for six months. Eggs were collected from the hyperimmunized chickens and then spray dried into a powder form.

For the *Clostridium* and *Eimeria* antigens, IgY antibodies were raised in laying hens by hyperimmunizing with one or more of the four antigens B, C, Co1 or Co2 as shown below in Table 3A. The laying hens were administered a first injection followed by booster injections 2 weeks and 4 weeks after the first injection. The antigens were formulated as a Freund's vaccine at a final concentration of 100 ag/ml. For the first injection, each hen received 2 doses of 0.5 ml for each antigen, such that each hen received 100 ag of each antigen. For example, for hens that were injected with the B and C antigens (Group 3), each hen received 100 ag of Antigen B and 100 ag of Antigen C for the first injection. For the booster injections, each hen received one 0.5 ml dose for each antigen, such that each hen received 50 ag of antigen of each antigen. The antigens were administered to breast tissue by subcutaneous/intramuscular injection.

The viral antigens were administered to the laying hens according to manufacturer's instructions. Briefly, MAXIMUNE® 6 was administered by subcutaneous injection to the neck. The hens received a single 0.5 ml dose MAXIMUNE® 6 as a priming dose, followed by 0.5 ml boost doses 14 and 28 days after the priming dose. AviPro® IB Ark and Adenomune® II were administered by eyedropper into the beak. The hens received a single 0.6-0.8 ml priming dose of AviPro® IB Ark and Adenomune® II, followed by 0.6-0.8 ml boost doses 14 and 28 days after the priming dose. Egg powder H refers to egg powder obtained from hens that were immunized with MAXIMUNE® 6, AviPro® IB Ark and Adenomune® II.

TABLE 3A

Antigens for preparation of Hyperimmune Egg Powders. Each laying hen was immunized with a single antigen or a combination of antigens, as shown.

| Group | Antigen(s) for Preparation of Hyperimmune Egg Powder |
|---|---|
| 1 | B |
| 2 | C |
| 3 | B + C |
| 4 | Co1 |
| 5 | Co2 |
| 6 | Co1 + Co2 |

TABLE 3A-continued

Antigens for preparation of Hyperimmune Egg Powders.
Each laying hen was immunized with a single antigen
or a combination of antigens, as shown.

| Group | Antigen(s) for Preparation of Hyperimmune Egg Powder |
|---|---|
| 7 | B + C + Co1 |
| 8 | B + C + Co2 |
| 9 | B + C + Co1 + Co2 |
| 10 | H |
| 11 | H + B + C + Co1 + Co2 + ET-50 |

During the spray drying procedure, inlet temperatures did not exceed 320° F., exhaust temperatures were maintained in accordance with producing powder in the range of 3.0 to 4.0 percent finished moisture, and pump pressure was maintained around 2500 to 4000 P.S.I. Lower temperatures ranging from 100-160° F. were used, and samples were monitored for moisture content during the drying process to obtain a final hyperimmunized egg product having the desired consistency.

Example 2—Efficacy of 0.5% Dose of Hyperimmune Egg Powder Against Necrotic Enteritis in Broiler Chickens Infected with a Subclinical Level of *C. perfringens*

The objective of this study was to evaluate the synergistic effect of various combinations of hyperimmune egg antibodies raised against *Clostridium* or *Eimeria* antigens in a mild subclinical challenge model (similar to field challenge) in broiler chickens. The egg antibodies to the *Clostridium*, *Eimeria* or ET-50 antigens were prepared as described in Example 1 above. The experimental design involved 15 treatments with 21 birds/treatment. See Table 3 below. Treatment 1 was a non-infected and non-supplemented control. Treatments 2-15 were given an experimental subclinical necrotic enteritis (NE) infection. Treatment 2 served as the non-supplemented infected control and was given a standard diet. Treatment 3 was given feed supplemented with Virginiamycin at 20 g/ton of feed. Treatments 4-15 were given feed supplemented with different egg powders (control egg powder, powder with antibodies against *Clostridium* or *Eimeria* antigens, or combinations thereof) at 0.5% w/w. For the treatment groups containing more than one type of egg powder, chickens were immunized separately with a single antigen, and the egg powders were combined after spray drying. Egg powder collected from unimmunized hens was used as the control egg powder. There were a total of 11 egg powders (control, B, C, B+C, Co1, Co2, Co1+Co2, B+C+Co1, B+C+Co2, B+C+Co1+Co2, and B+C+Co1+Co2+ET-50+H). Feeding of supplemented feed commenced from 6 days before *Eimeria* infection. Body weight was measured before and 2 and 7 days after *C. perfringens* infection and weight gain was calculated.

TABLE 3B

Experimental Design for 0.5% Dose Study

| Treatment | No. of birds/trtmt | Description | Type of egg powder | NE infection |
|---|---|---|---|---|
| 1 | 21 | Uninfected control | — | No |
| 2 | 21 | Infected & non-supplemented | — | Yes |
| 3 | 21 | Infected & Virginiamycin supplemented | — | Yes |
| 4 | 21 | Infected | Control powder (0.5%) | Yes |
| 5 | 21 | Infected | B (0.5%) | Yes |
| 6 | 21 | Infected | C (0.5%) | Yes |
| 7 | 21 | Infected | B + C (0.5%) | Yes |
| 8 | 21 | Infected | Co1 (0.5%) | Yes |
| 9 | 21 | Infected | Co2 (0.5%) | Yes |
| 10 | 21 | Infected | Co1 + Co2 (0.5%) | Yes |
| 11 | 21 | Infected | B + C + Co1 (0.5%) | Yes |
| 12 | 21 | Infected | B + C + Co2 (0.5%) | Yes |
| 13 | 21 | Infected | B + C + Co1 + Co2 (0.5%) | Yes |
| 14 | 21 | Infected/Hofacre mix | H | Yes |
| 15 | 21 | Infected | H + B + C + Co1 + Co2 + ET-50 (0.5%) | Yes |

Newly hatched chicks were purchased from Longnecker's hatchery, Elizabethtown, Pa. Chicks were transported and then housed in brooder units and provided with feed and water ad libitum. Birds were kept in brooder pens in an *Eimeria*-free facility and transferred into finisher cages in a separate location where they were infected and kept until the end of the experimental period. All experimental procedures regarding transportation and infection were approved by the BARC Small Animal Care Committee. Any abnormal conditions were notified to the Project Leader. Birds were provided with an antibiotic-free starter diet (16% crude protein by weight)) from day 1 to 15 and a grower diet (24% crude protein by weight) from day 15 to the end of the experiment. Feed and water were given ad libitum. Feed supplemented with either egg powder at various levels was given to the birds according to their treatments starting from day 9 of age (6 days before *Eimeria* infection, 10 days before *Clostridium* infection) to the end of the experiment.

Birds were infected with a subclinical necrotic enteritis infection model optimized based on pilot trials. At 15 days of age, birds were orally infected with $5 \times 10^3$ oocysts of *Eimeria maxima* (strain 41)/bird, followed by *Clostridium perfringens* infection ($1 \times 10^8$ CFU/bird) at 19 days of age at 3 time points (9 AM, 12 PM, 3 PM). Birds were switched to a high protein diet from day 18 of age to facilitate the development of NE. Birds were weighed individually on the day of *Eimeria* infection (Day 0), day of *Clostridium perfringens* infection (Day 4), and 2 and 7 days after *Clostridium perfringens* infection (Days 6 and 11, respectively). Weight gain was calculated. Lesion score was performed 2 days post *Clostridium perfringens* infection. Six birds per group were euthanized and approximately 20 cm intestinal segments extending 10 cm anterior and posterior to the diverticulum were obtained. Intestinal Sections were scored for necrotic enteritis lesions on a scale of 0 (none) to 4 (high) in a blind fashioned way by three independent observers. Blood samples were collected by cardiac puncture immediately following euthanasia on day 2 (4/treatment) following infection. Sera were separated by centrifuging at 2000 rpm for 20 min and stored at −20° C. until further use. All values were expressed as mean±SEM. Differences among the means were considered significant at $p<0.05$.

Results

Figure 1:
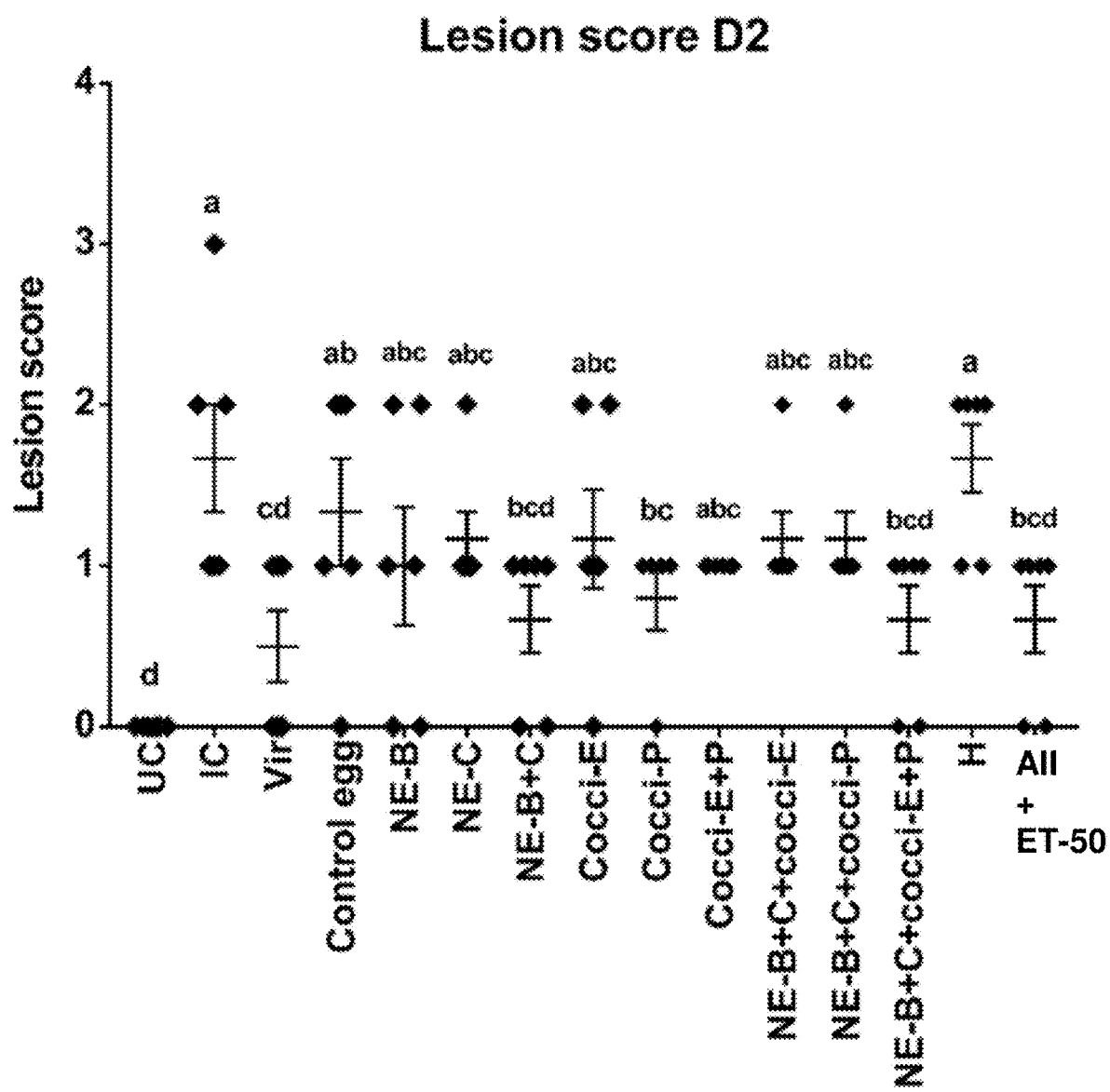
FIG. 1 shows lesion scores (mean±SEM) 2 days post-*Clostridium perfringens* infection in a subclinical model of necrotic enteritis infection (*E. maxima* infection at 15 days of age and *Clostridium perfringens* infection at 19 days of age). Birds were fed feed supplemented with different egg powders at 0.5% level from 6 days before the day of *Eimeria* infection. Birds that received standard diet with no egg powder supplementation served as non-supplemented and uninfected controls. Birds that received standard diet with no egg powder supplementation and given NE infection served as nonsupplemented and infected controls. All the birds were given a low protein diet to 19 days of age and switched to a high protein diet to facilitate development of NE. Values with no common letter differ significantly (P≤0.05). UC=untreated control; IC=infected control; Vir=virginiamycin; NE-B=*Clostridium perfringens* elongation factor Tu; NE-C=*Clostridium perfringens* necrotic enteritis B-like (NetB) toxin; Cocci-E=*Eimeria tenella* elongation factor 1-alpha; Cocci-P=*Eimeria tenella* 3-1E profilin.

Four treatment groups exhibited significantly lower lesion scores relative to the infected control 2 days after *Clostridium perfringens* infection: B+C, Co2, B+C+Co1+Co2, and H+B+C+Co1+Co2+ET-50. See FIG. 1 and Table 4. While there was no statistically significant effect on lesion score for the B (*C. perfringens* elongation factor Tu) and C (*C. perfringens* NetB toxin) treatment groups, the combination of B+C resulted in a statistically significant reduction in lesion score, indicating a synergistic effect between these treatments. Similarly, while the B+C+Co1 and B+C+Co2 treatments did not significantly reduce lesion score, treatments with the combination of B+C+Co1+Co2 resulted in a significantly lower lesion score, indicating a synergistic effect among these treatments.

Figure 2:
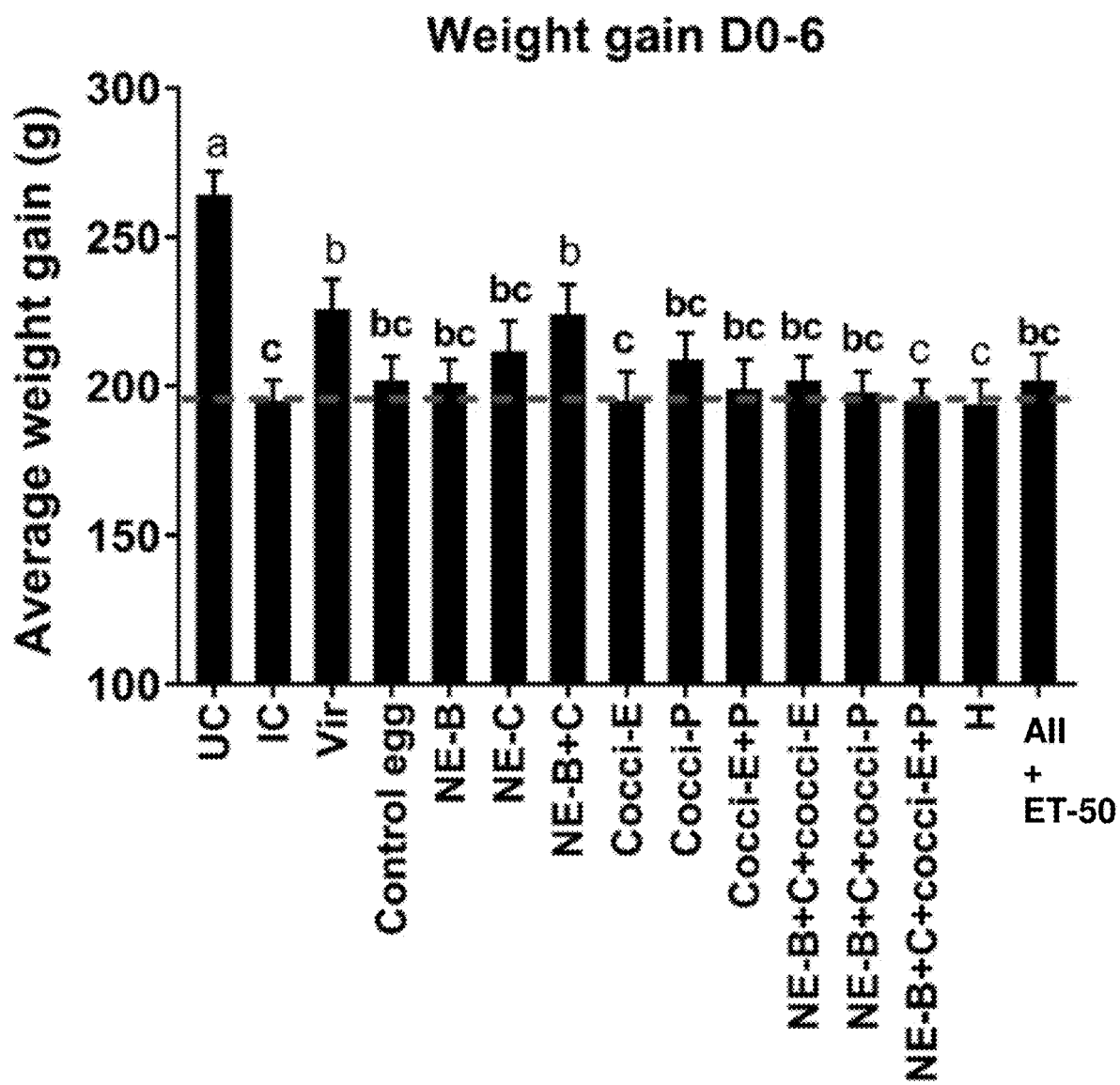
FIG. 2 shows body weight gain (mean±SEM) from Day 0 (day of *E. maxima* infection) to Day 6 (2 days post-*Clostridium perfringens* infection) in a subclinical model of NE infection. *E. maxima* infection was performed at 15 days of age and *Clostridium perfringens* infection at 19 days of age. Birds were fed feed supplemented with different egg powders at 0.5% level from 6 days before *Eimeria* infection. Birds that received standard diet with no egg powder supplementation served as non-supplemented and uninfected controls. Birds that received standard diet with no egg powder supplementation and given necrotic enteritis infection served as nonsupplemented and infected controls. All the birds were given a low protein diet to 19 days of age and switched to a high protein diet to facilitate development of necrotic enteritis. Values with no common letter differ significantly (P≤0.05). UC=untreated control; IC=infected control; Vir=virginiamycin; NE-B=*Clostridium perfringens* elongation factor Tu; NE-C=*Clostridium perfringens* necrotic enteritis B-like (NetB) toxin; Cocci-E=*Eimeria tenella* elongation factor 1-alpha; Cocci-P=*Eimeria tenella* 3-1E profilin.
Figure 3:
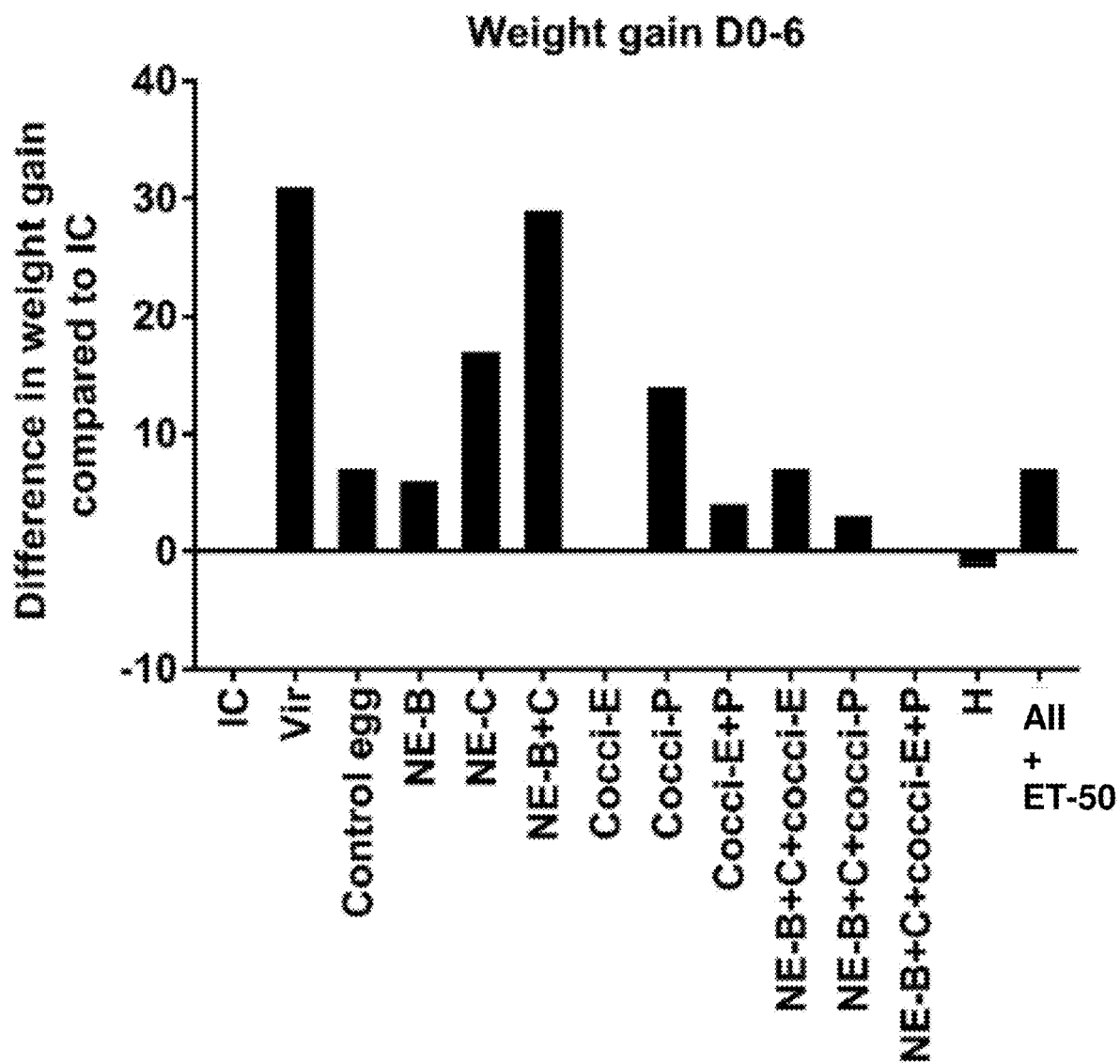
FIG. 3 shows the difference in body weight gain (mean±SEM) from infected control from Day 0 (day of *E. maxima* infection) to Day 6 (2 days post-*Clostridium perfringens* infection) in a subclinical model of necrotic enteritis infection. *E. maxima* infection was performed at 15 days of age and *Clostridium perfringens* infection at 19 days of age. Birds were fed feed supplemented with different egg powders at 0.5% level from 6 days before *Eimeria* infection. Birds that received standard diet with no egg powder supplementation served as non-supplemented and uninfected controls. Birds that received standard diet with no egg powder supplementation and given NE infection served as non-supplemented and infected controls. All the birds were given a low protein diet to 19 days of age and switched to a high protein diet to facilitate development of NE. Values with no common letter differ significantly (P≤0.05). IC=infected control; Vir=virginiamycin; NE-B=*Clostridium perfringens* elongation factor Tu; NE-C=*Clostridium perfringens* necrotic enteritis B-like (NetB) toxin; Cocci-E=*Eimeria tenella* elongation factor 1-alpha; Cocci-P=*Eimeria tenella* 3-1E profilin.
Figure 4:
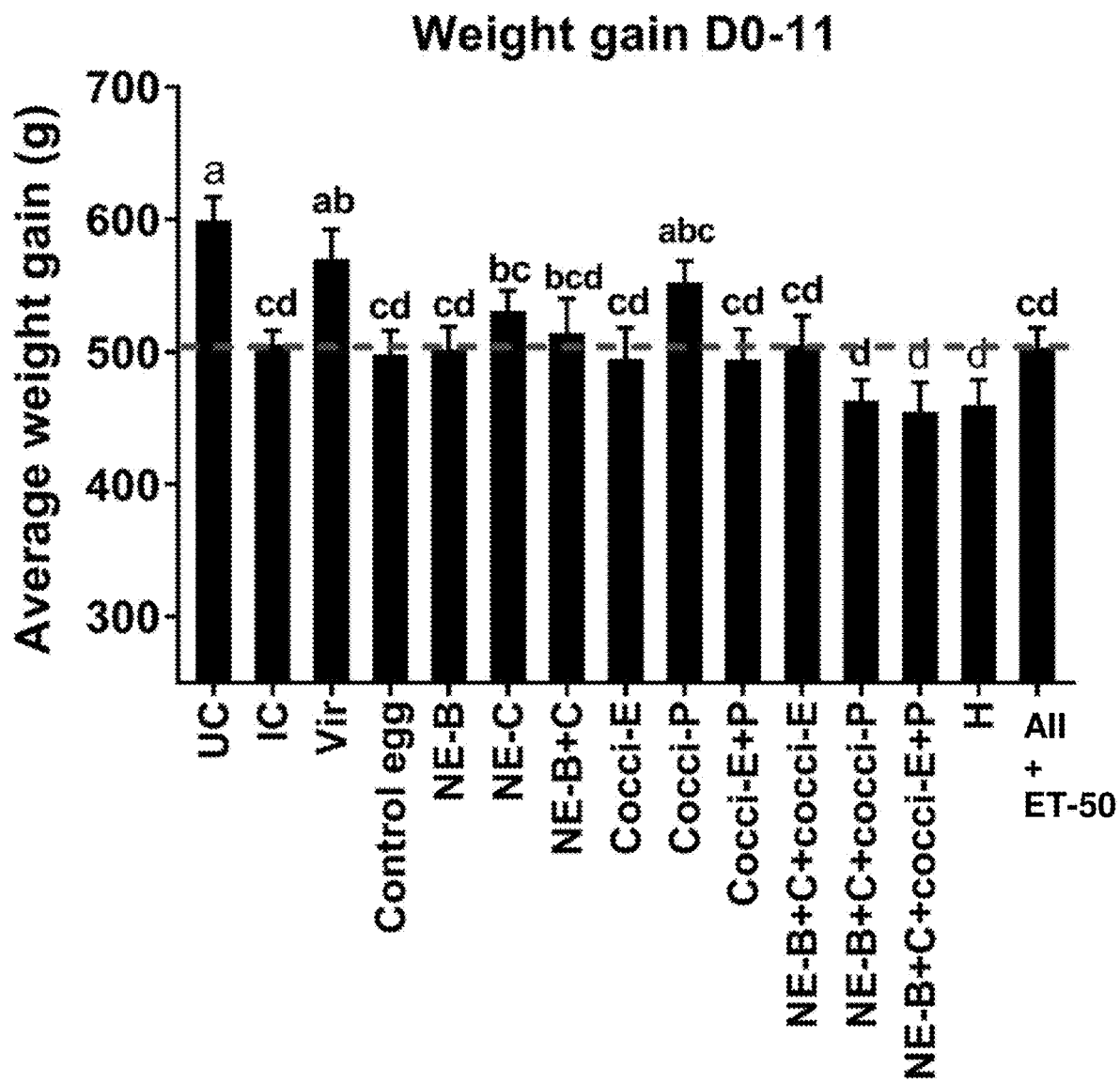
FIG. 4 shows body weight gain (mean±SEM) from Day 0 (day of *E. maxima* infection) to Day 11 (7 days post-*Clostridium perfringens* infection) in a subclinical model of necrotic enteritis infection. *E. maxima* infection was performed at 15 days of age and *Clostridium perfringens* infection at 19 days of age. Birds were fed feed supplemented with different egg powders at 0.5% level from 6 days before *Eimeria* infection. Birds that received standard diet with no egg powder supplementation served as non-supplemented and uninfected controls. Birds that received standard diet with no egg powder supplementation and given necrotic enteritis infection served as nonsupplemented and infected controls. All the birds were given a low protein diet to 19 days of age and switched to a high protein diet to facilitate development of NE. Values with no common letter differ significantly (P≤0.05). UC=untreated control; IC=infected control; Vir=virginiamycin; NE-B=*Clostridium perfringens* elongation factor Tu; NE-C=*Clostridium perfringens* necrotic enteritis B-like (NetB) toxin; Cocci-E=*Eimeria tenella* elongation factor 1-alpha; Cocci-P=*Eimeria tenella* 3-1E profilin.
Figure 5:
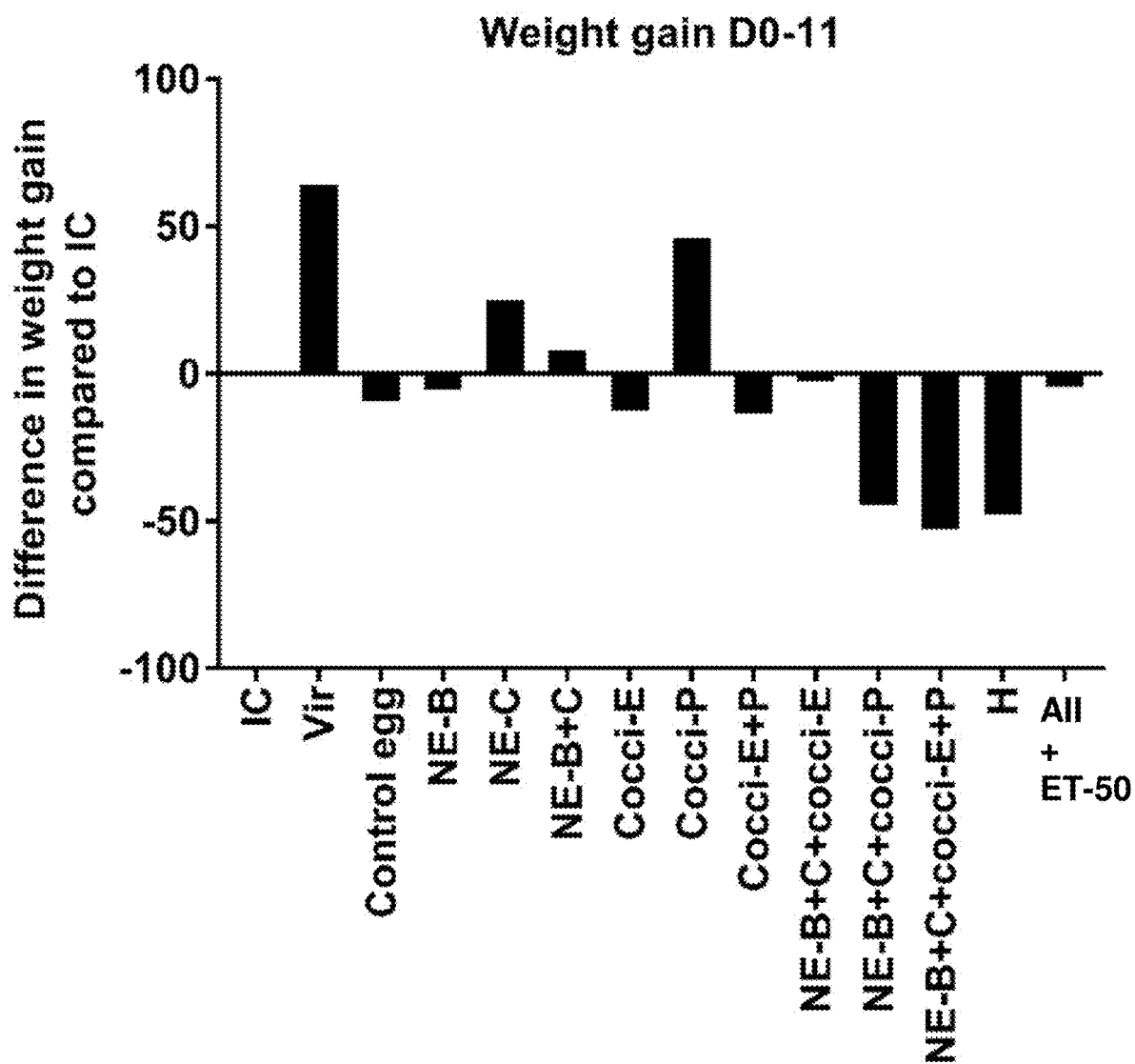
FIG. 5 shows the difference in body weight gain (mean±SEM) from infected control from Day 0 (day of *E. maxima* infection) to Day 11 (7 days post-*Clostridium perfringens* infection) in a subclinical model of necrotic enteritis infection. *E. maxima* infection was performed at 15 days of age and *Clostridium perfringens* infection at 19 days of age. Birds were fed feed supplemented with different egg powders at 0.5% level from 6 days before *Eimeria* infection. Birds that received standard diet with no egg powder supplementation served as non-supplemented and uninfected controls. Birds that received standard diet with no egg powder supplementation and given necrotic enteritis infection served as non-supplemented and infected controls. All the birds were given a low protein diet to 19 days of age and switched to a high protein diet to facilitate development of necrotic enteritis. Values with no common letter differ significantly (P≤0.05). IC=infected control; Vir=virginiamycin; NE-B=*Clostridium perfringens* elongation factor Tu; NE-C=*Clostridium perfringens* necrotic enteritis B-like (NetB) toxin; Cocci-E=*Eimeria tenella* elongation factor 1-alpha; Cocci-P=*Eimeria tenella* 3-1E profilin.

The combination treatment of B+C also significantly increased weight gain of the chicks from Day 0 to Day 6 (2 days after *Clostridium perfringens* infection) relative to the infected control, while the individual treatments of B and C had no significant effect on weight gain in this time period, providing further evidence for a synergistic effect between these treatments. See FIGS. 2 and 3 and Table 5. Indeed, the combination treatment of B+C was as effective as antibiotic (virginiamycin) treatment in increasing weight gain. FIGS. 4 and 5 and Table 6.

TABLE 4

Raw data for lesion scores (2 days post *Clostridium perfringens*-challenge)

Lesion Score - day 2 post challenge

| | UC | IC | Vir | Control egg | B | C | B + C | Co1 | Co2 | Co1 + Co2 | B + C + Co1 | B + C + Co2 | B + C + Co1 + Co2 | Hofacre | All + ET-50 |
|---|---|---|---|---|---|---|---|---|---|---|---|---|---|---|---|
| | 0 | 1 | 0 | 2 | 0 | 2 | 1 | 2 | 1 | 1 | 1 | 1 | 1 | 1 | 1 |
| | 0 | 3 | 0 | 2 | 1 | 1 | 0 | 1 | 1 | 1 | 1 | 1 | 0 | 1 | 0 |
| | 0 | 2 | 0 | 1 | 2 | 1 | 1 | 0 | 1 | 1 | 1 | 1 | 1 | 2 | 0 |
| | 0 | 1 | 1 | 2 | 2 | 1 | 1 | 1 | 1 | 1 | 1 | 1 | 1 | 2 | 1 |
| | 0 | 2 | 1 | 0 | 1 | 1 | 0 | 1 | 0 | 1 | 1 | 1 | 0 | 2 | 1 |
| | 0 | 1 | 1 | 1 | 0 | 1 | 1 | 2 | | 1 | 2 | 2 | 1 | 2 | 1 |
| Average | 0 | 1.7 | 0.5 | 1.3 | 1.0 | 1.2 | 0.7 | 1.2 | 0.8 | 1.0 | 1.2 | 1.2 | 0.7 | 1.7 | 0.7 |

UC—Uninfected control;
IC—Infected control

TABLE 5

Raw data for body weight gain day 0-6 post challenge (2 days post *Clostridium perfringens*-challenge)

Weight gain (g)day 0-6 post challenge

| | UC | IC | Vir | Cntrl egg | B | C | B + C | Co1 | Co2 | Co1 + Co2 | B + C + Co1 | B + C + Co2 | B + C + Co1 + Co2 | H | All + ET-50 |
|---|---|---|---|---|---|---|---|---|---|---|---|---|---|---|---|
| | 251 | 138 | 319 | 250 | 158 | 212 | 202 | 141 | 209 | 238 | 190 | 242 | 168 | 162 | 218 |
| | 279 | 172 | 182 | 235 | 228 | 291* | 177 | 163 | 182 | 102 | 208 | 184 | 185 | 126 | 217 |
| | 230 | 209 | 239 | 181 | 154 | 202 | 238 | 227 | 116 | 224 | 160 | 225 | 180 | 231 | 150 |
| | 241 | 203 | 267 | 242 | 178 | 210 | 271 | 186 | 265 | 198 | 264 | 261 | 202 | 224 | 272 |
| | 259 | 203 | 211 | 184 | 171 | 110* | 185 | 116* | 237 | 259 | 163 | 193 | 177 | 199 | 188 |
| | 286 | 200 | 256 | 192 | 224 | 205 | 89* | 160 | 202 | 163 | 246 | 152 | 167 | 162 | 226 |
| | 280 | 232 | 252 | 193 | 199 | 232 | 175 | 209 | 295 | 167 | 203 | 152 | 169 | 191 | 202 |
| | 331 | 236 | 211 | 277 | 181 | 213 | 322 | 348* | 185 | 169 | 200 | 214 | 197 | 198 | 204 |
| | 296 | 176 | 170 | 220 | 226 | 226 | 247 | 154 | 253 | 286 | 218 | 191 | 288 | 169 | 169 |
| | 246 | 217 | 213 | 147 | 249 | 145 | 240 | 223 | 219 | 244 | 250 | 180 | 169 | 192 | 183 |
| | 215 | 207 | 289 | 209 | 211 | 208 | 273 | 138 | 175 | 142 | 242 | 190 | 198 | 214 | 170 |
| | 256 | 190 | 162 | 192 | 284 | 213 | 250 | 256 | 206 | 210 | 215 | 183 | 186 | 136 | 182 |
| | 256 | 161 | 229 | 90* | 157 | 187 | 217 | 268 | 182 | 153 | 182 | 223 | 219 | 173 | 215 |
| | 301 | 219 | 241 | 194 | 175 | 204 | 217 | 197 | 248 | 171 | 235 | 193 | 161 | 170 | 128 |
| | 296 | 212 | 203 | 191 | 225 | 238 | 167 | 160 | 232 | 196 | 211 | 198 | 163 | 208 | 273 |
| | 310 | 228 | 157 | 158 | 173 | 355 | 204 | 191 | 171 | 216 | 183 | 244 | 214 | 171 | 233 |
| | 281 | 155 | 195 | 172 | 196 | 159 | 263 | 157 | 193 | 216 | 201 | 191 | 232 | 211 | 204 |
| | 230 | 257 | 162 | 224 | 219 | 197 | 164 | 207 | 207 | 191 | 195 | 162 | 246 | 231 | 286 |
| | 212 | 124 | 238 | 159 | 130* | 220 | 193 | 288 | 209 | 176 | 139 | 149 | 206 | 185 | 173 |
| | 217 | 152 | 321 | 187 | 243 | 199 | 248 | 190 | 228 | 255 | 134 | 218 | 167 | 261 | 216 |
| | | 205 | 233 | 242 | 162 | | | | 171 | | 208 | 213 | 197 | 261 | 127 |
| Average | 264 | 195 | 226 | 202 | 201 | 212 | 224 | 195 | 209 | 199 | 202 | 198 | 195 | 194 | 202 |

UC—Uninfected control;
IC—Infected control
*removed as outlier

TABLE 6

Raw data for body weight gain day 0-11 post challenge (7 days post *Clostridium perfringens*-challenge)

| | | | | | | | | | | | | | | | | |
|---|---|---|---|---|---|---|---|---|---|---|---|---|---|---|---|---|
| | | | | Cntrl | | | B + | | | Co1 + | B + C + | B + C + | B + C + | | | All + |
| | UC | IC | Vir | egg | B | C | C | Co1 | Co2 | Co2 | Co1 | Co2 | Co1 + Co2 | H | ET-50 |
| | 560 | 498 | 723 | 523 | 422 | 554 | 432 | 386 | 430 | 600 | 481 | 570 | 358 | 410 | 472 |
| | 554 | 473 | 709 | 589 | 525 | 615 | 419 | 575 | 603 | 468 | 435 | 482 | 453 | 390 | 500 |
| | 574 | 496 | 618 | 600 | 410 | 499 | 567 | 499 | 544 | 553 | 644 | 575 | 562 | 572 | 583 |
| | 623 | 508 | 554 | 398 | 400 | 522 | 620 | 317 | 560 | 558 | 576 | 667* | 405 | 418 | 526 |
| | 541 | 545 | 520 | 495 | 507 | 607 | 425 | 767* | 634 | 440 | 517 | 434 | 342 | 460 | 478 |
| | 702 | 542 | 540 | 494 | 521 | 505 | 657 | 595 | 510 | 583 | 406 | 547 | 367 | 473 | 462 |
| | 580 | 525 | 467 | 586 | 590 | 440 | 548 | 430 | 638 | 464 | 672 | 412 | 521 | 462 | 436 |
| | 595 | 543 | 479 | 346 | 496 | 507 | 587 | 591 | 477 | 534 | 563 | 431 | 444 | 346 | 355* |
| | 572 | 504 | 544 | 524 | 620 | 451 | 524 | 513 | 593 | 304 | 570 | 424 | 484 | 436 | 476 |
| | 620 | 556 | 566 | 467 | 443 | 628 | 585 | 558 | 508 | 406 | 468 | 483 | 401 | 366 | 479 |
| | 684 | 538 | 420 | 526 | 557 | 536 | 410 | 520 | 616 | 529 | 391 | 423 | 532 | 468 | 549 |
| | 671 | 430 | 552 | 437 | 451 | 495 | 392 | 480 | 533 | 530 | 436 | 450 | 445 | 437 | 521 |
| | 667 | 458 | 607 | 493 | 512 | 561 | 401 | 506 | 499 | 372 | 475 | 383 | 621 | 568 | 615 |
| | 441 | 471 | 686 | 457 | 500 | 512 | 634 | 465 | 616 | 572 | 418 | 435 | 258* | 506 | 419 |
| | | | | 568 | 531 | 578 | | | 519 | | 521 | 427 | 438 | 586 | 527 |
| Average | 599 | 506 | 570 | 498 | 502 | 531 | 514 | 495 | 552 | 494 | 505 | 463 | 455 | 460 | 503 |

UC—Uninfected control;
IC—Infected control
*removed as outlier

Example 3—Efficacy of 0.1% Dose of Hyperimmune Egg Powder Against Necrotic Enteritis in Broiler Chickens Infected with Clinical or Subclinical Levels of *C. perfringens*

The objective of this experiment was to evaluate the egg antibodies described above in Example 2 at a lower dose, i.e. 0.1%, in bro Lesion score was determined 2 days post *Clostridium perfringens* infection. Six birds per group were euthanatized and approximately 20 cm intestinal segments extending 10 cm anterior and posterior to the diverticulum were obtained. Intestinal sections were scored for necrotic enteritis lesions on a scale of 0 (none) to 4 (high) in a blind evaluation by three independent observers.

All values were expressed as mean±SEM. Differences among means were considered significant at $p<0.05$.

Results

Figure 6:
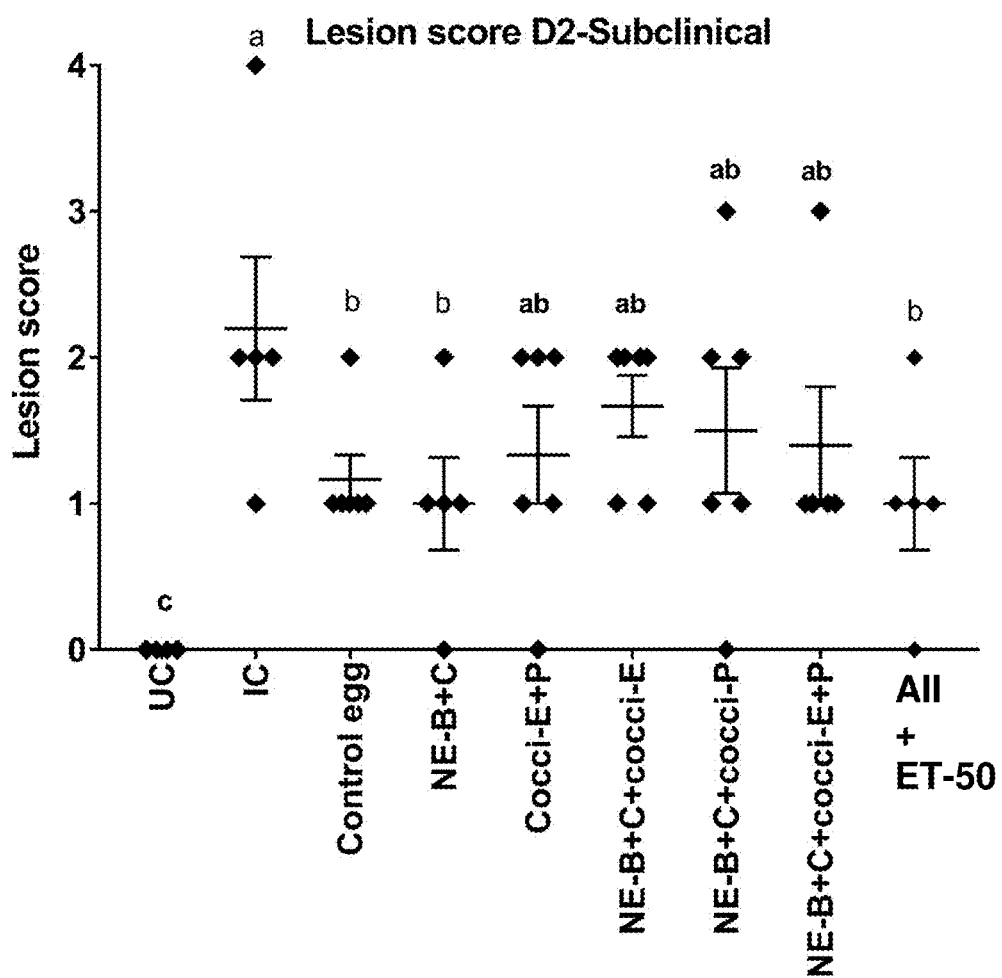
FIG. 6 shows lesion scores (mean±SEM) 2 days post-*Clostridium perfringens* infection in a subclinical model of necrotic enteritis infection (*E. maxima* infection at 15 days of age and *Clostridium perfringens* infection at 19 days of age). Birds were fed feed supplemented with different egg powders at 0.1% level from 7 days before the day of *Eimeria* infection. Birds that received standard diet with no egg powder supplementation served as non-supplemented and uninfected controls. Birds that received standard diet with no egg powder supplementation and given NE infection served as non-supplemented and infected controls. All the birds were given a low protein diet to 19 days of age and switched to a high protein diet to facilitate development of NE. Values with no common letter differ significantly (P≤0.05). UC=untreated control; IC=infected control; NE-B=*Clostridium perfringens* elongation factor Tu; NE-C=*Clostridium perfringens* necrotic enteritis B-like (NetB) toxin; Cocci-E=*Eimeria tenella* elongation factor 1-alpha; Cocci-P=*Eimeria tenella* 3-1E profilin.
Figure 7:
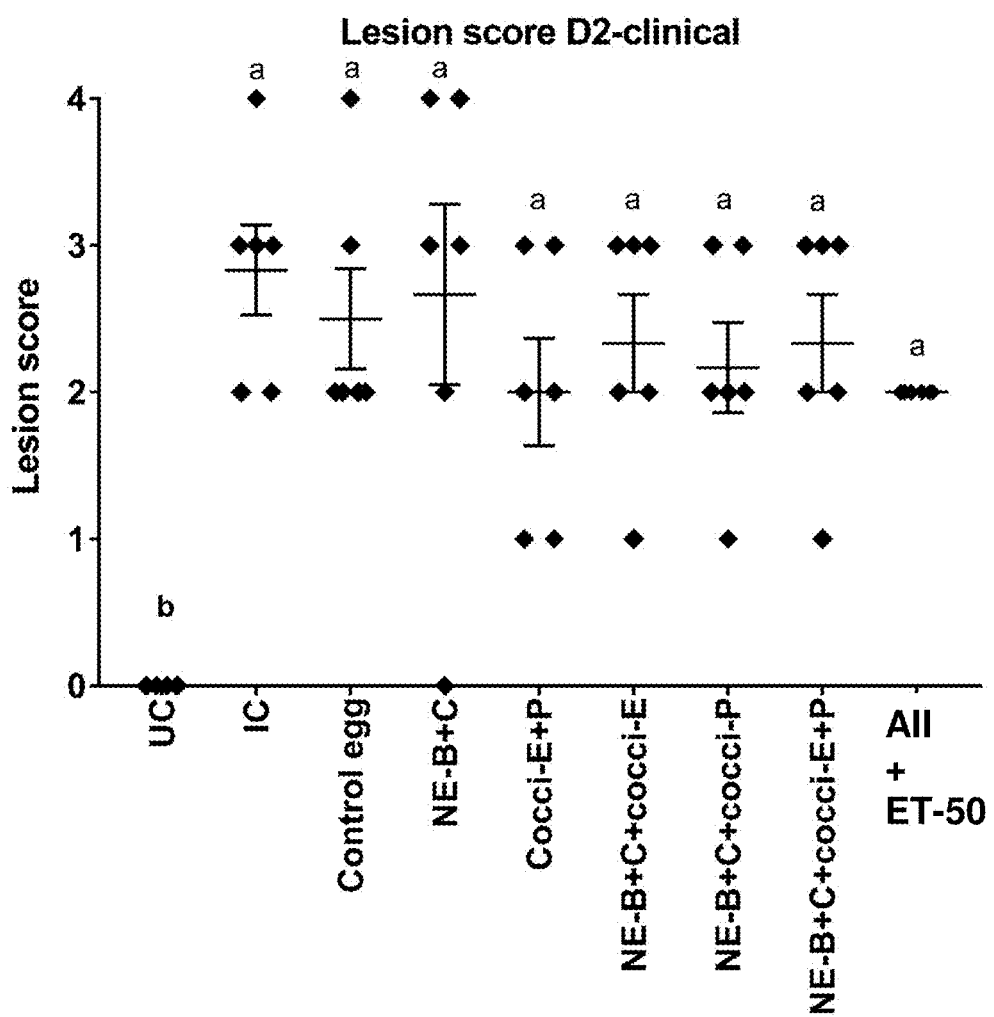
FIG. 7 shows lesion scores (mean±SEM) 2 days post-*Clostridium perfringens* infection in a clinical model of necrotic enteritis infection (*E. maxima* infection at 15 days of age and *Clostridium perfringens* infection at 19 days of age). Birds were fed feed supplemented with different egg powders at 0.1% level from 7 days before the day of *Eimeria* infection. Birds that received standard diet with no egg powder supplementation served as non-supplemented and uninfected controls. Birds that received standard diet with no egg powder supplementation and given NE infection served as non-supplemented and infected controls. All the birds were given a low protein diet to 19 days of age and switched to a high protein diet to facilitate development of NE. Values with no common letter differ significantly (P≤0.05). UC=untreated control; IC=infected control; NE-B=*Clostridium perfringens* elongation factor Tu; NE-C=*Clostridium perfringens* necrotic enteritis B-like (NetB) toxin; Cocci-E=*Eimeria tenella* elongation factor 1-alpha; Cocci-P=*Eimeria tenella* 3-1E profilin.
Figure 8:
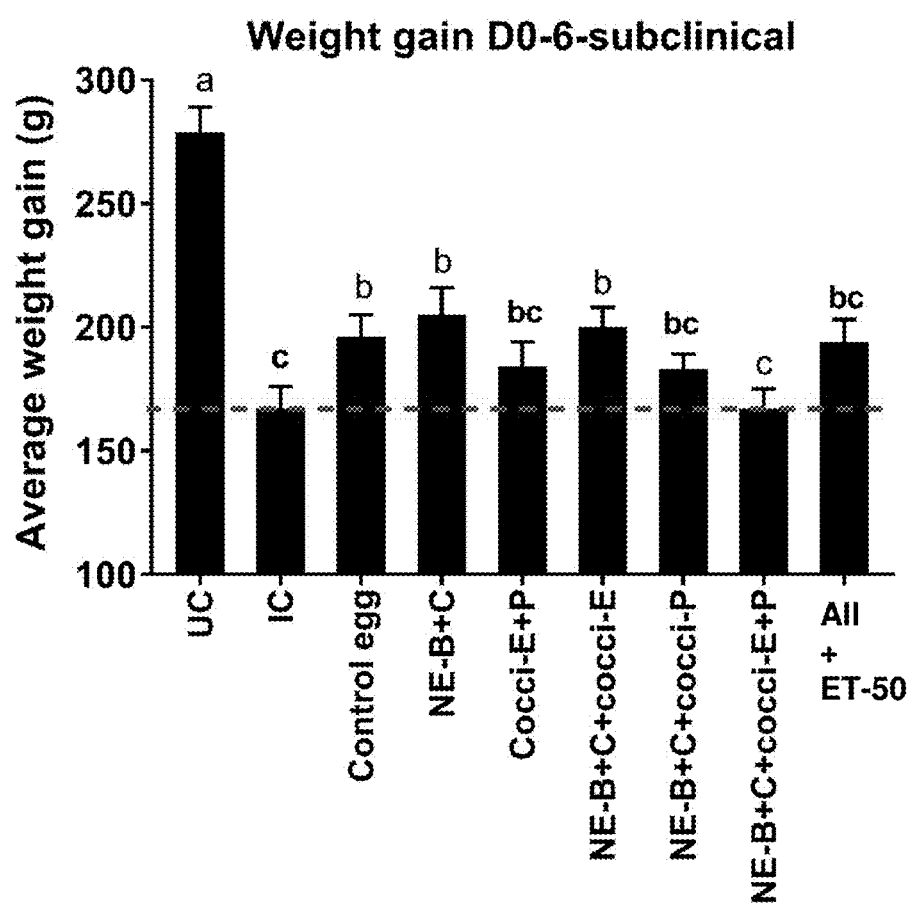
FIG. 8 shows body weight gain (mean±SEM) from Day 0 (day of *E. maxima* infection) to Day 6 (2 days post-*Clostridium perfringens* infection) in a subclinical model of necrotic enteritis infection. *E. maxima* infection was performed at 15 days of age and *Clostridium perfringens* infection at 19 days of age. Birds were fed feed supplemented with different egg powders at 0.1% level from 7 days before *Eimeria* infection. Birds that received standard diet with no egg powder supplementation served as non-supplemented and uninfected controls. Birds that received standard diet with no egg powder supplementation and given necrotic enteritis infection served as non-supplemented and infected controls. All the birds were given a low protein diet to 19 days of age and switched to a high protein diet to facilitate development of necrotic enteritis. Values with no common letter differ significantly (P≤0.05). UC=untreated control; IC=infected control; NE-B=*Clostridium perfringens* elongation factor Tu; NE-C=*Clostridium perfringens* necrotic enteritis B-like (NetB) toxin; Cocci-E=*Eimeria tenella* elongation factor 1-alpha; Cocci-P=*Eimeria tenella* 3-1E profilin.
Figure 9:
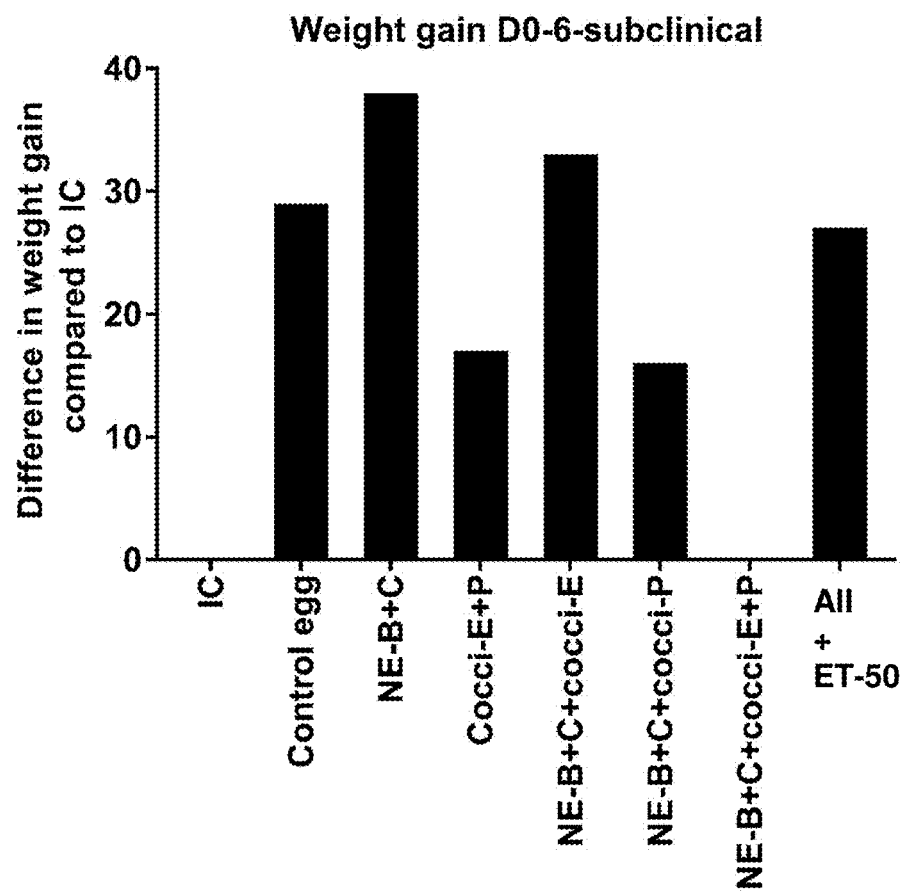
FIG. 9 shows the difference in body weight gain (mean±SEM) from Day 0 (day of *E. maxima* infection) to Day 6 (2 days post-*Clostridium perfringens* infection) in a subclinical model of necrotic enteritis infection (*E. maxima* infection at 15 days of age and *Clostridium perfringens* infection at 19 days of age). Birds were fed feed supplemented with different egg powders at 0.1% level from 7 days before *Eimeria* infection. Birds that received standard diet with no egg powder supplementation served as non-supplemented and uninfected controls. Birds that received standard diet with no egg powder supplementation and given necrotic enteritis infection served as non-supplemented and infected controls. All the birds were given a low protein diet to 19 days of age and switched to a high protein diet to facilitate development of necrotic enteritis. Values with no common letter differ significantly (P≤0.05). UC=untreated control; IC=infected control; NE-B=*Clostridium perfringens* elongation factor Tu; NE-C=*Clostridium perfringens* necrotic enteritis B-like (NetB) toxin; Cocci-E=*Eimeria tenella* elongation factor 1-alpha; Cocci-P=*Eimeria tenella* 3-1E profilin.
Figure 10:
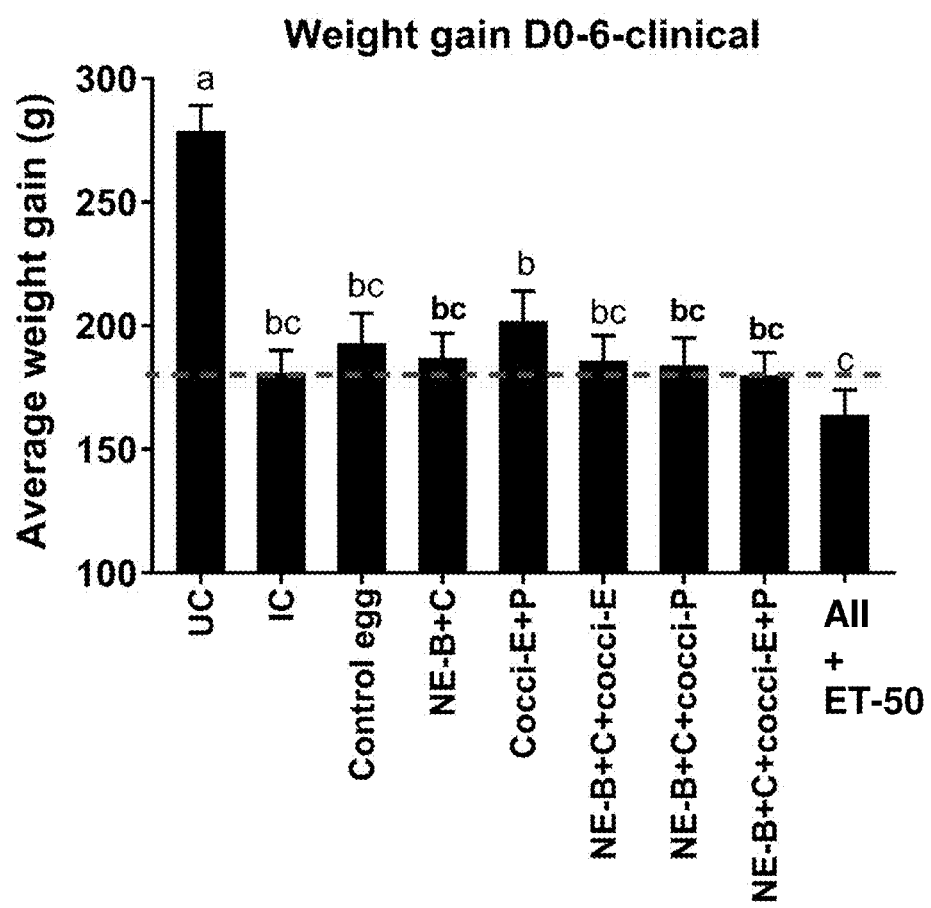
FIG. 10 shows body weight gain (mean±SEM) from Day 0 (day of *E. maxima* infection) to Day 6 (2 days post-*Clostridium perfringens* infection) in a clinical model of necrotic enteritis infection. *E. maxima* infection was performed at 15 days of age and *Clostridium perfringens* infection at 19 days of age. Birds were fed feed supplemented with different egg powders at 0.1% level from 7 days before *Eimeria* infection. Birds that received standard diet with no egg powder supplementation served as non-supplemented and uninfected controls. Birds that received standard diet with no egg powder supplementation and given necrotic enteritis infection served as non-supplemented and infected controls. All the birds were given a low protein diet to 19 days of age and switched to a high protein diet to facilitate development of necrotic enteritis. Values with no common letter differ significantly (P≤0.05). UC=untreated control; IC=infected control; NE-B=*Clostridium perfringens* elongation factor Tu; NE-C=*Clostridium perfringens* necrotic enteritis B-like (NetB) toxin; Cocci-E=*Eimeria tenella* elongation factor 1-alpha; Cocci-P=*Eimeria tenella* 3-1E profilin.
Figure 11:
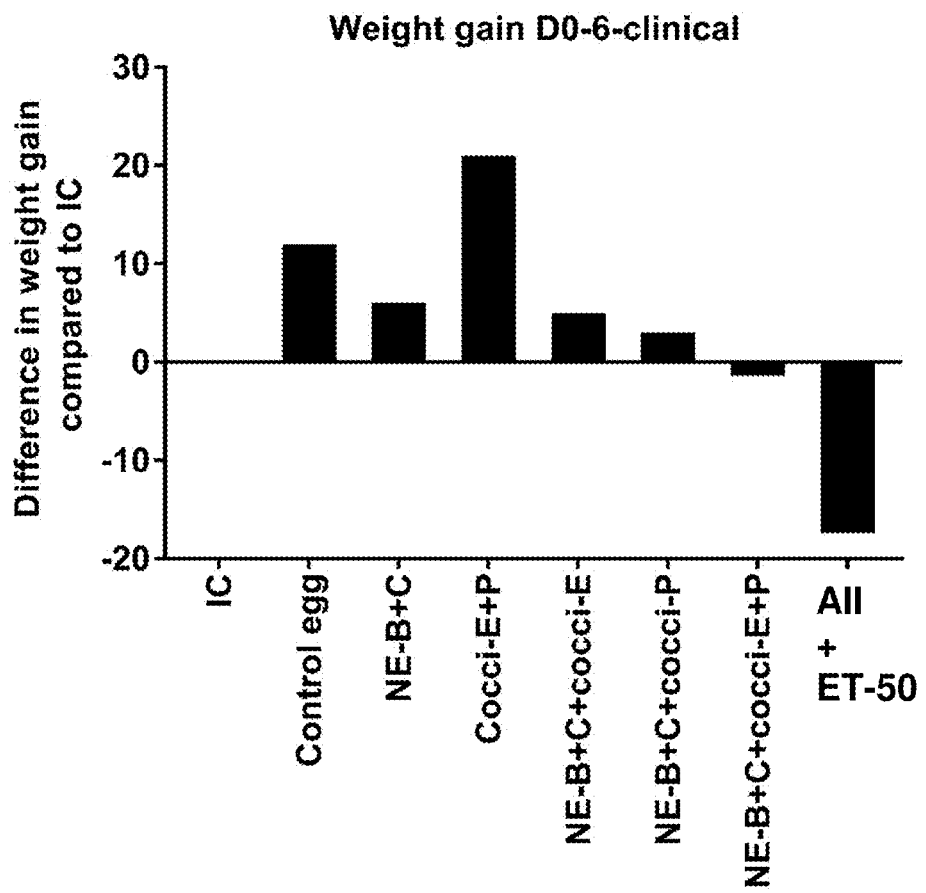
FIG. 11 shows the difference in body weight gain (mean±SEM) from infected control from Day 0 (day of *E. maxima* infection) to Day 6 (2 days post-*Clostridium perfringens* infection) in a clinical model of necrotic enteritis infection. *E. maxima* infection was performed at 15 days of age and *Clostridium perfringens* infection at 19 days of age. Birds were fed feed supplemented with different egg powders at 0.1% level from 7 days before *Eimeria* infection. Birds that received standard diet with no egg powder supplementation served as non-supplemented and uninfected controls. Birds that received standard diet with no egg powder supplementation and given necrotic enteritis infection served as non-supplemented and infected controls. All the birds were given a low protein diet to 19 days of age and switched to a high protein diet to facilitate development of NE. Values with no common letter differ significantly (P≤0.05). IC=infected control; NE-B=*Clostridium perfringens* elongation factor Tu; NE-C=*Clostridium perfringens* necrotic enteritis B-like (NetB) toxin; Cocci-E=*Eimeria tenella* elongation factor 1-alpha; Cocci-P=*Eimeria tenella* 3-1E profilin.
Figure 12:
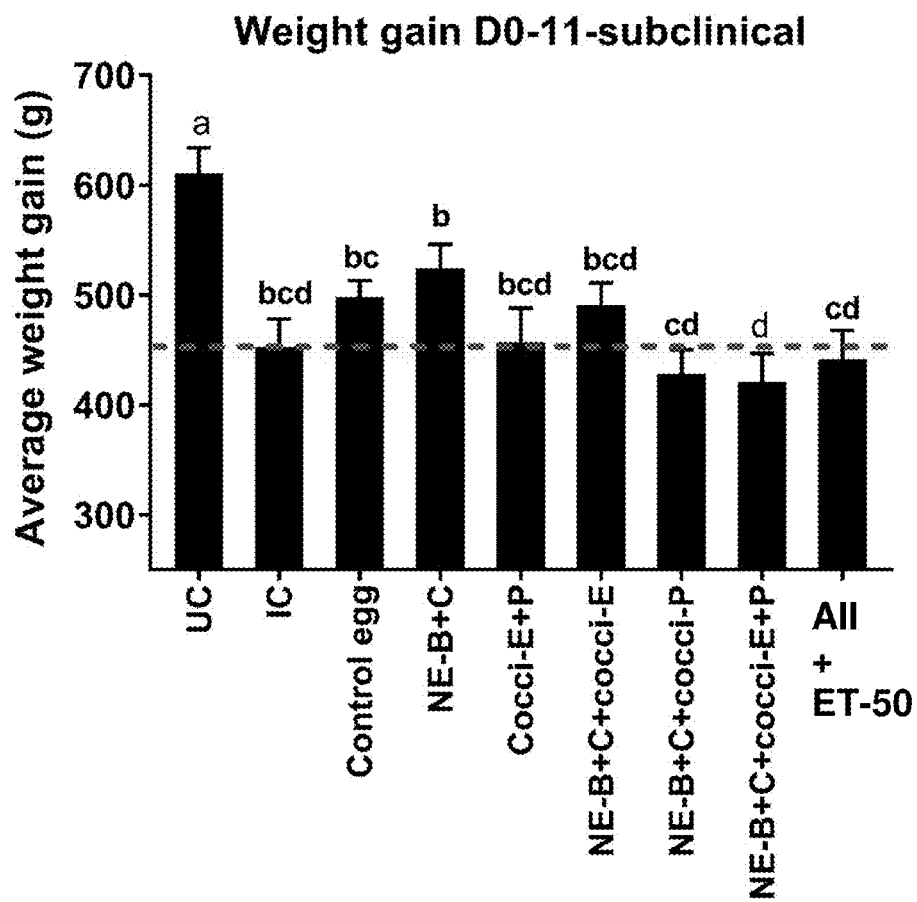
FIG. 12 shows body weight gain (mean±SEM) from Day 0 (day of *E. maxima* infection) to Day 11 (7 days post-*Clostridium perfringens* infection) in a subclinical model of necrotic enteritis infection. *E. maxima* infection was performed at 15 days of age and *Clostridium perfringens* infection at 19 days of age. Birds were fed feed supplemented with different egg powders at 0.1% level from 7 days before *Eimeria* infection. Birds that received standard diet with no egg powder supplementation served as non-supplemented and uninfected controls. Birds that received standard diet with no egg powder supplementation and given necrotic enteritis infection served as non-supplemented and infected controls. All the birds were given a low protein diet to 19 days of age and switched to a high protein diet to facilitate development of NE. Values with no common letter differ significantly (P≤0.05). UC=untreated control; IC=infected control; NE-B=*Clostridium perfringens* elongation factor Tu; NE-C=*Clostridium perfringens* necrotic enteritis B-like (NetB) toxin; Cocci-E=*Eimeria tenella* elongation factor 1-alpha; Cocci-P=*Eimeria tenella* 3-1E profilin.
Figure 13:
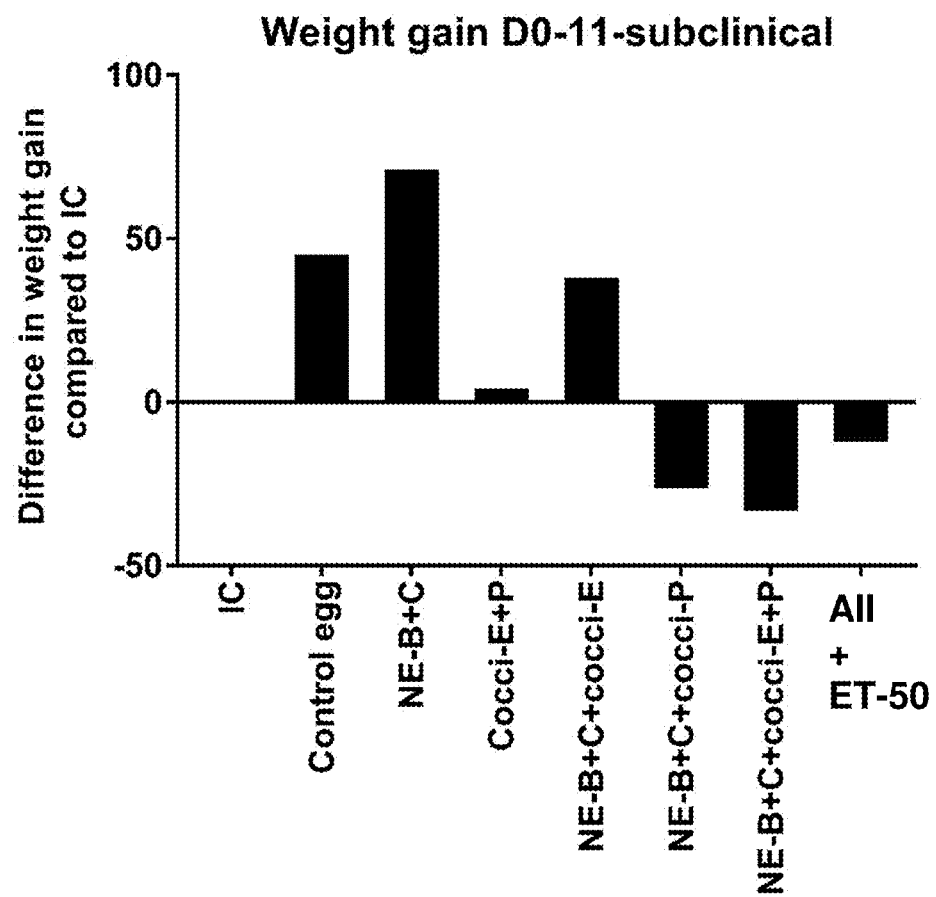
FIG. 13 shows the difference in body weight gain (mean±SEM) from infected control from Day 0 (day of *E. maxima* infection) to Day 11 (7 days post-*Clostridium perfringens* infection) in a subclinical model of necrotic enteritis infection. *E. maxima* infection was performed at 15 days of age and *Clostridium perfringens* infection at 19 days of age. Birds were fed feed supplemented with different egg powders at 0.1% level from 7 days before *Eimeria* infection. Birds that received standard diet with no egg powder supplementation served as non-supplemented and uninfected controls. Birds that received standard diet with no egg powder supplementation and given necrotic enteritis infection served as non-supplemented and infected controls. All the birds were given a low protein diet to 19 days of age and switched to a high protein diet to facilitate development of necrotic enteritis. Values with no common letter differ significantly (P≤0.05). IC=infected control; NE-B=*Clostridium perfringens* elongation factor Tu; NE-C=*Clostridium perfringens* necrotic enteritis B-like (NetB) toxin; Cocci-E=*Eimeria tenella* elongation factor 1-alpha; Cocci-P=*Eimeria tenella* 3-1E profilin.
Figure 14:
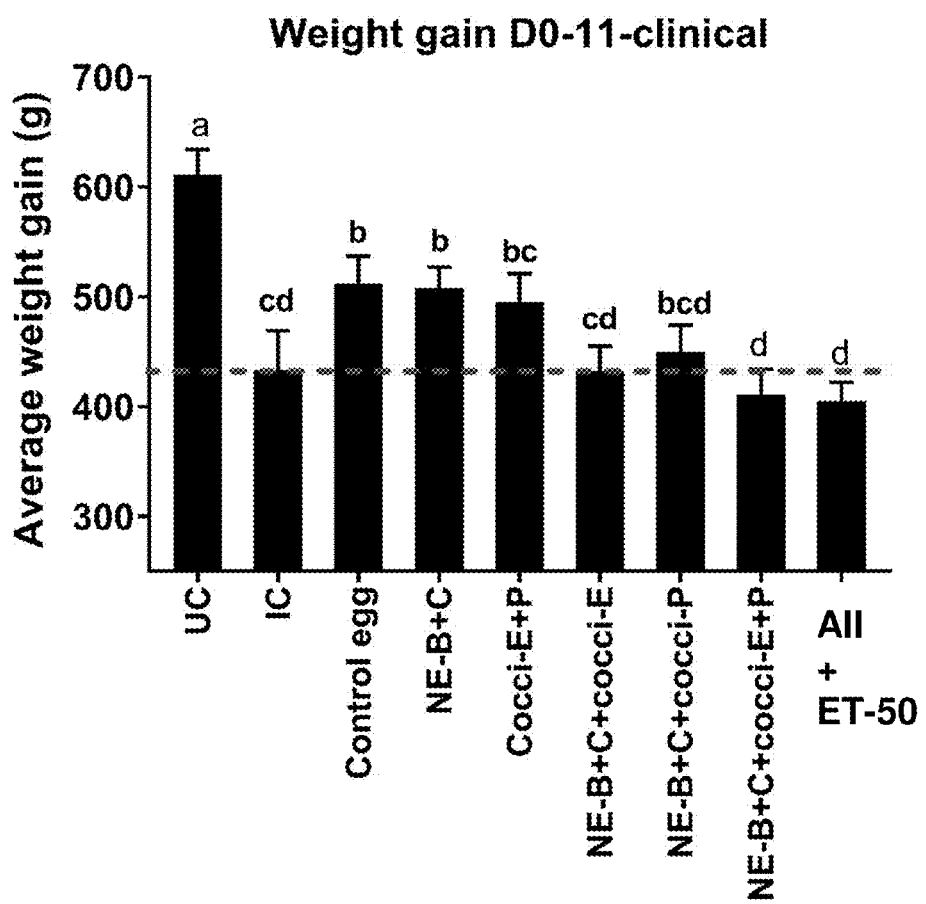
FIG. 14 shows body weight gain (mean±SEM) from Day 0 (day of *E. maxima* infection) to Day 11 (7 days post-*Clostridium perfringens* infection) in a clinical model of necrotic enteritis infection. *E. maxima* infection was performed at 15 days of age and *Clostridium perfringens* infection at 19 days of age. Birds were fed feed supplemented with different egg powders at 0.1% level from 7 days before *Eimeria* infection. Birds that received standard diet with no egg powder supplementation served as non-supplemented and uninfected controls. Birds that received standard diet with no egg powder supplementation and given necrotic enteritis infection served as non-supplemented and infected controls. All the birds were given a low protein diet to 19 days of age and switched to a high protein diet to facilitate development of NE. Values with no common letter differ significantly (P≤0.05). UC=untreated control; IC=infected control; NE-B=*Clostridium perfringens* elongation factor Tu; NE-C=*Clostridium perfringens* necrotic enteritis B-like (NetB) toxin; Cocci-E=*Eimeria tenella* elongation factor 1-alpha; Cocci-P=*Eimeria tenella* 3-1E profilin.

The 0.1% dose of the B+C (*C. perfringens* elongation factor Tu (B) and NetB toxin (C) antibodies) and All+ET-50 treatments significantly reduced lesion score 2 days after infection with a subclinical level of *C. perfringens* relative to the uninfected control. FIG. 6 and Table 8. The 0.1% dose of the B+C and B+C+Co1 treatments significantly increased weight gain from Day 0 (day of *Eimeria* infection) to Day 6 (2 days after *C. perfringens* infection) relative to the infected control for the subclinical level of *C. perfringens* infection. FIGS. 8 and 9 and Table 10. At Day 11 (7 days after *C. perfringens* infection) the B+C treatment significantly increased weight gain relative to the infected control for the clinical infection level. See FIGS. 14 and 15 and Table 13.

TABLE 8

Raw data for lesion scores (2 days post *Clostridium perfringens*-challenge) - subclinical infection Lesion Score - day 2 post challenge (subclinical)

|  | Uninfected control | Infected control | Control egg | B + C | Co1 + Co2 | B + C + Co1 | B + C + Co2 | B + C + Co1 + Co2 | All + ET-50 |
|---|---|---|---|---|---|---|---|---|---|
|  | 0 | 2 | 1 | 1 | 0 | 2 | 1 | 1 | 1 |
|  | 0 | 2 | 1 | 1 | 1 | 2 | 0 | 1 | 2 |
|  | 0 | 1 | 1 | 1 | 2 | 1 | 2 | 1 | 1 |
|  | 0 | 4 | 1 | 2 | 2 | 2 | 3 | 1 | 0 |
|  | 0 | 2 | 2 | 0 | 1 | 1 | 2 | 3 | 1 |
|  | 0 |   | 1 |   | 2 | 2 | 1 |   |   |
| Average | 0 | 2.2 | 1.2 | 1.0 | 1.3 | 1.7 | 1.5 | 1.4 | 1.0 |

TABLE 9

Raw data for lesion scores (2 days post *Clostridium perfringens*-challenge) - clinical infection Lesion Score - day 2 post challenge (clinical)

|  | Uninfected control | Infected control | Control egg | B + C | Co1 + Co2 | B + C + Co1 | B + C + Co2 | B + C + Co1 + Co2 | All + ET-50 |
|---|---|---|---|---|---|---|---|---|---|
|  | 0 | 3 | 3 | 4 | 3 | 3 | 3 | 3 | 2 |
|  | 0 | 3 | 4 | 0 | 1 | 2 | 2 | 3 | 2 |
|  | 0 | 4 | 2 | 2 | 1 | 3 | 1 | 2 | 2 |
|  | 0 | 3 | 2 | 4 | 3 | 1 | 2 | 1 | 2 |
|  | 0 | 2 | 2 | 3 | 2 | 3 | 2 | 3 | 2 |
|  | 0 | 2 | 2 | 3 | 2 | 2 | 3 | 2 | 2 |
| Average | 0 | 2.8 | 2.5 | 2.7 | 2.0 | 2.3 | 2.2 | 2.3 | 2.0 |

TABLE 10

Raw data for body weight gain Day 0 (day of *Eimeria* infection) to Day 6 (2 days post *Clostridium perfringens*-challenge)-subclinical infection Weight gain (g)day 0-6 post challenge (subclinical)

| Uninfected control | Infected control | Control egg | B + C | Co1 + Co2 | B + C + Co1 | B + C + Co2 | B + C + Co1 + Co2 | All + ET-50 |
|---|---|---|---|---|---|---|---|---|
| 330 | 125 | 128 | 209 | 264 | 252 | 247 | 183 | 150 |
| 322 | 227 | 202 | 162 | 135 | 175 | 181 | 173 | 268 |
| 328 | 139 | 221 | 146 | 167 | 179 | 208 | 194 | 260 |
| 343 | 201 | 223 | 190 | 201 | 180 | 211 | 129 | 168 |
| 207 | 138 | 207 | 229 | 226 | 204 | 184 | 201 | 141 |
| 239 | 125 | 222 | 175 | 202 | 248 | 190 | 130 | 206 |
| 240 | 164 | 200 | 127 | 124 | 263 | 146 | 113 | 173 |
| 317 | 191 | 163 | 245 | 172 | 208 | 175 | 183 | 248 |
| 163 | 148 | 214 | 137 | 268 | 195 | 197 | 214 | 157 |
| 340 | 199 | 188 | 218 | 152 | 191 | 147 | 148 | 205 |
| 267 | 119 | 195 | 214 | 248 | 170 | 171 | 171 | 179 |
| 300 | 179 | 203 | 254 | 185 | 193 | 162 | 231 | 204 |
| 277 | 131 | 106 | 205 | 157 | 140 | 198 | 103 | 247 |
| 231 | 118 | 227 | 212 | 138 | 181 | 203 | 177 | 153 |
| 310 | 177 | 233 | 315 | 125 | 197 | 121 | 162 | 142 |
| 236 | 160 | 204 | 216 | 229 | 191 | 180 | 149 | 164 |
| 252 | 134 | 229 | 179 | 203 | 144 | 155 | 193 | 192 |
| 304 | 255 | 168 | 150 | 160 | 262 | 177 | 152 | 219 |

TABLE 10-continued

Raw data for body weight gain Day 0 (day of *Eimeria* infection) to Day 6
(2 days post *Clostridium perfringens*-challenge)-subclinical infection Weight gain (g)day 0-6 post challenge (subclinical)

| | Uninfected control | Infected control | Control egg | B + C | Co1 + Co2 | B + C + Co1 | B + C + Co2 | B + C + Co1 + Co2 | All + ET-50 |
|---|---|---|---|---|---|---|---|---|---|
| | 268 | 191 | 243 | 241 | 162 | 206 | 186 | | 204 |
| | 278 | 211 | 229 | 272 | 139 | 87* | 181 | | 208 |
| | 311 | | 111 | | 213 | 228 | 220 | | |
| Average | 279 | 167 | 196 | 205 | 184 | 200 | 183 | 167 | 194 |

UC—Uninfected control;
IC—Infected control
*removed as outlier

TABLE 11

Raw data for body weight gain from Day 0 (day of *Eimeria* infection) to Day
6 (2 days post *Clostridium perfringens*-challenge) - clinical infection.

Weight gain (g)day 0-6 post challenge (clinical)

| | Uninfected control | Infected control | Control egg | B + C | Co1 + Co2 | B + C + Co1 | B + C + Co2 | B + C + Co1 + Co2 | All + ET-50 |
|---|---|---|---|---|---|---|---|---|---|
| | 330 | 130 | 215 | 246 | 240 | 192 | 232 | 206 | 190 |
| | 322 | 177 | 285 | 224 | 186 | 189 | 172 | 188 | 261 |
| | 328 | 225 | 122 | 186 | 146 | 199 | 149 | 166 | 188 |
| | 343 | 156 | 246 | 268 | 150 | 273 | 123 | 172 | 165 |
| | 207 | 155 | 156 | 132 | 201 | 220 | 222 | 186 | 120 |
| | 239 | 194 | 268 | 255 | 219 | 195 | 157 | 142 | 119 |
| | 240 | 183 | 194 | 146 | 303 | 169 | 126 | 107 | 129 |
| | 317 | 141 | 135 | 86* | 237 | 163 | 221 | 252 | 243 |
| | 163 | 226 | 265 | 160 | 277 | 193 | 246 | 149 | 86* |
| | 340 | 165 | 144 | 173 | 221 | 159 | 222 | 266 | 175 |
| | 267 | 215 | 115 | 188 | 233 | 282 | 165 | 84* | 94* |
| | 300 | 15* | 280 | 190 | 141 | 108 | 231 | 178 | 168 |
| | 277 | 226 | 186 | 100 | 145 | 204 | 168 | 222 | 132 |
| | 231 | 153 | 174 | 107 | 187 | 121 | 261 | 159 | 140 |
| | 310 | 193 | 153 | 182 | 216 | 161 | 123 | 152 | 173 |
| | 236 | 118 | 226 | 156 | 156 | 168 | 116 | 180 | 165 |
| | 252 | 250 | 154 | 207 | 103 | 244 | 241 | 169 | 123 |
| | 304 | 170 | 184 | 218 | 258 | 164 | 169 | 168 | 106 |
| | 268 | | 235 | 215 | 213 | 126 | 118 | 147 | 149 |
| | 278 | | 130 | 221 | | 198 | 163 | 237 | 214 |
| | 311 | | | 169 | | | 251 | 155 | |
| Average | 279 | 181 | 193 | 187 | 202 | 186 | 184 | 180 | 164 |

UC—Uninfected control;
IC—Infected control
*removed as outlier

TABLE 12

Raw data for body weight gain Day 0 (day of *Eimeria* infection) to Day 11
(7 days post *Clostridium perfringens*-challenge)-subclinical infection Weight gain (g)day 0-11 post challenge (subclinical)

| Uninfected control | Infected control | Control egg | B + C | Co1 + Co2 | B + C + Co1 | B + C + Co2 | B + C + Co1 + Co2 | All + ET-50 |
|---|---|---|---|---|---|---|---|---|
| 686 | 282 | 506 | 436 | 621 | 531 | 546 | 469 | 379 |
| 671 | 524 | 539 | 577 | 339 | 447 | 499 | 497 | 620 |
| 654 | 342 | 558 | 536 | 522 | 523 | 540 | 401 | 366 |
| 687 | 534 | 453 | 411 | 490 | 524 | 396 | 411 | 470 |
| 447 | 522 | 475 | 452 | 311 | 620 | 475 | 464 | 383 |
| 671 | 422 | 460 | 472 | 620 | 89* | 438 | 444 | 603 |
| 747 | 466 | 530 | 502 | 367 | 436 | 478 | 453 | 465 |
| 540 | 536 | 509 | 576 | 555 | 477 | 352 | 590 | 426 |
| 643 | 378 | 474 | 496 | 403 | 393 | 340 | 262 | 459 |

TABLE 12-continued

Raw data for body weight gain Day 0 (day of *Eimeria* infection) to Day 11
(7 days post *Clostridium perfringens*-challenge)-subclinical infection Weight gain (g)day 0-11 post challenge (subclinical)

| | Uninfected control | Infected control | Control egg | B + C | Co1 + Co2 | B + C + Co1 | B + C + Co2 | B + C + Co1 + Co2 | All + ET-50 |
|---|---|---|---|---|---|---|---|---|---|
| | 481 | 312 | 475 | 698 | 536 | 501 | 339 | 370 | 291 |
| | 699 | 456 | 538 | 492 | 337 | 390 | 268 | 405 | 358 |
| | 514 | 613 | 553 | 553 | 330 | 402 | 355 | 288 | 454 |
| | 528 | 464 | 341 | 615 | 511 | 610 | 455 | | 474 |
| | 623 | 486 | 584 | | | 458 | 418 | | |
| | 577 | | 476 | | | 563 | 531 | | |
| Average | 611 | 453 | 498 | 524 | 457 | 491 | 428 | 421 | 442 |

UC—Uninfected control;
IC—Infected control
*removed as outlier

TABLE 13

Raw data for body weight gain Day 0 (day of *Eimeria* infection) to Day 11 (7 days post *Clostridium perfringens*-challenge)-clinical infection Weight gain (g)day 0-11 post challenge (clinical)

| | Uninfected control | Infected control | Control egg | B + C | Co1 + Co2 | B + C + Co1 | B + C + Co2 | B + C + Co1 + Co2 | All + ET-50 |
|---|---|---|---|---|---|---|---|---|---|
| | 686 | 362 | 514 | 533 | 571 | 436 | 499 | 444 | 412 |
| | 671 | 451 | 587 | 519 | 264 | 399 | 400 | 477 | 567 |
| | 654 | 253 | 559 | 497 | 402 | 501 | 443 | 292 | 424 |
| | 687 | 425 | 586 | 545 | 518 | 581 | 11* | 328 | 386 |
| | 447 | 59* | 517 | 635 | 667 | 385 | 545 | 300 | 362 |
| | 671 | −31* | 629 | 72* | 551 | 303 | 458 | 502 | 472 |
| | 747 | 527 | 407 | 515 | 566 | 469 | 513 | 310 | 414 |
| | 540 | 371 | 598 | 474 | 481 | 433 | 413 | 624 | 432 |
| | 643 | 507 | 475 | 381 | 496 | 462 | 512 | 488 | 293 |
| | 481 | 566 | 300 | 368 | 437 | 313 | 539 | 405 | 325 |
| | 699 | | 524 | 551 | 495 | 303 | 241 | 339 | 392 |
| | 514 | | 447 | 526 | 481 | 548 | 560 | 400 | 400 |
| | 528 | | 515 | 520 | 506 | 455 | 364 | 415 | 390 |
| | 623 | | | 533 | | | 463 | 353 | 413 | 398 |
| | 577 | | | | | | | 459 | 428 | |
| Average | 611 | 433 | 512 | 508 | 495 | 432 | 450 | 411 | 405 |

UC—Uninfected control;
IC—Infected control
*removed as outlier

Example 4—Hyperimmunization of Laying Hens and Determination of IgY Titers

Cloning, Expression and Purification of Recombinant *Clostridium perfringens* Antigens for Hyperimmunization The procedures for the production of recombinant proteins for immunization of hens followed ones previously described (Jang et al., 2012, Vaccine 30:5401-5406; Lee et al., 2011, Res. Vet. Sci. 91:e80-86). Briefly, full-length coding sequences of *Clostridium perfringens* α-toxin (Antigen A), NetB toxin (Antigen B), EF-Tu (Antigen C) and partial sequence of PFO (Antigen D) were cloned into the pET32a(+) vector with an $NH_2$-terminal polyhistidine tag and transformed into *Escherichia coli*. Transformed *E. coli* DH5α bacteria were grown to mid-log phase (16 h at 37° C.), induced with 1.0 mM of isopropyl-β-d-thiogalactopyranoside (Amresco, Cleveland, Ohio) for 5 h at 37° C. The bacteria were then harvested by centrifugation and disrupted by sonication on ice (Misonix, Farmingdale, N.Y.). The supernatant was incubated with Ni-NTA agarose (Qiagen, Valencia, Calif.) for 1 h at room temperature (RT) and the resin washed with PBS. Purified Clostridial proteins were eluted and the purity confirmed on Coomassie blue-stained SDS-acrylamide gels.

Immunization of Laying Hens.

Laying hens were immunized with 50 μg of the purified *Clostridium perfringens* recombinant protein as a subcutaneous/intramuscular injection.

Determination of Antigen-Specific IgY Titers in Egg and Spray Dried Egg Powder

Egg samples collected from immunized and unimmunized hens at regular intervals were used to monitor the specific antibody titers. Total IgY was extracted from eggs using PIERCE™ Chicken IgY Purification Kit (Thermo Fisher Scientific, Waltham, Mass.). Briefly, 2 mL of egg was mixed with five volumes of delipidation reagent and IgY was purified following the manufacturer's instructions. Spray dried egg powder samples were reconstituted in sterile PBS at 1 mg/mL conc., filtered through 0.22 μm membrane filter. Specific antibody titers in the isolated IgY or egg powder samples were measured by ELISA. Flat bottom, 96-well microtiter plates (Corning® Costar®, Corning, N.Y.) were coated with purified recombinant *Clostridium perfringens* proteins (A, E, N, P) at 10 μg/mL conc. (100 μL/well) and incubated overnight at 4° C. The plates were washed twice with PBS containing 0.05% Tween 20 (Sigma-Aldrich, St. Louis, Mo.) and blocked with 100 μL/well of PBS containing 1% Bovine Serum Albumin (BSA) and incubated for 1 h at RT. Serially diluted (in PBS with 0.1% BSA) IgY samples from egg or egg powder samples were added to the plates in triplicate wells (100 μL/well) and incubated for 2 h at RT with constant shaking. The plates were then washed with PBS-T and treated with peroxidase-conjugated rabbit anti-chicken IgY (IgG) antibody (1:500; Sigma), incubated for 30 min, followed by color development for 10 minutes with 0.01% tetramethylbenzidine substrate (Sigma) in 0.05 M Phosphate-Citrate buffer, pH 5.0. Bound antibodies were detected by measuring optical density at 450 nm ($OD_{450}$) using a microplate reader (Bio-Rad, Hercules, Calif.).

Antibody Titers in Eggs of Hyperimmunized Hens

The average antibody titers in the eggs of hyperimmunized hens is shown in FIG. 16. The birds showed significantly higher antibody titers, to the respective antigen they were immunized with, in the egg compared to those from unimmunized controls.

Antibody Titers of Spray Dried Egg Powder

The specific antibody titers in the spray dried egg powder as determined by ELISA are shown in FIG. 17. The different egg powders produced showed significantly higher antibody titers compared to that of the spray dried control egg powder.

Example 5—Efficacy of a 1% Dose of Hyperimmune Egg Powder Against Necrotic Enteritis in Broiler Chickens Infected with Clinical Levels of *C. perfringens*

Production of *Clostridium perfringens*-Specific Egg IgY Antibodies

IgY antibodies were raised in laying hens by hyperimmunizing with at least one of four different antigens of *Clostridium perfringens*: α-toxin (Antigen A), Elongation Factor Tu (EF-Tu, Antigen B), NetB toxin (Antigen C), and Pyruvate: Ferredoxin oxidoreducatse (PFO, Antigen D) alone or all 4 antigens pooled and given as a booster injection 2 weeks later. Eggs were collected and the antibody titers were monitored by ELISA at regular intervals. After demonstration of increasing specific antibody titers in the eggs, eggs were collected, homogenized and then spray dried. The resultant egg powder was used as a source of protective antibodies and control powder was obtained from eggs collected from unimmunized hens.

Evaluation of Protective Immunity

Two independent in vivo trials were conducted to evaluate the protective effect of hyperimmune IgY against experimentally induced NE infection in chickens. Body weight gain and lesion scores were used as the criterion to judge the protective efficacy of the antibodies. All the experiments were approved by the Beltsville Agriculture Research Center Small Animal Care and Use Committee and the husbandry followed guidelines for the care and use of animals in agriculture research (FASS, 1999).

Experiment 1

Day (d) old broiler chicks (n=120) (Ross/Ross, Longenecker's Hatchery, Elizabethtown, Pa.) were obtained and housed in brooder units in *Eimeria*-free facility for two weeks. Birds were then transferred to finisher cages where they were infected and kept until the end of the experimental period. Feed and water were provided ad libitum. At 17 d of age, birds were randomly assigned to one of the 8 treatments (15 birds/trt). Birds in treatment 1 were uninfected and given non-supplemented standard diet (control). Birds in treatments 2-8 were co-infected with *Eimeria maxima/Clostridium perfringens* to experimentally induce NE and were provided with either a non-supplemented diet (treatment 2) or diets supplemented with control egg powder (treatment 3) or egg powders from immunized hens as shown in table 14 below at the 1% level.

TABLE 14

Experimental Design for Experiment 1

| Treatment | Description | Type of egg powder | NE infection |
|---|---|---|---|
| 1 | Uninfected control | — | No |
| 2 | Infected & non-supplemented | — | Clinical |
| 3 | Infected | Control powder (1%) | |
| 4 | Infected | A (1%) | |
| 5 | Infected | B (1%) | |
| 6 | Infected | C (1%) | |
| 7 | Infected | D (1%) | |
| 8 | Infected | A + B + C + D (1%) | |

The experimental model used for necrotic enteritis induction included oral inoculation of birds at 17 d of age with *E. maxima* strain 41A ($1\times10^4$ oocysts/bird) followed by oral gavage with *Clostridium perfringens* strain Del-1 (1×109 CFU/bird) four days after *Eimeria* infection (d 23 of age). To facilitate the development of necrotic enteritis, all the birds were given an antibiotic-free certified organic starter diet containing low level (16%) of crude protein from d 1 to 17 and then switched to a standard grower diet with high crude protein levels (24%) from d 23 to the end of the experiment. Feeding of diets supplemented with egg powders (control powder/powder B/powder C) at 1% level commenced from 17 d of age (day of *Eimeria* infection) to the end of the experiment. Birds were weighed individually on d 17 (the day of *Eimeria* infection/four days before *Clostridium perfringens* infection) and on d 30 (7 days after *Clostridium perfringens* infection) and weight gains were calculated. Three birds per treatment group were randomly selected, euthanized and approximately 20 cm intestinal segments extending 10 cm anterior and posterior to the Meckel's diverticulum were obtained on d 23 (2 days after *Clostridium perfringens* infection). Intestinal sections were scored for NE lesions on a scale of 0 (none) to 4 (high) in a blind fashioned way by three independent observers (Cooper and Songer, 2009; Prescott, 1979).

Experiment 2

Husbandry for the birds in this experiment followed procedures previously described for experiment 1. Fifty broiler chickens were randomly assigned to one of the 5 treatments (10 birds/trt) at 17 d of age. Birds in treatment 1 were uninfected and given non-supplemented standard diet (control). Birds in treatments 2-5 were co-infected with *Eimeria maxima/Clostridium perfringens* to experimentally induce necrotic enteritis and were provided with either a non-supplemented diet (treatment 2) or diets supplemented with control egg powder (treatment 3) or the egg powders shown in Table 15 below at the 1% level.

TABLE 15

Experimental Design for Experiment 2

| Treatment | Description | Type of egg powder | NE infection |
|---|---|---|---|
| 1 | Uninfected control | — | No |
| 2 | Infected & non-supplemented | — | Clinical |
| 3 | Infected | Control powder (1%) | |
| 4 | Infected | B (1%) | |
| 5 | Infected | C (1%) | |

The procedures for induction of necrotic enteritis were similar to the ones described for experiment 1. Birds were weighed individually on d 17 (the day of *Eimeria* infection/ four days before *Clostridium perfringens* infection) and on d 30 (7 days after *Clostridium perfringens* infection) and weight gains were calculated. Blood samples (n=3/treatment) were collected form the wing vein 6 hr following inoculation with *Clostridium perfringens* and sera were separated by centrifugation at 1000 rpm for 20 min.

Capture ELISA for Determination of Serum α-Toxin or NetB Toxin Levels

Serum samples from experiment 2 were used to determine the levels of α-toxin and NetB toxin by ELISA and the procedures followed have previously been described (Lee et al., 2013, Brit. J. Nutr. 110:840-847). Briefly, mAb to α-toxin or NetB toxin were coated onto 96 well microtiter plates at a concentration of 0.5 ag/well and incubated overnight at 4° C. The plates were washed and blocked as described previously. Serum samples (100 µL/well) were added and the plates incubated at 4° C. overnight. Following incubation, the plates were washed and treated with unconjugated rabbit polyclonal antibody to α-toxin or NetB (0.2 g/well), incubated at RT for 30 min. After washing the plates for 5 times, 100 µL/well of second detection antibody (anti-rabbit IgG HRP conjugated, 1:10,000) was added, incubated for 30 minutes, followed by color development with substrate. Optical density (OD) was determined at 450 nm with a microplate reader (Bio-Rad, Richmond, Calif.).

In Vitro IgY-NetB Toxin Neutralization Assay

LMH cytotoxicity assay outlined by Keyburn et al. (2008) was used to assess the neutralizing activity of anti-NetB hyperimmune IgY against recombinant NetB protein. LMH cells were added to 96 well tissue culture plates (Corning) (5000 cells/well in 100 µL Waymouth's medium) and pre incubated for 24 h at 37° C. and 5% $CO_2$. IgY antibodies isolated from eggs of unimmunized hens and from those of hens hyperimmunized with *Clostridium perfringens* ag-N were incubated with recombinant NetB protein (toxin to IgY ratio-1:20) for 1 h at RT. The pre-incubated IgY-toxin mixtures and NetB alone (390 µg/well) were added to LMH cells in triplicate wells and incubated for 4 h at 37° C. The dehydrogenase activity in the viable cells was measured with Cell Counting Kit-8 (Dojindo Molecular Technologies, Rockville, Md.) and used to calculate the % cytotoxicity.

*Clostridium perfringens* Growth Inhibition Assay

The efficacy of IgY from hens hyperimmunized with elongation factor Tu (EF-Tu, Antigen B) on inhibiting the growth of *Clostridium perfringens* in culture was investigated and compared to that of control IgY. *Clostridium perfringens* Del-1 strain was anaerobically grown in BHI broth (Becton Dickinson, N.J.) overnight at 37° C. Specific and non-specific IgY solutions were sterilized by filtering through 0.22 m membrane filter. Five mL of each IgY solution was then added to equal volume of *Clostridium perfringens* culture ($2.4 \times 10^7$ CFU/mL) and incubated in anaerobic conditions at 37° C. The final conc. of the IgY tested include 1 mg/mL. Samples (1 mL) were taken at 0, 2, 4, 6 and 24 h and serial dilutions were plated on *Perfringens* agar plates in duplicates (Thermo Scientific, Lenexa, Kans.). The inoculated plates were incubated at 37° C. for 24 hrs and the colonies were counted to determine the total no. of CFU/mL of sample.

Statistical Analysis

Statistical analysis was carried out using SAS software (version 9.4, SAS Institute Inc., Cary, N.C.). All the data were expressed as mean±SEM for each treatment. The data were analyzed by one-way ANOVA and the means separated by Duncan's multiple range test. Results were considered to be significantly different if $P \le 0.05$.

Results

Experiment 1—Body Weight Gain

The body weight gain results from experiment 1 (day of EM challenge to d7 post *Clostridium perfringens* challenge; 11 day interval) are shown in FIG. 18. The NE infected birds on non-supplemented diets (NE+None) showed significantly lower body weight gain compared to that of uninfected controls on non-supplemented diet. Supplementation of the diets with 1% egg powders B, C, D, and B+C+D protected birds from NE challenge as shown by significantly increased body weight gain compared to that of birds on non-supplemented diets or birds treated with control egg powder.

Experiment 1—Lesion Scores

Supplementation of diets with egg powder B or egg powder C protected birds from NE challenge as shown by the significant reduction in lesion scores following experimental NE challenge relative to birds on non-supplemented diets (FIG. 19).

Experiment 2-Body Weight Gain

The results looked similar to that of experiment 1 and the body weight gain of birds fed with egg powders B and C was significantly higher compared to those fed control egg powder. In fact body weight gain of birds fed egg powders B and C was equal to that of the control uninfected birds (FIG. 20).

Experiment 2-Serum α-Toxin or NetB Toxin Levels

The α-toxin or NetB toxin were not detected in the serum from control group (data not shown). The levels of both α-toxin and NetB in the serum of NE infected birds receiving diets with egg powder B or egg powder C were significantly lower compared to those of birds receiving control egg powder or non-supplemented diet (FIG. 21). However, a significant reduction in serum toxin levels was observed in the birds that received control egg powder compared to the infected controls.

In Vitro Toxin Neutralization

The toxin neutralization ability of hyperimmune IgY raised against NetB toxin (Antigen C) is shown in FIG. 22. Preincubation of NetB toxin with NetB specific hyperimmune IgY neutralized the cytotoxic effect of the toxin as shown by reduced cytotoxicity (12%) as opposed to toxin alone controls (66%). Incubation with IgY from unimmunized hens did not neutralize the toxin.

Clostridium perfringens Growth Inhibition

The results of Clostridium perfringens growth inhibition are shown in FIG. 23. Neither the control IgY nor IgY raised against Clostridium perfringens elongation factor Tu (Antigen B) showed any inhibitory effect on *Clostridium perfringens* growth at the concentration tested.

Example 6—Hyperimmune Egg Antibodies Against Coccidian Parasites

Avian coccidiosis is caused by several distinct species of *Eimeria* protozoa and is the major parasitic disease of poultry of economic importance. As an alternative strategy to control avian coccidiosis without using prophylactic medications, we investigated the efficacy of inducing passive immunity against coccidiosis by orally feeding hyperimmune IgY antibodies. Before in vivo treatment to chicks, three kinds of eggs from hens with PBS or three major proteins which are major antigens against coccidiosis, profilin, MIC2, or Gam82, were spray-dried and solubilized in PBS buffer.

In this study, we hypothesized that passive immunization with egg powder containing hyperimmune anti-coccidia IgY antibodies to young chicks would confer protection against other species of *Eimeria*. To verify this hypothesis, we continuously fed young chicks egg powders that contain high levels of hyperimmune IgY antibodies against profilin, MIC2, or Gam82 from hatch and the efficacy of passive immunity was evaluated by infecting these chicks orally with *E. maxima* oocysts.

Cloning of Profilin, MIC2, and Gain 82 Gene

The 3-1E (profilin) gene was cloned by immunoscreening an *E. acervulina* cDNA library with a rabbit antiserum against *E. acervulina merozoites* (Lillehoj et al., 2000, Avian Dis. 44:379-389; Lillehoj et al., 2005, Avian Dis. 49: 112-117). This 3-1E profilin gene is highly conserved between *E. acervulina* and *E. tenella*, e.g. the sequence of the 3-1E profilin protein is the same in both species. EaProfilin cDNA was amplified by PCR (GenBank accession number; AY660553.1). The 1086-base pair profilin cDNA was subcloned into the pcDNA expression vector (Invitrogen, Carlsbad, Calif.), as described (Song et al., 2000, Vaccine 19: 243-252; Lillehoj et al., 2005, Avian Dis. 49: 112-117). The recombinant profilin-pcDNA plasmid was transformed into *Escherichia coli* DH5a, bacteria was grown overnight to mid-log phase, and plasmid DNA was purified using a commercial kit (Qiagen, Valencia, Calif.), according to the manufacturer's instructions.

EtMIC2 cDNA synthesized from *E. tenella* was amplified by PCR using the following primers (GenBank accession number AF111839) (Ding et al., 2005, Vaccine 23: 3733-3740). Amplicons were digested with BamHI and Sail, cloned into pGEX-6p-3 (Amersham Biosciences, Piscataway, N.J.), and recombinant EtMIC2-pGEX clones confirmed by sequence analysis. The EtMIC2 coding sequence was subcloned into the BamHI/SalI sites of pcDNA3.1 (Invitrogen), transformed into *E. coli* DH5α, recombinant plasmids purified (Qiagen, Valencia, Calif.), and quantified spectrophotometrically.

The cDNA from *E. maxima* was prepared using Thermoscript reverse transcriptase (Invitrogen) with a Gam82-specific reverse primer (Jang et al., 2010, Vaccine 28: 2980-2985). The Gam82 coding sequence was amplified by PCR using Proof Start DNA polymerase (Qiagen, Valencia, Calif.) with the following primer sequences containing Bam HI and Not I restriction enzyme sites (underlined): forward, 5_-AGCTGGATCCACCAGCTCTGGCCAGGATCAGGTG-3_; reverse: 5_-TCTAGAGCGGCCGCTGCCCACATCTCTGATTGTTC-3_. Amplicons were cloned into the pET28a (+) plasmid vector (Novagen/EMD Chemicals, Gibbstown, N.J.) downstream from an NH2-terminal His6 epitope tag, plasmid clones were verified by sequence analysis, and used to transform competent *Escherichia coli* BL21 Star (Invitrogen).

Expression and Purification of Recombinant Antigens

Recombinant *E. coli* were induced for 4 h with 0.75 mM IPTG (Bangalore Genei, Bangalore, India) at OD600=0.6, the cells harvested by centrifugation, and lysed with 10_g/ml of lysozyme (Sigma-Aldrich, St. Louis, Mo.) and sonication (Vibra-Cell, Sonics & Materials, Inc., Newtown, Conn.) (Lillehoj et al., 2005; Ding et al., 2005, Jang et al., 2010). The lysate was applied to a $Ni2^{+}$-chelating affinity column (HiTrap, GE Healthcare, Piscataway, N.J.), the column was washed with PBS, pH 7.0 to remove unbound proteins, and bound proteins were eluted step-wise with PBS, pH 7.0 containing 0.5 or 1.0 M imidazole (Sigma). The eluted protein fractions were visualized on 10% SDS-acrylamide gels stained with Coomassie brilliant blue and on Western blots probed with horseradish peroxidase-conjugated anti-His monoclonal antibody (1:3000; Qiagen), and stored at −20° C.

Immunization of Chickens and Preparation of Lyophilized Egg Powder

Eighteen week-old Specific-pathogen-free (SPF) hens were distributed into four groups (n=5/group) and were provided ad libitum access to feed and water. A water-in-oil emulsion was prepared by mixing 500 al of PBS alone or PBS containing 100 ag of each recombinant protein, profilin, MIC2, or Gam82 with 500 μl of Freund's complete adjuvant (Sigma, USA) for the first immunization. Each hen was intramuscularly injected at four sites in breast muscles with a total of 1,000 al of the emulsion (250 al per site). Booster immunizations were given at 2, 4, 8, 12, 18, 24, and 30 weeks after the first immunization with Freund's incomplete adjuvant (Sigma) emulsified with 100 ag of each recombinant protein. Eggs were collected daily for 0 week pre-immunization and up to 8 weeks postimmunization, wiped with 70% ethanol, and stored at 4° C. until further processing. The eggs were broken and the liquid contents pooled and mixed to a homogeneous state. The liquid pool was thermal-treated at 57.2° C. for 30 min, and then spray-dried at 66.1° C. outlet.

Specific Activity and Cross-Reactivity of IgYs

The specific activity and cross-reactivity of IgY was monitored by the enzyme linked immunosorbent assay (ELISA) procedure optimized in previous studies (Lee et al., 2013, Br J Nutr. 110: 840-847; Kassim et al., 2012, J Microbiol Biotechnol 22: 1423-1431). The wells of 96-well microtiter plates were coated with 100 μl of profilin, MIC2, or Gam 82 at 2 ag/ml in carbonate buffer (pH 9.6). Two hundred microliter of 1% skimmed milk in PBS was used to block the uncoated surface. One hundred microliter of anti-profilin, anti-MIC2, or anti-Gam 82 IgYs at 10 ag/ml in PBS was used as primary antibody for the analysis of specific activity and cross-reactivity of IgYs. One hundred microliter of rabbit anti-chicken IgG conjugated with horseradish peroxidase (Sigma-Aldrich) diluted 1:10,000 in PBS was used as a secondary antibody. One hundred microliter of 0.1M citrate buffer (pH 4.0) containing 0.025% ABTS and 0.03% $H_2O_2$ was used for color development. The absorbance was measured at 450 nm using a microplate reader ELx800 (BioTek Instruments Inc., Vermont, USA). The cross-reactivity was assessed by comparing the optical density obtained when the produced IgYs were used with non-corresponding antigen coated, with those of corresponding antigens.

Experimental Diets and Infection

One hundred fifty one-day-old broilers were randomly assigned to 10 groups (15 birds/group, 7-8 birds/unit) in electrically heated 2 battery units per group. Two groups (uninfected and infected controls) were fed a normal standard diet and 8 groups were fed the diets supplemented with 0.2% and 0.5% egg powders (C0.2, C0.5) from PBS-treated hens, 0.2% and 0.5% egg powders (P0.2, P0.5) from profilin-treated hens, 0.2% and 0.5% egg powders (M0.2, M0.5) from MIC2-treated hens, or 0.2% and 0.5% egg powders (G0.2, G0.5) (v/v) from Gam82-treated hens. At 7 days post-hatch, the infected control group and egg powder-supplemented groups were orally challenged with $5.0 \times 10^3$ sporulated E. maxima oocysts.

Body Weights, Fecal Oocyst Output, and Lesion Score

Body weights were measured at 0 (pre-infection) (n=15) and 10 days post-infection (dpi) (n=10). For determination of fecal oocyst output, birds were placed in oocyst collection cages (2 birds/cage) and fecal samples were collected between 5 and 10 dpi as described (Lee et al., 2013, Br. J. Nutr. 110: 840-847; Lee et al., 2013, Vet Parasitol. 197: 113-121). Oocyst numbers were determined using a McMaster chamber according to the formula: total oocysts per bird=oocyst count×dilution factor×(fecal sample volume÷counting chamber volume)÷2.

For gut lesions, birds (n=5/group) were euthanized and sacrificed by cervical dislocation at day 7 post-infection with E. maxima. Two equal intestinal sections of 10 cm located anterior and posterior to the diverticulum were collected and scored on a scale of 0 (none) to 4 (high) in a blinded fashion by three independent observers as described (Lee et al., 2013, Vet Parasitol. 197: 113-121).

Statistical Analysis

Each sample was analyzed in quadruplicate. All data were subjected to one-way analysis of variance using SPSS 15.0 for Windows (SPSS Inc., Chicago, Ill.) and were expressed as mean±SEM. The difference of mean values between the uninfected normal control and the infected control groups, and between the infected control and treatment groups was measured according to the t-test and statistical significance was considered at $P<0.05$.

Results

When antigen-specific IgY Ab titers were measured against the 3 different recombinant Eimeria proteins, their specific activities significantly increased with the increase of immunization period for profilin, MIC2, or Gam82-immunized hens and reached the highest concentration at 4-8 weeks post immunization without cross reactivity. One day-old broiler chicks were continuously fed from hatch at 0.2 and 0.5% hyperimmune IgY Ab diets (v/v), containing PBS control (C0.2, C0.5), profilin (P0.2, P0.5), MIC2 (M0.2, M0.5), and Gam82 Abs (G0.2, G0.5) for 17 days, and orally infected with $5 \times 10^3$ sporulated Eimeria maxima oocysts at 1 week of age. Eimeria infection significantly decreased body weight in the untreated control with any hyperimmune IgY diet at 17 day-old. However, all chickens fed hyperimmune IgY Ab diets significantly increased body weights ($P<0.05$) compared to the untreated infected control, and 0.5% concentration had efficiency to prevent body weight loss due to coccidiosis. The chicks fed profilin, MIC2, and Gam82 IgY diets excreted less E. maxima oocysts compared to the untreated controls, and profilin and MIC2 IgY diets significantly decreased intestinal lesions in the chickens fed those diets compared to the untreated controls ($P<0.05$). These results provide clear evidence that passive immunization of chicks with hyperimmune egg IgY antibodies against profilin, MIC2, and Gam82 provide significant protection against E. maxima infection.

Although passive transfer of maternal antibodies from hens infected with E. maxima to eggs has been shown to partially protect offsprings against E. tenella infection (Smith et al., 1994, Parasitology 109: 551-557), and an intravenously introduced mouse monoclonal antibody against a major oocyst wall protein of E. tenella (Karim et al., 1996, Infect. Immun. 64: 1227-1232) could reduce fecal oocyst output following E. tenella or E. maxima infection, these strategies do not provide a prolonged high titer antibodies to young chicks, especially at the site of infection. Therefore, a delivery strategy that can sustain high-titer antibodies in the gut secretion in order to obtain an effective control method to reduce the intestinal damage due to coccidiosis was needed. In this study, we produced three kinds of egg powders prepared from hens hyperimmunized with three major proteins which are major antigens against coccidiosis, profilin, MIC2, and Gam82, and evaluated their specific activities and protective effect against E. maxima which shows the most serious gut damages and body weight loss among major chicken parasites.

Specific Activity and Cross Reactivity of IgY

The specific activity of egg powder IgY significantly increased ($p<0.05$) with the increase of immunization period for profilin, MIC2, or Gam82-immunized hens and reached the highest concentration at 4-8 weeks post immunization (FIG. 24). The results agree with Kassim et al. (2012, J Microbiol Biotechnol. 22: 1423-1431) showing that the highest concentration of IgY reached at between 4-7 weeks from the first immunization and was maintained constantly for further three weeks of observation. Generally, the background of IgY to Gam82 was higher than other proteins, but there was no cross-reactivity found in the IgYs tested against the non-corresponding antigens (FIG. 24). Egg whites IgY didn't show any activity against all three recombinant proteins.

Effect of IgY on Body Weights, Fecal Oocyst Output, and Lesion Score

The body weight decreased in the E. maxima-infected control birds compared with the uninfected normal birds (FIG. 25). However, dietary feeding with 0.2 and 0.5% IgY enhanced body weights in the groups fed IgY-supplemented diets; 0.5% IgY diets worked better than 0.2% IgY diet on preventing body weight loss due to Eimeria infection. Feeding IgY antibodies to Eimeria proteins to young chickens resulted in a significantly higher body weight gains, almost comparable to uninfected normal control birds at 10 days post challenge infection.

Oocysts output significantly decreased at both 0.2 and 0.5% concentration of diets in the groups fed hyperimmune IgY antibodies against profilin, MIC2, and Gam82 (FIG. 26) and no difference was found on oocysts output between 0.2 and 0.5% IgY groups (C0.2 and C0.5). However, supplementation with 0.2% and 0.5% egg powders from PBS-treated hens didn't affect oocysts output.

The control group infected with E. maxima and treated without any egg powder showed the highest lesion score ($2.9 \pm 0.2$) and all egg powder IgY decreased lesion scores. However, significant decrease on lesion score was found in P0.2, P0.5, M0.2, and M0.5 groups treated with IgY against profilin or MIC2, but not IgY against Gam82. There was no significant difference was found between the IgY dose of the diets.

In the conclusion, profilin, MIC2, and Gam82 IgY diets significantly increased body weights and decreased oocyst output while intestinal lesions were significantly lowered in the groups fed profilin and MIC2 IgY diets (P<0.05). Though the effect of Gam82 IgY on lesion score looked weak compared to profilin and MIC2 IgY, these results provide clear evidence that passive immunization of chicks with hyperimmune egg IgY antibodies against profilin, MIC2, and Gam82 provide significant protection against *E. maxima* infection.

Example 7—Efficacy of 0.1%, 0.2% and 0.4% Doses of Hyperimmune Egg Powder Against Necrotic Enteritis in Broiler Chickens Infected with Subclinical Levels of *C. perfringens*

Experimental Design

The study consisted of 92 cages starting with 8 chicks each. The treatments were replicated in 8-10 blocks of 10 cages each. Two (2) additional cages of 8 birds per cage (16 birds total) were identified and marked for blood collection from treatment groups 1, 2, 3, 4, 6, and 9. The treatment groups are described below in Table 16.

TABLE 16

Treatment Groups

| | Coccidial Challenge | *Clostridium perfringens* | Cages/Trt |
|---|---|---|---|
| 1. Nonmedicated control | Day 14 | No | 10 |
| 2. Nonmedicated control | Day 14 | Day 19, 20, and 21 | 10 |
| 3. Antibiotic control, bacitracin 50 g/t | Day 14 | Day 19, 20, and 21 | 10 |
| 4. Control Egg/Not Hyperimmunized | Day 14 | Day 19, 20, and 21 | 10 |
| 5. Antigens B, C, Co1, Co2 0.1% Feed Inclusion Rate | Day 14 | Day 19, 20, and 21 | 8 |
| 6. Antigens B, C, Co1, Co2 0.2% Feed Inclusion Rate | Day 14 | Day 19, 20, and 21 | 10 |
| 7. Antigens B, C, Co1, Co2 0.4% Feed Inclusion Rate | Day 14 | Day 19, 20, and 21 | 8 |
| 8. ET-50 + Antigens B, C, Co1, Co2 0.1% Feed Inclusion Rate | Day 14 | Day 19, 20, and 21 | 8 |
| 9. ET-50 + Antigens B, C, Co1, Co2 0.2% Feed Inclusion Rate | Day 14 | Day 19, 20, and 21 | 10 |
| 10. ET-50 + Antigens B, C, Co1, Co2 0.4% Feed Inclusion Rate | Day 14 | Day 19, 20, and 21 | 8 |

Materials and Methods

A. Experimental Ration

An unmedicated chicken starter compounded with feedstuffs commonly used in the United States was formulated. The diet was representative of a local commercial formulation and calculated analyses met or exceeded NRC broiler starter requirements. Experimental treatment feeds were prepared from this basal starter feed. Treatment feeds were mixed to assure a uniform distribution of respective test article. The mixer was flushed to prevent cross contamination. Feed and water was given ad libitum. The feeds were supplemented with egg powders or bacitracin as described above in Table 16. The egg powders were prepared as described in Example 1.

B. Animals

Day of hatch (Day 0) male broiler chicks were obtained from Cobb-Vantress (Cleveland, Ga.). The chicken strain was Cobb 500. At the hatchery, the birds were sexed and received routine vaccinations. Only healthy appearing chicks were used in the study.

C. Housing

Upon arrival, chicks were raised in Petersime battery cages. At placement the birds were fed the treatment feeds. The Petersime battery cages were housed in an insulated, concrete floored, metal structure that measures 40 ft by 100 ft in a north-south direction. The floor space per animal was 0.63 sq·ft/bird. The feeder/water space per bird was 8 birds/24×3.5 inch feeder/water trough. A thermostatically controlled gas furnace/air conditioner was used to maintain uniform temperature, and even illumination was provided.

D. Disease Induction

On Day 14, all birds were orally inoculated with ~5,000 oocysts of *E. maxima*. Starting on Day 19, all birds, except Treatment Group 1 were given a broth culture of *C. perfringens* ~108 cfu/ml. The *C. perfringens* is an isolate from a clinical case of necrotic enteritis. It is both alpha toxin and net B toxin positive. The birds were administered a fresh broth culture once daily for 3 days (on Days 19, 20, and 21).

E. Necrotic Enteritis Intestinal Lesion Scoring

On Day 21, three birds from each cage were selected, sacrificed, weighed, and examined for the degree of presence of Necrotic Enteritis lesions. If fewer than three birds were present at time of scoring, all of the birds within the cage were scored. The scoring was based on a 0 to 3 score, with 0 being normal (healthy) and 3 being the most severe.

Lesion score 0=Normal
Lesion score 1=Slight mucus covering small intestine
Lesion score 2=Necrotic small intestine mucosa
Lesion score 3=Sloughed and blood small intestine mucosa and contents Results All of the egg powder treatments significantly lowered lesion scores relative to the infected control (treatment group 2) at Day 21. See Table 17. In particular, animal feed supplemented with 0.10% egg powder produced by hyperimmunization with antigens B, C, Co1, Co2, exhibited the greatest decrease in lesion score. In addition, all egg powder treatments except treatment group 8 reduced percent mortality caused by necrotic enteritis. See Table 17. Treatment groups 9 and 10 also exhibited significantly increased feed intake and weight gain relative to the infected control (treatment group 2) from Days 0 to 28. See Table 18.

TABLE 17

Necrotic Enteritis Lesion Score on Day 21 and Percent Necrotic Enteritis Mortality.

| Treatment Group | Lesion Score (0-3) | % NE Mortality |
|---|---|---|
| 1. No Additive, No CP | 0.0 d | 0.0d |
| 2. No Additive, CP | 2.0 a | 18.8a |
| 3. Bacitracin 50 g/t, CP | 1.3 bc | 9.4bc |
| 4. Egg Not Hyperimmunized, CP | 1.5 b | 7.8bcd |
| 5. Antigens B, C, Co1, Co2, 0.10%, CP | 1.1 c | 9.4bc |
| 6. Antigens B, C, Co1, Co2, 0.20%, CP | 1.4 bc | 4.7cd |
| 7. Antigens B, C, Co1, Co2, 0.40%, CP | 1.3 bc | 6.3bcd |
| 8. ET-50, Antigens B, C, Co1, Co2, 0.10%, CP | 1.5 bc | 14.1ab |
| 9. ET-50, Antigens B, C, Co1, Co2, 0.20%, CP | 1.4 bc | 7.8bcd |
| 10. ET-50, Antigens B, C, Co1, Co2, 0.40%, CP | 1.4 bc | 3.1cd |

TABLE 18

Feed Intake and Weight Gain from Day 0 to Day 28.

| Treatment Group | Feed Intake D 0-28 | Weight Gain D 0-28 |
|---|---|---|
| 1. No Additive, No CP | 7.814a | 0.831a |
| 2. No Additive, CP | 6.494d | 0.584de |
| 3. Bacitracin 50 g/t, CP | 6.708bcd | 0.648bcd |
| 4. Egg Not Hyperimmunized, CP | 6.955bcd | 0.559de |
| 5. Antigens B, C, Co1, Co2, 0.10%, CP | 6.608cd | 0.546e |
| 6. Antigens B, C, Co1, Co2, 0.20%, CP | 6.584cd | 0.609cde |
| 7. Antigens B, C, Co1, Co2, 0.40%, CP | 6.845bcd | 0.637bcde |
| 8. ET-50, Antigens B, C, Co1, Co2, 0.10%, CP | 6.743bcd | 0.642bcde |
| 9. ET-50, Antigens B, C, Co1, Co2, 0.20%, CP | 7.125bc | 0.708b |
| 10. ET-50, Antigens B, C, Co1, Co2, 0.40%, CP | 7.288ab | 0.685bc |

Example 8—Efficacy of 0.025%, 0.050% and 0.100% Doses of Hyperimmune Egg Powder and 0.400% Dose of an IgY Aqueous Concentrate Against Necrotic Enteritis in Broiler Chickens Infected with Subclinical Levels of *C. perfringens*

Experimental Design

The study consisted of 80 cages starting with 8 chicks each. The treatments were replicated in 8 blocks of 10 cages each. The treatment groups are shown below in Table 19 below. For treatment Group 10, an IgY aqueous concentrate was diluted in water and administered through a water feeder. The aqueous concentrate was dispensed aseptically, and the remaining concentrate was stored in its closed container under refrigeration until required for preparation of the next treated water reservoir. The IgY concentrate was diluted at a rate of 0.783 mL of IgY aqueous concentrate/L of feeder water. For example, each water reservoir received 6.26 mL of IgY aqueous concentrate well mixed into 8 L of water prior to administration. This dilution rate is a dosing equivalent to a 0.4% w/w inclusion rate of dried egg powder in solid feed, i.e. chickens in treatment Group 10 administered IgY in the feeder water received the same amount of IgY as chickens fed solid feed at a 0.4% dried egg powder feed inclusion rate. Preparation of the IgY aqueous concentrate is described below.

TABLE 19

Treatment Groups.

| | Coccidial Challenge | *Clostridium perfringens* | Cages/ Trt |
|---|---|---|---|
| 1. Nonmedicated control | Day 14 | No | 8 |
| 2. Nonmedicated control | Day 14 | Day 19, 20, and 21 | 8 |
| 3. Antibiotic control, bacitracin 50 g/t | Day 14 | Day 19, 20, and 21 | 8 |
| 4. Antigens B, C, Co1, Co2 0.025% Feed Inclusion Rate | Day 14 | Day 19, 20, and 21 | 8 |
| 5. Antigens B, C, Co1, Co2 0.050% Feed Inclusion Rate | Day 14 | Day 19, 20, and 21 | 8 |
| 6. Antigens B, C, Co1, Co2 0.1% Feed Inclusion Rate | Day 14 | Day 19, 20, and 21 | 8 |
| 7. ET-50 + Antigens B, C, Co1, Co2 0.025% Feed Inclusion Rate | Day 14 | Day 19, 20, and 21 | 8 |
| 8. ET-50 + Antigens B, C, Co1, Co2 0.05% Feed Inclusion Rate | Day 14 | Day 19, 20, and 21 | 8 |
| 9. ET-50 + Antigens B, C, Co1, Co2 + 0.1% Feed Inclusion Rate | Day 14 | Day 19, 20, and 21 | 8 |
| 10. ET-50 + Antigens B, C, Co1, Co2 + administered via drinking water at a dose equivalent to 0.40% ET-50 + Antigens B, C, Co1, Co2 dried egg powder | Day 14 | Day 19, 20, and 21 | 8 |

Materials and Methods

A. Experimental Ration

An unmedicated chicken starter compounded with feedstuffs commonly used in the United States was formulated. The diet was representative of a local commercial formulation and calculated analyses met or exceeded NRC broiler starter requirements. Experimental treatment feeds were prepared from this basal starter feed. Treatment feeds were mixed to assure a uniform distribution of the test article. The mixer was flushed to prevent cross contamination. The feed was distributed among cages of the same treatment. This ration (in mash form) was fed during the study.

B. Animals

Day of hatch male broiler chicks were obtained from Cobb-Vantress, Cleveland, Ga. The strain was Cobb 500. Breeder flock information was recorded. At the hatchery, the birds were sexed and received routine vaccinations. Only healthy appearing chicks were used in the study. Eight chicks were placed per cage. Disposition of all birds not used for allocation was documented.

C. Housing

Upon arrival, chicks were raised in Petersime battery cages. At placement the birds were fed the treatment feeds. The chicks were housed in an insulated, concrete floored, metal structure. Thermostatically controlled gas furnace/air conditioner maintained uniform temperature.

Procedures

A. Bird Allocation and Cage Randomization

The study began when the birds were placed (day of hatch) (Day 0) at which time they were allocated to the experimental cages. No birds were replaced during the course of the study.

B. Cage Weights

All birds were weighed on Day 0, 14, 21, and 28. Feed was weighed in on Day 0 and remaining feed was weighed on Day 14, 21, and 28.

C. Disease Induction

On Day 14, all birds were orally inoculated with 5,000 oocysts of *Eimeria maxima*. Starting on Day 19, all birds, except Treatment 1 were given a broth culture of *Clostridium perfringens* $-10^8$ cfu/ml. The CP is an isolate from a clinical case of necrotic enteritis. It is both alpha toxin and net B toxin positive. The birds were administered a fresh broth culture once daily for 3 days (on Days 19, 20, and 21).

D. Necrotic Enteritis Intestinal Lesion Scoring

On Day 21, three birds from each cage were selected, sacrificed, weighed, and examined for the degree of presence of Necrotic Enteritis lesions. The scoring was based on a 0 to 3 score, with 0 being normal and 3 being the most severe.

Lesion score 0=Normal
Lesion score 1=Slight mucus covering small intestine
Lesion score 2=Necrotic small intestine mucosa
Lesion score 3=Sloughed and blood small intestine mucosa and contents E. Management 1. The facility was checked thoroughly to assure that all cages had water and that feed was available in every cage. The building temperature's range was maintained at an appropriate temperature for the age of the birds.

2. Even, continuous illumination was provided by fluorescent lamps hung vertically along the wall.

3. Feed and water were given ad libitum.

4. The cages were checked twice daily. Observations included were the availability of feed and water, temperature control, and any unusual conditions. The birds were watched closely for any abnormal reactions.

5. When dead birds were removed from cages, the cage number, date, weight of the bird, sex, and probable cause of death were recorded.

F. Preparation of IgY Aqueous Concentrate from Egg Yolks

Step 1: Three volumes of 0.3% Acetic acid (33 liters) was mixed with 11 liters of pasteurized egg yolks, and the mixture was refrigerated for at least 12 hr, at 2-8° C.

Step 2: The mixture was centrifuged at 17,000×g, to minimize settleable solids in the aqueous concentrate. Centrifugation yielded approximately 36.6 L of supernatant and a 7.4 L pellet.

Step 3: 98% caprylic acid was added to the aqueous supernatant at a ratio of 1.9-2.1% V/V to yield approximately 37.4 L total volume. The solution was mixed for 4 hours at 2-8° C. and then centrifuged at 17,000×g to clarify the aqueous concentrate. Centrifugation yielded approximately 27.4 L of supernatant, and a 10 L pellet.

Step 4: Caprylic acid was decanted from the supernatant and the supernatant was filtered on large size buchner funnels to remove residual solids, if any.

Step 5: Water was removed from the supernatant by filtration to achieve approximately 20% solids.

To recover additional IgY, the pellet formed in Step 3 was mixed with deionized water at a ratio of 1:1 v/v, and the mixture was centrifuged at 17,000×g. The supernatant was then processed as described in Steps 4 and 5 above.

The aqueous IgY concentrate was stored at 4° C. until use.

Results

All of the IgY treatments (treatment Groups 3-10) significantly lowered lesion scores and percent mortality relative to the infected control (treatment group 2) at Day 21. See Table 20. Treatment groups 4 to 8 also exhibited significantly increased weight gain relative to the infected control (treatment group 2) from Days 0 to 28. See Table 21.

TABLE 20

Necrotic Enteritis Lesion Score on Day 21 and Percent Necrotic Enteritis Mortality.

| | Treatment Group | Lesion Score (0-3) | % NE Mortality |
|---|---|---|---|
| 1. | No Additive, No CP | 0.0d | 0.0e |
| 2. | No Additive, CP | 1.9a | 37.5a |
| 3. | Antibiotic control, bacitracin 50 g/t, CP | 1.0bc | 10.9bcde |
| 4. | Antigens B, C, Co1, Co2 0.025% Feed Inclusion Rate, CP | 1.0bc | 21.9b |

TABLE 20-continued

Necrotic Enteritis Lesion Score on Day 21 and Percent Necrotic Enteritis Mortality.

| | Treatment Group | Lesion Score (0-3) | % NE Mortality |
|---|---|---|---|
| 5. | Antigens B, C, Co1, Co2, CP 0.050% Feed Inclusion Rate | 1.0bc | 15.6bcd |
| 6. | Antigens B, C, Co1, Co2 0.1% Feed Inclusion Rate, CP | 0.9c | 7.8cde |
| 7. | ET-50 + Antigens B, C, Co1, Co2 0.025% Feed Inclusion Rate, CP | 1.2bc | 20.3bc |
| 8. | ET-50 + Antigens B, C, Co1, Co2 0.05% Feed Inclusion Rate, CP | 1.3b | 17.2bcd |
| 9. | ET-50 + Antigens B, C, Co1, Co2 + 0.1% Feed Inclusion Rate, CP | 1.0bc | 15.6bcd |
| 10. | ET-50 + Antigens B, C, Co1, Co2 + administered via drinking water at a dose equivalent to 0.40% ET-50 + Antigens B, C, Co1, Co2 dried egg powder, CP | 1.0bc | 7.8de |

TABLE 21

Feed Intake, Feed Conversion and Weight Gain from Day 0 to Day 28.

| | Treatment Group | Feed Intake D 0-28 | Weight Gain D 0-28 |
|---|---|---|---|
| 1. | No Additive, No CP | 9.001a | 0.804a |
| 2. | No Additive, CP | 7.377cd | 0.478d |
| 3. | Antibiotic control, bacitracin 50 g/t, CP | 8.040bc | 0.590bcd |
| 4. | Antigens B, C, Co1, Co2 0.025% Feed Inclusion Rate, CP | 7.664cd | 0.624bc |
| 5. | Antigens B, C, Co1, Co2, CP 0.050% Feed Inclusion Rate | 7.789bcd | 0.608bc |
| 6. | Antigens B, C, Co1, Co2 0.1% Feed Inclusion Rate, CP | 8.609ab | 0.683b |
| 7. | ET-50 + Antigens B, C, Co1, Co2 0.025% Feed Inclusion Rate, CP | 7.120d | 0.638bc |
| 8. | ET-50 + Antigens B, C, Co1, Co2 0.05% Feed Inclusion Rate, CP | 7.608cd | 0.676b |
| 9. | ET-50 + Antigens B, C, Co1, Co2 + 0.1% Feed Inclusion Rate, CP | 7.582cd | 0.582bcd |
| 10. | ET-50 + Antigens B, C, Co1, Co2 + administered via drinking water at a dose equivalent to 0.40% ET-50 + Antigens B, C, Co1, Co2 dried egg powder, CP | 8.158abc | 0.588cd |

Example 9—Detection of IgY Antibodies in Hyperimmunized Eggs

Hens were hyperimmunized for detection of polyclonal antibodies to each of the four antigens B, C, Co1 and Co2 in eggs collected from the hyperimmunized animals. One group of hens was hyperimmunized with the four antigens B, C, Co1 and Co2. A second group of hens was hyperimmunized with the four antigens B, C, Co1 and Co2, and the ET-50 antigen described above in Example 1. Specific Pathogen Free (SPF) hens were used as a control to determine the increase in antibodies to the B, C, Co1 and Co2 antigens resulting from hyperimmunization. The treatment groups of hens are summarized in Table 22 below.

TABLE 22

Hen treatment groups for detection of IgY antibodies to B, C, Co1 or Co2 antigens by ELISA in egg samples.

| Treatment Group | Antigens for Hyperimmunization |
|---|---|
| 1 | B, C, Co1 and Co2 |
| 2 | B, C, Co1, Co2 and ET-50 |
| 3 | None, Specific Pathogen Free (SPF) hens |

The final concentration of each of the four antigens B, C, Co1 and Co2 in the vaccine was 100 ag/ml. The volume of the 26 antigen pool that was used to formulate the NE+PL-100 vaccine was replaced with 10 mM PBS, pH 7.4 in the NE Only vaccine. The vaccines consisted of equal parts of the antigen mixture and Freund's adjuvant. A Freund's Complete adjuvant was used for the priming dose (administered as 2×0.5 ml dosed into each breast), and a Freund's incomplete adjuvant was used as a boost dose (administered as 1×0.5 ml dose into one breast). The boost doses were given 2 weeks following priming and again at 5 weeks following priming. Eggs were collected starting 10 days following the priming dose, and continued over a period of 10 days which yielded about 360 eggs. Eggs were pooled on three different days within the 10 day period, and each pool was analyzed separately by ELISA. The eggs were broken, homogenized and frozen. A portion of the eggs from each pool was spray dried, while another portion from each pool was maintained as liquid whole egg.

A sample from each of the liquid eggs and the corresponding spray dried product was analyzed by ELISA for detection of polyclonal antibodies to antigens B, C, Co1 and Co2. Each ELISA assay also included control eggs from the SPF hens (treatment group 3). In addition, a sample with no egg was used as a negative control (nc) for the ELISA assay, and a sample containing isolated IgY antibodies from egg known to contain IgY against the specific antigen of interest was used as a positive control (pAb). The treatment groups for the ELISA assay are shown in Table 23 below.

TABLE 23

Treatment groups for ELISA detection of IgY antibodies to B, C, Co1 or Co2 in egg samples.

| Treatment Group | Name | Description |
|---|---|---|
| 1 | NE Only | Egg sample from hens hyper-immunized with B, C, Co1 and Co2 |
| 2 | NE + PL-100 | Egg sample from hens hyper-immunized with B, C, Co1, Co2, and PL-100 |
| 3 | Specific Pathogen Free (SPF) control | Egg sample from Specific Pathogen Free (SPF) hens |
| 4 | ELISA negative control (nc) | Sample without egg |
| 5 | ELISA positive control (pAb) | Purified IgY antibodies containing polyclonal antibodies to B, C, Co1 and Co2 antigens |

ELISA Assay 96 well flat bottom plates were coated with *E. coli* expressed recombinant protein B, C, Co1 or Co2 antigen (100 ul of 10 ug/ml protein), 2 plates for each antigen. Samples were serially diluted with 0.1% BSA/PBS ELISA assay buffer. Plates were shaken for 30 sec on rocker gently and then left at 4° C. (or −20° C.) overnight. Samples were washed 2 times with 0.05% Tween-20+1×PBS. The liquid was flicked off and the plates were patted dry on paper towels. 100 ul 1% BSA/PBS was added to each well for blocking. The plates were incubated for 60 min with gentle shaking at room temperature. The liquid was flicked off and plates were patted dry on paper towels. 100 ul of serially diluted Egg yolk in 0.1% BSA/PBS was added. The starting concentration of total egg yolk protein was 1 mg/ml (measured at 280 nm with nanodrop). The dilutions tested were 1000, 500, 250, 125, 62.5, 31.25, 15.63, 7.813, 3.906, 1.953, 0.977 and 0.488 ag total egg yolk protein/ml.

The plates were incubated for 1 hr with gentle shaking at room temperature. Plates were washed 6 times, liquid was flicked off and plate was dried in paper towels. 100 ul of detecting Ab (Anti-chicken IgY-peroxidase 1:500 in 0.1% BSA/PBS) was added to each well and samples were mixed gently and incubated for 30 min at R.T. with shaking. Plate was washed 6 times, liquid was removed, and plate was dried. 100 ul of freshly prepared Peroxidase substrate solution well dissolved in developing buffer (10 ml of 0.05 M phosphate citrate buffer+1 TMB tablet, vortexing until completely dissolved, and then added 50 ul of hydrogen peroxidase (30%)—just before adding to plate) was added to each well. Color development was confirmed by mixing 100 ul of peroxidase substrate with 100 ul peroxidase rabbit antibody. Samples were incubated 5-15 minutes at room temperature to allow color development. 50 ul of 2N $H_2SO_4$ was added to stop reaction as color developed, inducing a color change from blue to yellow. Absorbance was read at 450 nm.

Results

All of the egg samples from hens hyperimmunized with antigens B, C, Co1 and Co2 (treatment group 1) or antigens B, C, Co1, Co2 and ET-50 (treatment group 2) contained more IgY antibodies for each of the antigens B, C, Co1 and Co2 than egg samples from hens that were not hyperimmunized (i.e. SPF hens, treatment group 3). See FIGS. 28 and 29. The increased levels of IgY antibodies to B, C, Co1 or Co2 in the hyperimmunized eggs was observed in both liquid whole eggs (FIG. 28) and spray-dried egg powder (FIG. 29). For example, in spray-dried egg powder, hens hyperimmunized with antigens B, C, Co1 and Co2 (treatment group 1) exhibited at least a three-fold increase in IgY antibodies to antigen Co1, at least a 2-fold increase in IgY antibodies to antigen B, at least a 5-fold increase in IgY antibodies to antigen Co2, and at least a 2-fold increase in IgY antibodies to antigen C at the highest dilution rate relative to spray-dried egg powder from control hens that were not hyperimmunized (SPF hens). See FIG. 29. Thus hyperimmunization resulted in large increases in IgY antibodies to antigens B, C, Co1 and Co2 relative to hens that were not hyperimmunized.

The invention claimed is:

1. A hyperimmunized egg produced by an animal that has been hyperimmunized with at least one isolated antigen selected from the group consisting of *Clostridium perfringens* α-toxin, *Clostridium perfringens* elongation factor Tu (EF-Tu), *Clostridium perfringens* necrotic enteritis B-like (NetB) toxin, *Clostridium perfringens* Pyruvate: Ferredoxin oxidoreductase (PFO), and *Eimeria tenella* elongation factor 1-alpha, wherein the hyperimmunized egg comprises an increased level of an antibody to said at least one antigen of at least 500% relative to an egg from an animal that has not been hyperimmunized.

2. The hyperimmunized egg of claim 1, wherein the level of antibodies to *Clostridium perfringens* elongation factor Tu (EF-Tu) and *Clostridium perfringens* necrotic enteritis B-like (NetB) toxin in the hyperimmunized egg product is increased relative to the egg from the animal that has not been hyperimmunized.

3. The hyperimmunized egg of claim 1, wherein the hyperimmunized animal has also been hyperimmunized with *Eimeria tenella* 3-1E profilin.

4. The hyperimmunized egg of claim 3, wherein the level of antibodies to *Eimeria tenella* 3-1E profilin in the hyperimmunized egg is increased relative to the egg from the animal that has not been hyperimmunized.

5. The hyperimmunized egg of claim 1, wherein the hyperimmunized animal has also been hyperimmunized with at least one antigenic bacterium selected from the group consisting of *Escherichia coli*; *Escherichia coli* (Aerobacter); *Klebsiella pneumoniae*; *Pseudomonas aeruginosa*; *Salmonella typhimurium*; *Salmonella dysenteriae*; *Salmonella enteriditis*; *Salmonella epidermis*; *Salmonella simulans*; *Streptococcus pyogenes*, type 1; *Streptococcus pyogenes*, type 3; *Streptococcus pyogenes*, type 5; *Streptococcus pyogenes*, type 8; *Streptococcus pyogenes*, type 12; *Streptococcus pyogenes*, type 14; *Streptococcus pyogenes*, type 18; *Streptococcus pyogenes*, type 22; *Pseudomonas vulgaris*; *Streptococcus agalactiae*; *Streptococcus mitis*; *Streptococcus mutans*; *Streptococcus salavarius*; *Streptococcus sanguis*; *Streptococcus pneumoniae*; *Propionibacterium acnes*; and *Haemophilis influenzae*.

6. A hyperimmunized egg product obtained from the hyperimmunized egg of claim 1.

7. An animal feed comprising the hyperimmunized egg product of claim 6.

8. The hyperimmunized egg product of claim 6, wherein the hyperimmunized egg product is an egg powder.

9. The hyperimmunized egg product of claim 6, wherein the hyperimmunized egg product is an aqueous solution.

* * * * *

SEQUENCE LISTING

<160> NUMBER OF SEQ ID NOS: 12

<210> SEQ ID NO 1

```
<211> LENGTH: 398
<212> TYPE: PRT
<213> ORGANISM: Clostridium perfringens

<400> SEQUENCE: 1

Met Lys Arg Lys Ile Cys Lys Ala Leu Ile Cys Ala Ala Leu Ala Thr
1               5                   10                  15

Ser Leu Trp Ala Gly Ala Ser Thr Lys Val Tyr Ala Trp Asp Gly Lys
            20                  25                  30

Ile Asp Gly Thr Gly Thr His Ala Met Ile Val Thr Gln Gly Val Ser
        35                  40                  45

Ile Leu Glu Asn Asp Leu Ser Lys Asn Glu Pro Glu Ser Val Arg Lys
50                  55                  60

Asn Leu Glu Ile Leu Lys Glu Asn Met His Glu Leu Gln Leu Gly Ser
65                  70                  75                  80

Thr Tyr Pro Asp Tyr Asp Lys Asn Ala Tyr Asp Leu Tyr Gln Asp His
                85                  90                  95

Phe Trp Asp Pro Asp Thr Asp Asn Asn Phe Ser Lys Asp Asn Ser Trp
            100                 105                 110

Tyr Leu Ala Tyr Ser Ile Pro Asp Thr Gly Glu Ser Gln Ile Arg Lys
        115                 120                 125

Phe Ser Ala Leu Ala Arg Tyr Glu Trp Gln Arg Gly Asn Tyr Lys Gln
130                 135                 140

Ala Thr Phe Tyr Leu Gly Glu Ala Met His Tyr Phe Gly Asp Ile Asp
145                 150                 155                 160

Thr Pro Tyr His Pro Ala Asn Val Thr Ala Val Asp Ser Ala Gly His
                165                 170                 175

Val Lys Phe Glu Thr Phe Ala Glu Glu Arg Lys Glu Gln Tyr Lys Ile
            180                 185                 190

Asn Thr Val Gly Cys Lys Thr Asn Glu Asp Phe Tyr Ala Asp Ile Leu
        195                 200                 205

Lys Asn Lys Asp Phe Asn Ala Trp Ser Lys Glu Tyr Ala Arg Gly Phe
210                 215                 220

Ala Lys Thr Gly Lys Ser Ile Tyr Tyr Ser His Ala Ser Met Ser His
225                 230                 235                 240

Ser Trp Asp Asp Trp Asp Tyr Ala Ala Lys Val Thr Leu Ala Asn Ser
                245                 250                 255

Gln Lys Gly Thr Ala Gly Tyr Ile Tyr Arg Phe Leu His Asp Val Ser
            260                 265                 270

Glu Gly Asn Asp Pro Ser Val Gly Lys Asn Val Lys Glu Leu Val Ala
        275                 280                 285

Tyr Ile Ser Thr Ser Gly Glu Lys Asp Ala Gly Thr Asp Asp Tyr Met
290                 295                 300

Tyr Phe Gly Ile Lys Thr Lys Asp Gly Lys Thr Gln Glu Trp Glu Met
305                 310                 315                 320

Asp Asn Pro Gly Asn Asp Phe Met Thr Gly Ser Lys Asp Thr Tyr Thr
                325                 330                 335

Phe Lys Leu Lys Asp Glu Asn Leu Lys Ile Asp Asp Ile Gln Asn Met
            340                 345                 350

Trp Ile Arg Lys Arg Lys Tyr Thr Ala Phe Pro Asp Ala Tyr Lys Pro
        355                 360                 365

Glu Asn Ile Lys Val Ile Ala Asn Gly Lys Val Val Asp Lys Asp
370                 375                 380

Ile Asn Glu Trp Ile Ser Gly Asn Ser Thr Tyr Asn Ile Lys
```

<210> SEQ ID NO 2
<211> LENGTH: 1197
<212> TYPE: DNA
<213> ORGANISM: Clostridium perfringens

<400> SEQUENCE: 2

| | | | | | |
|---|---|---|---|---|---|
| atgaaaagaa | agatttgtaa | ggcacttatt | tgtgctgcgc | tagcaactag | cctatgggct | 60 |
| ggggcatcaa | ctaaagtcta | cgcttgggat | ggaaagattg | atggaacagg | aactcatgct | 120 |
| atgattgtaa | ctcaagggt | ttcaatctta | gaaaatgatc | tgtccaaaaa | tgaaccagaa | 180 |
| agtgtaagaa | aaaacttaga | gattttaaaa | gagaacatgc | atgagcttca | attaggttct | 240 |
| acttatccag | attatgataa | gaatgcatat | gatctatatc | aagatcactt | ctgggatcct | 300 |
| gatacagata | taatttctc | aaaggataat | agttggtatt | tagcttattc | tatacctgac | 360 |
| acagggaat | cacaaataag | aaaattttca | gcattagcta | gatatgaatg | gcaaagagga | 420 |
| aactataaac | aagctacatt | ctatcttgga | gaggctatgc | actattttgg | agatatagat | 480 |
| actccatatc | atcctgctaa | tgttactgcc | gttgatagcg | caggacatgt | taagtttgag | 540 |
| acttttgcag | aggaaagaaa | agaacagtat | aaaataaaca | cagtaggttg | caaaactaat | 600 |
| gaggatttt | atgctgatat | cttaaaaaac | aaagatttta | atgcatggtc | aaaagaatat | 660 |
| gcaagaggtt | ttgctaaaac | aggaaaatca | atatactata | gtcatgctag | catgagtcat | 720 |
| agttgggatg | attgggatta | tgcagcaaag | gtaactctag | ctaactctca | aaaaggaaca | 780 |
| gcgggatata | tttatagatt | cttacacgat | gtatcagagg | gtaatgatcc | atcagttgga | 840 |
| aagaatgtaa | agaactagt | agcttacata | tcaactagtg | gtgaaaaaga | tgctggaaca | 900 |
| gatgactaca | tgtattttgg | aatcaaaaca | aaggatggaa | aaactcaaga | atgggaaatg | 960 |
| gacaacccag | gaaatgattt | tatgactgga | agtaaagaca | cttatacttt | caaattaaaa | 1020 |
| gatgaaaatc | taaaaattga | tgatatacaa | aatatgtgga | ttagaaaaag | aaaatataca | 1080 |
| gcattcccag | atgcttataa | gccagaaaac | ataaaggtaa | tagcaaatgg | aaaagttgta | 1140 |
| gtagacaaag | atataaatga | gtggatttca | ggaaattcaa | cttataatat | aaaataa | 1197 |

<210> SEQ ID NO 3
<211> LENGTH: 397
<212> TYPE: PRT
<213> ORGANISM: Clostridium perfringens

<400> SEQUENCE: 3

Met Ser Lys Ala Lys Phe Glu Arg Ser Lys Pro His Val Asn Ile Gly
1               5                   10                  15

Thr Ile Gly His Val Asp His Gly Lys Thr Thr Leu Thr Ala Ala Ile
            20                  25                  30

Thr Thr Val Leu Ala Gln Ala Gly Gly Ala Glu Ala Phe Lys Tyr Asp
        35                  40                  45

Glu Ile Asp Lys Ala Pro Glu Glu Lys Glu Arg Gly Ile Thr Ile Asn
    50                  55                  60

Thr Ala His Val Glu Tyr Glu Thr Ala Asn Arg His Tyr Ala His Val
65                  70                  75                  80

Asp Cys Pro Gly His Ala Asp Tyr Val Lys Asn Met Ile Thr Gly Ala
                85                  90                  95

Ala Gln Met Asp Gly Ala Ile Leu Val Cys Ser Ala Ala Asp Gly Pro
            100                 105                 110

-continued

```
Met Pro Gln Thr Arg Glu His Ile Leu Leu Ser Ser Arg Val Gly Val
        115                 120                 125

Asp His Ile Val Val Phe Leu Asn Lys Ala Asp Met Val Asp Asp Glu
    130                 135                 140

Glu Leu Leu Glu Leu Val Glu Met Glu Val Arg Glu Leu Leu Ser Glu
145                 150                 155                 160

Tyr Asn Phe Pro Gly Asp Asp Ile Pro Val Ile Lys Gly Ser Ala Leu
                165                 170                 175

Val Ala Leu Glu Asn Pro Thr Asp Glu Ala Ala Thr Ala Cys Ile Arg
            180                 185                 190

Glu Ser Met Asp Ala Val Asp Ser Tyr Ile Pro Thr Pro Glu Arg Ala
        195                 200                 205

Thr Asp Lys Pro Phe Leu Met Pro Val Glu Asp Val Phe Thr Ile Thr
    210                 215                 220

Gly Arg Gly Thr Val Ala Thr Gly Arg Val Glu Arg Gly Val Leu His
225                 230                 235                 240

Val Gly Asp Glu Val Glu Val Ile Gly Leu Thr Glu Glu Arg Arg Lys
                245                 250                 255

Thr Val Val Thr Gly Ile Glu Met Phe Arg Lys Leu Leu Asp Glu Ala
            260                 265                 270

Gln Ala Gly Asp Asn Ile Gly Ala Leu Leu Arg Gly Ile Gln Arg Thr
        275                 280                 285

Asp Ile Glu Arg Gly Gln Val Leu Ala Gln Val Gly Thr Ile Asn Pro
    290                 295                 300

His Lys Lys Phe Val Gly Gln Val Tyr Val Leu Lys Lys Glu Glu Gly
305                 310                 315                 320

Gly Arg His Thr Pro Phe Phe Asp Gly Tyr Arg Pro Gln Phe Tyr Phe
                325                 330                 335

Arg Thr Thr Asp Val Thr Gly Ser Ile Lys Leu Pro Glu Gly Met Glu
            340                 345                 350

Met Val Met Pro Gly Asp His Ile Asp Met Glu Val Glu Leu Ile Thr
        355                 360                 365

Glu Ile Ala Met Asp Glu Gly Leu Arg Phe Ala Ile Arg Glu Gly Gly
    370                 375                 380

Arg Thr Val Gly Ser Gly Val Val Thr Ser Ile Ile Glu
385                 390                 395
```

<210> SEQ ID NO 4
<211> LENGTH: 1194
<212> TYPE: DNA
<213> ORGANISM: Clostridium perfringens

<400> SEQUENCE: 4

```
ctactcgatt attgaagtaa caactcctga acctacagtt cttccacctt ctctgatagc     60
gaatcttaat ccttcgtcca tagcgatttc tgtgattaat tcaacttcca tgtcgatgtg    120
gtctccaggc ataaccattt ccattccttc tggtaatttg attgatcctg taacgtctgt    180
tgttctgaag tagaattgtg gtctgtatcc atcgaagaat ggagtatgtc ttccaccttc    240 ttcttttta agtacgtata cttgacctac gaattttttg tgtgggttga ttgttccaac    300
ttgagctaaa acttgacctc tttcgatatc agttctttgg atacctctta ataatgctcc    360
gatgttatct ccagcttgtg cttcatctaa taactttctg aacatttcga ttcctgttac    420
aacagttttt cttctttctt cagttaatcc gattacttct acttcgtctc ctacatgtag    480
aactcctctt tcaactcttc ctgttgcaac tgttcctcta ccagtgattg tgaatacgtc    540
```

-continued

```
ctctactggc attaagaatg gcttatctgt tgctctttct ggtgttggga tgtagctatc    600
tacagcatcc attgactctc tgatacaagc tgttgcagct tcgtcagttg ggttttctaa    660
tgctactaaa gctgatccct tgattactgg aatatcgtct cctgggaagt tgtactcgct    720
taataactct ctaacttcca tttcaactaa ttctaataat tcttcgtcgt caaccatatc    780
tgctttgttt aagaatacta cgatgtggtc aactccaact cttgatgata ataagatgtg    840
ctctcttgtt tgaggcattg gaccatcagc tgctgaacaa actaatatag ctccatccat    900
ttgagctgct ccagtgatca tgtttttaac gtagtcagca tgtcctggac agtcaacgtg    960
agcgtagtgt ctgttagctg tttcgtactc aacgtgtgct gtgttgattg tgattcctct   1020
ttctttttct tctggagctt tatctatttc atcatatttg aatgcttctg ctccaccagc   1080
ttgtgctaaa actgttgtta tagctgctgt taaagttgtt ttaccgtggt ctacgtgacc   1140
gattgttcca atgttaacgt gtggtttgct cctttcaaat tttgcttttg acat         1194
```

<210> SEQ ID NO 5
<211> LENGTH: 292
<212> TYPE: PRT
<213> ORGANISM: Clostridium perfringens

<400> SEQUENCE: 5

```
Ser Glu Leu Asn Asp Ile Asn Lys Ile Glu Leu Lys Asn Leu Ser Gly
1               5                   10                  15

Glu Ile Ile Lys Glu Asn Gly Lys Glu Ala Ile Lys Tyr Thr Ser Ser
            20                  25                  30

Asp Thr Ala Ser His Lys Gly Trp Lys Ala Thr Leu Ser Gly Thr Phe
        35                  40                  45

Ile Glu Asp Pro His Ser Asp Lys Lys Thr Ala Leu Leu Asn Leu Glu
    50                  55                  60

Gly Phe Ile Pro Ser Asp Lys Gln Ile Phe Gly Ser Lys Tyr Tyr Gly
65                  70                  75                  80

Lys Met Lys Trp Pro Glu Thr Tyr Arg Ile Asn Val Lys Ser Ala Asp
                85                  90                  95

Val Asn Asn Asn Ile Lys Ile Ala Asn Ser Ile Pro Lys Asn Thr Ile
            100                 105                 110

Asp Lys Lys Asp Val Ser Asn Ser Ile Gly Tyr Ser Ile Gly Gly Asn
        115                 120                 125

Ile Ser Val Glu Gly Lys Thr Ala Gly Thr Gly Ile Asn Ala Ser Tyr
    130                 135                 140

Asn Val Gln Asn Thr Ile Ser Tyr Glu Gln Pro Asp Phe Arg Thr Ile
145                 150                 155                 160

Gln Arg Lys Asp Asp Ala Asn Leu Ala Ser Trp Asp Ile Lys Phe Val
                165                 170                 175

Glu Thr Lys Asp Gly Tyr Asn Ile Asp Ser Tyr His Ala Ile Tyr Gly
            180                 185                 190

Asn Gln Leu Phe Met Lys Ser Arg Leu Tyr Asn Asn Gly Asp Lys Asn
        195                 200                 205

Phe Thr Asp Asp Arg Asp Leu Ser Thr Leu Ile Ser Gly Gly Phe Ser
    210                 215                 220

Pro Asn Met Ala Leu Ala Leu Thr Ala Pro Lys Asn Ala Lys Glu Ser
225                 230                 235                 240

Val Ile Ile Val Glu Tyr Gln Arg Phe Asp Asn Asp Tyr Ile Leu Asn
                245                 250                 255
```

Trp Glu Thr Thr Gln Trp Arg Gly Thr Asn Lys Leu Ser Thr Ser
            260                 265                 270

Glu Tyr Asn Glu Phe Met Phe Lys Ile Asn Trp Gln Asp His Lys Ile
        275                 280                 285

Glu Tyr Tyr Leu
    290

<210> SEQ ID NO 6
<211> LENGTH: 879
<212> TYPE: DNA
<213> ORGANISM: Clostridium perfringens

<400> SEQUENCE: 6

```
agtgaattaa atgacataaa caaaattgag ttgaaaaatc taagtggaga ataataaaa      60
gaaaatggaa aggaagctat taaatatact tctagtgata ccgcttcaca taaaggttgg   120
aaggcaactt taagtggaac atttattgaa gatcctcatt ctgataagaa aactgcttta   180
ttaaatttag aaggatttat accttctgat aaacagattt ttggttctaa atattacgga   240
aaaatgaaat ggcctgaaac ttatagaatt aatgtaaaaa gtgctgatgt aaataataat   300
ataaaaatag caaattctat tcctaaaaat actatagata aaaagatgt atctaattca    360
attggttatt ctataggcgg taatatatct gttgaaggaa aaactgctgg tactggaata   420
aatgcttcat ataatgtcca aaatactata agctatgaac aacctgattt tagaacaatt   480
caaagaaaag atgatgcaaa tttagcatca tgggatataa aatttgttga gactaaggac   540
ggttataata tagattctta tcatgctatt tatggaaatc aattattcat gaaatcaaga   600
ttgtataata atggtgataa aaatttcaca gatgatagag atttatcaac attaatttct   660
ggtggatttt cacccaatat ggctttagca ttaacagcac taaaaatgc taagaatct    720
gtaataatag ttgaatatca aagatttgat aatgactata ttttaaattg ggaaactact   780
caatggcgag gaacaaacaa actttcgtca acaagtgaat ataacgaatt tatgtttaaa   840
ataaattggc aagatcataa aatagaatat tatctgtaa                          879
```

<210> SEQ ID NO 7
<211> LENGTH: 1171
<212> TYPE: PRT
<213> ORGANISM: Clostridium perfringens

<400> SEQUENCE: 7

Met Ala Met Arg Lys Met Lys Thr Met Asp Gly Asn Thr Ala Ala Ala
1               5                   10                  15

Tyr Ile Ser Tyr Ala Phe Thr Asp Val Ala Ala Ile Phe Pro Ile Thr
            20                  25                  30

Pro Ser Ser Pro Met Ala Glu Trp Val Asp Glu Asn Ser Ala Arg Gly
        35                  40                  45

Leu Lys Asn Ile Phe Gly Gln Pro Val Lys Val Met Glu Met Gln Ser
    50                  55                  60

Glu Ala Gly Ala Ala Gly Ala Val His Gly Ser Leu Gln Ala Gly Ala
65                  70                  75                  80

Leu Thr Thr Thr Tyr Thr Ala Ser Gln Gly Leu Leu Leu Met Ile Pro
                85                  90                  95

Asn Met Tyr Lys Ile Ala Gly Glu Leu Leu Pro Ser Val Phe His Val
            100                 105                 110

Ser Ala Arg Ala Leu Ala Thr Ser Ala Leu Asn Ile Phe Gly Asp His
        115                 120                 125

-continued

```
Gln Asp Val Met Ala Ala Arg Gln Thr Gly Phe Ala Met Leu Ala Glu
130                 135                 140

Gly Ser Val Gln Glu Val Met Asp Leu Ser Ala Val Ala His Leu Ala
145                 150                 155                 160

Ala Leu Lys Ala Arg Ile Pro Phe Val Asn Phe Phe Asp Gly Phe Arg
                165                 170                 175

Thr Ser His Glu Ile Gln Lys Val Glu Leu Leu Gln Tyr Asp Glu Leu
            180                 185                 190

Lys Glu Leu Val Asp Met Glu Ala Val Glu Glu Phe Arg Arg Arg Ala
        195                 200                 205

Leu Asn Pro Asn Lys Pro Val Thr Arg Gly Thr Ala Gln Asn Pro Asp
210                 215                 220

Ile Tyr Phe Gln Glu Arg Glu Ala Val Asn Lys Phe Tyr Asp Ala Val
225                 230                 235                 240

Pro Glu Ile Val Glu Ser Tyr Met Lys Glu Ile Thr Lys Leu Thr Gly
                245                 250                 255

Arg Glu Tyr Asn Cys Phe Asp Tyr Tyr Gly Ala Ala Asp Ala Glu Arg
            260                 265                 270

Val Ile Val Ala Met Gly Ser Val Thr Asp Leu Ile Glu Glu Thr Val
        275                 280                 285

Asp Tyr Leu Asn Ala Lys Gly Glu Lys Val Gly Leu Ile Lys Val Arg
290                 295                 300

Leu Phe Arg Pro Phe Ser Asn Glu Arg Leu Ile Lys Ala Met Pro Lys
305                 310                 315                 320

Thr Val Lys Lys Val Ala Val Leu Asp Arg Thr Lys Glu Pro Gly Ala
                325                 330                 335

Ala Gly Glu Pro Leu Tyr Leu Glu Val Lys Asn Ala Phe Tyr Gly Leu
            340                 345                 350

Glu Asn Ala Pro Val Ile Val Gly Gly Arg Phe Gly Leu Gly Ser Lys
        355                 360                 365

Asp Thr Val Pro Ala Asp Ile Val Ala Val Tyr Glu Asn Leu Asn Lys
370                 375                 380

Glu Asp Ala Lys Asn Gly Phe Thr Leu Ser Ile Val Asp Asp Val Thr
385                 390                 395                 400

Asn Thr Ser Leu Glu Pro Val Gly Asp Ile Asp Thr Thr Pro Glu Gly
                405                 410                 415

Thr Lys Ala Cys Lys Phe Trp Gly Leu Gly Ser Asp Gly Thr Val Gly
            420                 425                 430

Ala Asn Lys Ser Ala Ile Lys Ile Ile Gly Asp His Thr Asp Met Tyr
        435                 440                 445

Ala Gln Gly Tyr Phe Ala Tyr Asp Ser Lys Lys Ser Gly Gly Val Thr
450                 455                 460

Ile Ser His Leu Arg Phe Gly Lys Gln Pro Ile Lys Ser Pro Tyr Leu
465                 470                 475                 480

Ile Asn Lys Ala Asp Phe Val Ala Cys His Asn Gln Ser Tyr Val Asn
                485                 490                 495

Lys Tyr Phe Val Leu Asp Gly Leu Lys Lys Asn Gly Thr Phe Leu Leu
            500                 505                 510

Asn Thr Ile Trp Thr Pro Glu Val Ala Glu His Leu Pro Ala Ser
        515                 520                 525

Tyr Lys Arg Phe Leu Ala Glu Asn Asn Ile Lys Phe Tyr Thr Leu Asn
530                 535                 540

Ala Val Lys Ile Ala Gln Glu Val Gly Leu Gly Gly Arg Ile Asn Met
```

```
              545              550              555              560
Ile Met Gln Ser Ala Phe Phe Lys Leu Ala Asn Ile Ile Pro Val Glu
                565              570              575

Asp Ala Val Lys Tyr Leu Lys Asp Ala Val Val Thr Ser Tyr Gly Lys
                580              585              590

Lys Gly Glu Lys Val Val Asn Met Asn His Ala Ala Ile Asp Lys Gly
                595              600              605

Ile Asp Ala Ile Val Glu Ile Thr Val Pro Ala Glu Trp Ala Asn Ala
                610              615              620

Lys Asp Glu Val Val Glu Ala Lys Glu Val Pro Ala Phe Ile Lys Asn
625              630              635              640

Ile Val Glu Pro Met Asn Arg Leu Glu Gly Asp Lys Leu Pro Val Ser
                645              650              655

Ala Phe Asn Gly Met Glu Asp Gly Thr Phe Glu Pro Gly Thr Ala Ala
                660              665              670

Tyr Glu Lys Arg Gly Ile Gly Ile Asn Ile Pro Glu Trp Ile Ala Asp
                675              680              685

Asn Cys Ile Gln Cys Asn Gln Cys Ala Tyr Val Cys Pro His Ala Thr
                690              695              700

Ile Arg Pro Phe Leu Leu Thr Glu Glu Ala Lys Asn Ala Pro Ala
705              710              715              720

Ser Thr Lys Leu Val Ala Ala Lys Ala Leu Lys Thr Glu Pro Met
                725              730              735

Gln Phe Thr Met Ala Val Ser Thr Leu Asp Cys Thr Gly Cys Gly Asn
                740              745              750

Cys Ala Gln Val Cys Pro Ala Lys Glu Lys Ala Leu Val Met Lys Pro
                755              760              765

Gln His Thr Gln Glu Asp Gln Ile Glu Ala Trp Asp Tyr Cys Val Asn
                770              775              780

Asp Val Pro Lys Lys Asn Pro Met Asn Lys Asn Thr Val Lys Gly
785              790              795              800

Ser Gln Phe Glu Gln Pro Leu Phe Glu Phe Ser Gly Ala Cys Ala Gly
                805              810              815

Cys Gly Glu Thr Pro Tyr Ala Lys Leu Ile Thr Gln Leu Phe Gly Asp
                820              825              830

Arg Met Met Ile Ala Asn Ala Thr Gly Cys Ser Ser Ile Trp Gly Gly
                835              840              845

Ser Ala Pro Ser Thr Pro Tyr Thr Thr Asn His Asn Gly His Gly Pro
850              855              860

Ala Trp Ala Asn Ser Leu Phe Glu Asp Asn Ala Glu Phe Gly Leu Gly
865              870              875              880

Met Phe Leu Gly Val Lys Ala Ile Arg Glu Arg Leu Val Asp Leu Ala
                885              890              895

Gly Lys Ala Ile Glu Ala Gly Val Lys Pro Glu Ala Lys Glu Ala Leu
                900              905              910

Glu Ala Trp Ile Ala Glu Val Asp Asn Gly Glu Gly Thr Arg Asp Arg
                915              920              925

Ala Asp Ala Val Val Ala Ala Leu Gln Gly Glu Thr Asn Glu Phe Ala
                930              935              940

Lys Glu Ile Leu Lys Asp Gln Asp Tyr Leu Ala Lys Arg Ser Gln Trp
945              950              955              960

Ile Phe Gly Gly Asp Gly Trp Ala Tyr Asp Ile Gly Tyr Gly Gly Val
                965              970              975
```

Asp His Val Leu Ala Ser Gly Glu Asp Val Asn Ile Leu Val Met Asp
            980             985                 990

Thr Glu Ile Tyr Ser Asn Thr Gly Gly Gln Ala Ser Lys Ser Thr Pro
        995                 1000                1005

Thr Ala Ala Ile Ala Lys Phe Ala Ala Ala Gly Lys Arg Thr Lys
    1010                1015                1020

Lys Lys Asp Leu Gly Met Met Ala Met Ser Tyr Gly Tyr Val Tyr
    1025                1030                1035

Val Ala Gln Ile Ala Met Gly Ala Asp Lys Asn Gln Thr Leu Lys
    1040                1045                1050

Ala Ile Ala Glu Ala Glu Ala Tyr Lys Gly Pro Ser Leu Ile Ile
    1055                1060                1065

Ala Tyr Ala Pro Cys Ile Ser His Gly Leu Lys Ala Gly Met Gly
    1070                1075                1080

Asn Ser Gln Leu Glu Glu Lys Arg Ala Val Glu Cys Gly Tyr Trp
    1085                1090                1095

Ala Met Tyr Arg Phe Asn Pro Met Leu Lys Glu Thr Gly Lys Asn
    1100                1105                1110

Pro Phe Ser Leu Asp Ser Lys Glu Pro Thr Gly Asp Phe Arg Glu
    1115                1120                1125

Phe Ile Met Gly Glu Val Arg Tyr Ala Ala Leu Ala Lys Ala Phe
    1130                1135                1140

Pro Glu Ala Ala Glu Ala Leu Phe Glu Lys Thr Glu Arg Asp Ala
    1145                1150                1155

Lys Glu Arg Leu Glu Asn Tyr Lys Lys Leu Ala Ala Asn
    1160                1165                1170

<210> SEQ ID NO 8
<211> LENGTH: 3516
<212> TYPE: DNA
<213> ORGANISM: Clostridium perfringens

<400> SEQUENCE: 8

```
ctagtttgca gcaagttttt tgtagttttc taatctttct ttagcatctc tttcagtctt     60
ttcgaataaa gcttcagcag cttctgggaa tgcttttgct aatgcagcgt atctaacttc    120
tcccattatg aattctctga atcaccagt tggttcttta gagtctaatg agaatggatt     180
cttaccagtt tcttttaaca ttgggttgaa tctgtacata gcccagtatc cgcattcaac    240
agctctcttc tcttctaatt gagagttacc cataccagct tttaatccgt ggctgataca    300
tggagcgtaa gctattatta tgatggtcc tttgtatgct tcagcttcag ctatagcttt    360
aagagtttgg ttcttatctg cacccatagc tatttgagca acatatacat aaccatagct    420
catagccatc attcctaaat ctttcttctt agttctctta cctgcagcag cgaatttagc    480
gatagcagca gttggagttg atttagaagc ctgaccacca gtatttgagt agatttctgt    540
atccataaca agtatgttta catcttctcc actagctaaa cgtggtcaa ctccaccgta     600
accgatgtcg taagcccatc cgtctccacc gaagatccat tgtgatctct tagctaagta    660
gtcttggtct tttaatattt cttttagcgaa ctcgttagtt tcaccttgta atgcagctac    720
aacagcgtca gctctatctc tagttccttc tccgttgtca acttcagcta tccaagcttc    780
taaagcttct ttagcttctg gtttaacacc agcttcaatt gcttttccag caagatcaac    840
taatcttttct cttatagctt taactcctaa gaacatacct aatccgaatt cagcgttgtc    900
ctcgaataat gagttagccc aagctggtcc atgaccattg tggttagttg tgtatggagt    960
```

```
tgaaggagct gatccacccc agattgatga acatccagta gcgttagcta tcatcattct    1020
atctccgaat aattgagtta aagtttagc atatggagtt tctccacatc cagcacaagc    1080
tcctgagaac tcgaataatg gttgctcgaa ttggctacct ttaactgtgt ttttgttcat    1140
tgggtttttc ttaggtacaa catcatttac acagtaatcc caagcttcta tttgatcttc    1200
ttgagtatgt tgtggtttca taactaaagc ttttttccta gcaggacaaa cttgagcaca    1260
gtttccacat ccagtacagt ctaaagtact tacagcccata gtgaattgca ttggctcttc    1320 agttttaat gctttagcag caactaactt agttgaagca ggagcatttt tagcttcttc    1380
ctcagttaat aagaatggtc ttattgtagc atgaggacaa acgtaagcac attggttaca    1440
ttggatacag ttgtctgcta tccattctgg tatgtttata ccgattcctc tcttttcgta    1500
tgcagcagta cctggttcga aagtaccatc ttccattccg ttgaatgctg atacaggaag    1560
tttatctcct tctaatctgt tcattggttc aacaatgttt ttgatgaatg ctggaacttc    1620
tttagcttca acaacttcat ctttagcgtt agcccactca gctggaacag tgatttcaac    1680
gatagcgtcg attcctttgt ctatagcagc gtggttcatg ttaacaactt tttcaccttt    1740
tttaccgtat gaagttacaa cagcgtcttt taagtattta actgcgtctt ctactggtat    1800
tatgttagct agtttgaaga atgctgattg catgatcatg ttgattcttc cacctaaacc    1860
aacttcttga gctatcttaa cagcatttaa agtgtagaac ttaatgttgt tttcagctaa    1920
gaatctctta tagcttgctg gtaaatgttc agcaacttct tctggagtcc agatagtgtt    1980
taataagaat gttccgtttt tctttaatcc atctaaaacg aagtatttgt taacatatga    2040
ttggttatga caagcaacga aatcagcttt gtttattaag taaggtgatt ttattggttg    2100
tttaccgaat cttaagtgag aaattgtaac cccacctgat ttttagagt catatgcaaa    2160 gtatccttga gcatacatgt cagtatggtc tccgatgatt ttgatagcac tcttgttagc    2220
tccaactgtt ccgtctgatc ctaatcccca gaacttacaa gctttagttc cttctggagt    2280
agtatctata tctccaactg gttctaatga agtgttagtt acgtcatcaa ctattgataa    2340
agtgaatcca ttttagcat cctctttatt taagttttcg taaacagcaa cgatatcagc    2400
tggtacagta tcttttgatc ctaatccgaa tctaccacca actattacag gagcattttc    2460
taatccgtag aatgcattct taacttctaa gtatagaggt tctcctgcag cacctggttc    2520
tttagttcta tctaaaacag caacctttt aacagttttt ggcattgctt ttattaatct    2580
ttcatttgag aatggtctga ataatcttac tttgattaaa ccaactttt ctcctttagc    2640 gtttaagtag tctacagttt cttctattaa gtcagtaact gatcccatag ctacgataac    2700
tctttcagca tctgctgctc catagtaatc gaaacagttg tactctctac cagttaactt    2760
agtgatttct ttcatgtagc tctcaactat ttctggaact gcatcgtaga atttgtttac    2820
tgcttctctt tcttggaagt agatgtctgg gttttgagct gtacctcttg taacaggctt    2880
gttagggtta agagctcttc ttctgaactc ttctacagct tccatatcta ctaattcttt    2940
taattcatcg tattgtaaaa gttcaacttt ttgtatttca tgtgatgttc tgaatccatc    3000
gaagaagttt acgaaaggta ttctagcttt aagagctgct aagtgagcaa ctgctgataa    3060
atccataacc tcttgaactg atccttctgc taacatagcg aatccagttt gtcttgcagc    3120
cataacgtct tggtgatcac cgaagatgtt taatgctgaa gtagctaatg ctctagctga    3180
tacatggaat actgatggta ataattcacc agctattttg tacatgtttg gtatcattaa    3240
taataaacct tgtgaagctg tgtaagtagt agttaaagct ccagcttgta atgaaccgtg    3300
```

```
aactgctcca gcagcacctg cttctgattg catttccatt acttttacag gttgaccaaa    3360
tatgttcttt aatcctcttg cactgttttc atcaacccac tctgccattg gtgatgatgg    3420
agtgataggg aatattgctg caacatcagt gaacgcatat gatatataag cggcagctgt    3480
gttaccatcc atagttttca tttttctcat tgccat                              3516
```

<210> SEQ ID NO 9
<211> LENGTH: 450
<212> TYPE: PRT
<213> ORGANISM: Eimeria tenella

<400> SEQUENCE: 9

```
Met Gly Lys Glu Lys Thr His Ile Asn Leu Val Val Ile Gly His Val
1               5                   10                  15

Asp Ser Gly Lys Ser Thr Thr Thr Gly His Leu Ile Tyr Lys Leu Gly
            20                  25                  30

Gly Ile Asp Lys Arg Thr Ile Glu Lys Phe Glu Lys Glu Ser Ser Glu
        35                  40                  45

Met Gly Lys Ala Ser Phe Lys Tyr Ala Trp Val Leu Asp Lys Leu Lys
    50                  55                  60

Ala Glu Arg Glu Arg Gly Ile Thr Ile Asp Ile Ala Leu Trp Gln Phe
65                  70                  75                  80

Glu Thr Pro Ala Phe His Tyr Thr Val Ile Asp Ala Pro Gly His Arg
                85                  90                  95

Asp Phe Ile Lys Asn Met Ile Thr Gly Thr Ser Gln Ala Asp Val Ala
            100                 105                 110

Leu Leu Val Val Pro Ala Asp Gln Gly Gly Phe Glu Gly Ala Phe Ser
        115                 120                 125

Lys Glu Gly Gln Thr Arg Glu His Ala Leu Leu Ala Phe Thr Leu Gly
    130                 135                 140

Val Lys Gln Met Ile Val Gly Ile Asn Lys Met Asp Ala Thr Ser Pro
145                 150                 155                 160

Glu Lys Tyr Ser Glu Ala Arg Phe Asn Glu Ile Gln Ala Glu Val Ser
                165                 170                 175

Arg Tyr Leu Lys Thr Val Gly Tyr Asn Pro Glu Lys Val Pro Phe Val
            180                 185                 190

Pro Ile Ser Gly Phe Val Gly Asp Asn Met Val Glu Arg Ser Ser Asn
        195                 200                 205

Met Gly Trp Tyr Lys Gly Lys Thr Leu Val Glu Ala Leu Asp Ser Val
    210                 215                 220

Glu Pro Pro Lys Arg Pro Val Asp Lys Pro Leu Arg Leu Pro Leu Gln
225                 230                 235                 240

Asp Val Tyr Lys Ile Gly Gly Ile Gly Thr Val Pro Val Gly Arg Val
                245                 250                 255

Glu Thr Gly Val Leu Lys Pro Gly Met Val Val Thr Phe Ala Pro Ser
            260                 265                 270

Gly Leu Gln Thr Glu Val Lys Ser Val Glu Met His His Ala Gln Leu
        275                 280                 285

Glu Gln Ala Val Pro Gly Asp Asn Val Gly Phe Asn Val Lys Asn Val
    290                 295                 300

Ser Val Lys Asp Val Lys Arg Gly His Val Ala Ser Asp Ser Lys Asn
305                 310                 315                 320

Asp Pro Ala Lys Ala Ala Ala Ser Phe Gln Ala Gln Val Ile Val Leu
                325                 330                 335
```

```
His His Pro Gly Gln Ile Asn Pro Gly Tyr Thr Pro Val Leu Asp Cys
            340                 345                 350

His Thr Ala His Ile Ser Cys Lys Phe Ala Asp Leu Glu Lys Arg Leu
            355                 360                 365

Asp Arg Arg Ser Gly Lys Ala Leu Glu Asp Ser Pro Lys Ser Ile Lys
            370                 375                 380

Ser Gly Asp Ala Ala Ile Val Arg Met Glu Pro Ser Lys Pro Met Cys
385                 390                 395                 400

Val Glu Ala Phe Ile Glu Tyr Pro Pro Leu Gly Arg Phe Ala Val Arg
                405                 410                 415

Asp Met Lys Gln Thr Ile Ala Val Gly Val Ile Lys Ala Val Glu Lys
            420                 425                 430

Lys Glu Ala Gly Gly Lys Val Thr Lys Ser Ala Gln Lys Ala Ala Ala
            435                 440                 445

Lys Lys
    450

<210> SEQ ID NO 10
<211> LENGTH: 1353
<212> TYPE: DNA
<213> ORGANISM: Eimeria tenella

<400> SEQUENCE: 10
atggggaagg aaaagacgca cataaacctg gtggtgatcg ccacgtggga cagcgggaaa       60
agcaccacca cgggccacct gatctacaaa ctcggcggca tcgacaaaag gaccatcgaa      120
aagttcgaaa aagagtcttc cgaaatgggc aaggcctcct tcaagtacgc ctgggtcctc      180
gacaagctca aggccgagcg cgagcgcggc atcaccatcg acatcgctct ctggcagttc      240
gagactcccg ccttccacta caccgtcatt gacgcgccgg ccaccgcga cttcatcaaa       300 aacatgatta ccggcacgtc tcaggcggac gtcgcgttgc tcgtcgtgcc tgcggaccag      360
ggcggcttcg agggcgcctt ctccaaggaa gggcagacgc gggaacacgc gctgctggcg      420
ttcacgctgg gcgtgaagca gatgatcgtg gggataaaca aaatggacgc gacttcgccg      480
gagaagtaca gcgaggcgcg gttcaacgaa atccaagccg aagtgtcgcg gtacctgaag      540
acagtgggct acaacccgga gaaagtgccg ttcgtgccga tctcaggctt cgtgggcgac      600
aacatggtgg agcgcagcag caacatgggc tggtacaagg gcaaaacgct ggtggaggct      660
ttggacagcg tggagccccc gaagcgcccc gtggacaagc cgctgcggct gccgctgcag      720
gacgtgtaca agatcggcgg gatcggcacg gtccccgtgg ggcgcgtgga cgggcgtg        780 ctgaagccag gcatggtggt gaccttcgcg ccctcggggc tgcagacgga ggtcaagtcc      840
gtggagatgc accacgcgca gctggagcag ccgtccccg gagacaacgt gggcttcaac       900
gtgaaaaacg tctccgtcaa ggacgtcaag gcgccacg tcgcctccga ctccaagaac        960
gaccccgcca aggccgccgc cagcttccag gcccaggtca tcgtcctgca ccacccggc      1020 cagatcaacc ccggctacac gcccgtcctc gactgccaca tgcgcacat cagttgcaag     1080 ttcgccgacc tcgagaagcg cctcgaccgc cgcagcggca ggctctcga ggactctccc     1140 aagtccatca gagcggcga cgccgccatc gtcaggatgg agcccagcaa gcccatgtgc     1200
gtcgaggctt tcatcgagta cccgccgctc ggccgcttcg ccgtccgcga catgaagcag     1260
accattgccg tcggcgtcat caaggccgtc gagaagaagg aggctggcgg caaggtcacc     1320
aagagtgcgc agaaggccgc cgccaagaag tga                                  1353
```

<210> SEQ ID NO 11
<211> LENGTH: 170
<212> TYPE: PRT
<213> ORGANISM: Eimeria tenella

<400> SEQUENCE: 11

Met Gly Glu Glu Ala Asp Thr Gln Ala Trp Asp Thr Ser Val Lys Glu
1               5                   10                  15

Trp Leu Val Asp Thr Gly Lys Val Tyr Ala Gly Ile Ala Ser Ile
            20                  25                  30

Ala Asp Gly Cys Arg Leu Phe Gly Ala Ala Ile Asp Asn Gly Glu Asp
        35                  40                  45

Ala Trp Ser Gln Leu Val Lys Thr Gly Tyr Gln Ile Glu Val Leu Gln
    50                  55                  60

Glu Asp Gly Ser Ser Thr Gln Glu Asp Cys Asp Ala Glu Thr Leu
65                  70                  75                  80

Arg Gln Ala Ile Val Asp Gly Arg Ala Pro Asn Gly Val Tyr Ile Gly
                85                  90                  95

Gly Ile Lys Tyr Lys Leu Ala Glu Val Lys Arg Asp Phe Thr Tyr Asn
            100                 105                 110

Asp Gln Asn Tyr Asp Val Ala Ile Leu Gly Lys Asn Lys Gly Gly
        115                 120                 125

Phe Leu Ile Lys Thr Pro Asn Asp Asn Val Val Ile Ala Leu Tyr Asp
    130                 135                 140

Glu Glu Lys Glu Gln Asn Lys Ala Asp Ala Leu Thr Thr Ala Leu Ala
145                 150                 155                 160

Phe Ala Glu Tyr Leu Tyr Gln Gly Gly Phe
                165                 170

<210> SEQ ID NO 12
<211> LENGTH: 513
<212> TYPE: DNA
<213> ORGANISM: Eimeria tenella

<400> SEQUENCE: 12
atgggtgaag aggctgatac tcaggcgtgg gataccctcag tgaaggaatg gctcgtggat      60
acggggaagg tatacgccgg cggcattgct agcattgcag atgggtgccg cctgtttggc     120
gctgcaatag acaatgggga ggatgcgtgg agtcagttgg tgaagacagg atatcagatt     180
gaagtgcttc aagaggacgg ctcttcaact caagaggact gcgatgaagc ggaaaccctg     240
cggcaagcaa ttgttgacgg ccgtgcccca acggtgtttt atattggagg aattaaatat     300
aaactcgcag aagttaaacg tgatttcacc tataacgacc agaactacga cgtggcgatt     360
ttggggaaga acaagggtgg cggtttcctg attaagactc cgaacgacaa tgtggtgatt     420
gctctttatg acgaggagaa agagcagaac aaagcagatg cgctgacaac ggcacttgcc     480
ttcgctgagt acctgtacca gggcggcttc taa                                  513